(12) United States Patent
Covey et al.

(10) Patent No.: US 7,781,421 B2
(45) Date of Patent: Aug. 24, 2010

(54) NEUROACTIVE 13, 24-CYCLO-18, 21-DINORCHOLANES AND STRUCTURALLY RELATED PENTACYCLIC STERIODS

(75) Inventors: Douglas F. Covey, Ballwin, MO (US); Xin Jiang, Baltimore, MD (US)

(73) Assignee: Washington University, St. Louis, MO (US)

( * ) Notice: Subject to any disclaimer, the term of this patent is extended or adjusted under 35 U.S.C. 154(b) by 1212 days.

(21) Appl. No.: 10/856,314

(22) Filed: May 28, 2004

(65) Prior Publication Data

US 2004/0242549 A1 Dec. 2, 2004

Related U.S. Application Data

(60) Provisional application No. 60/474,152, filed on May 29, 2003.

(51) Int. Cl.
 *A61K 31/56* (2006.01)
 *A61K 31/58* (2006.01)
 *C07J 53/00* (2006.01)
 *C07J 71/00* (2006.01)

(52) U.S. Cl. ............... 514/179; 514/172; 514/173; 540/15; 540/76; 552/510

(58) Field of Classification Search ............... 552/510; 540/15, 76; 514/172, 173, 179
See application file for complete search history.

(56) References Cited

FOREIGN PATENT DOCUMENTS

WO   WO 9825948   *   6/1998

OTHER PUBLICATIONS

Kashiwada et al., Journal of Natural Products, col. 60(11), pp. 1105-1114, 1997.*
Anderson, A. et al., "Conformationally Constrained Anesthetic Steroids That Modulate GABAA Receptors", J. Med. Chem., (2000), pp. 4118-4125, vol. 43.
Jiang, X. et al., "Neurosteroid Analogues. 9. Conformationally Constrained Pregnanes: Structure-Activity Studies of 13,24-Cyclo-18,21-dinorcholane Analogues of the GABA Modulatory and Anesthetic Steroids (3α,5α)- and (3α,5β)-3- Hydroxypregnan-20-one", J. Med. Chem., (2003), pp. 5334-5348, vol. 46.
Kashiwada, Y. et al., "Chemical Studies on Cumingianosides and Cumindysoside A, Potent Antileukemic Triterpene Glucosides with a 14,18-cycloapoeuphane Skeleton", Tennen Yuki Kagobutsu Toronkai Koen Yoshishu, (1995), pp. 307-312, 37th (Abstract only).
Lambert, J.J. et al., "Modulation of Native and Recombinant GABAA Receptors by Endogenous and Synthetic Neuroactive Steroids", Brain Research Reviews, (2001), pp. 68-80, vol. 37.
Vidic, H.J. et al., "Mikrobiologische Hydroxylierung von 3α-Acetoxy-5β-pregnan-20-carbonsäure und deren Methylester mit Calonectria decora und Syncephalastrum racemosum", Chem. Ber., (1978), pp. 2143-2151, vol. 111.

Zainos, A. et al., "Turning Behavior, Barrel Rolling, and Sensory Neglect Induced by Picrotoxin in the Thalamus", Experimental Neurology, (1984), pp. 534-547, vol. 83:3 (Abstract only).
Corey, E.J. et al., "Novel Annulation Products Derived by Selective Attack on the C(18) Angular Methyl Group of the Cardenolide Ouabain", Tetrahedron Letters, (1999), pp. 2061-2064, vol. 40.
Covey, D.F. et al., "Recent Developments in Structure—Activity Relationships for Steroid Modulators of $GABA_A$ Receptors", Brain Research Reviews, (2001), pp. 91-97, vol. 37.
Hogenkamp, D.J. et al., "Synthesis and in Vitro Activity of 3β-Substituted-3α-Hydroxypregnan-20- Ones: Allosteric Modulators of the $GABA_A$ Receptor", J. Med. Chem., (1997), pp. 61-72, vol. 40.
Jeanniot, J.P. et al., "Alcaloïdes Stéroïdiques CVIII, Elimination Trans Stéréosélective, En Milieu Alcalin, D'un Oxaziranne Stéroïdique, Dérivé De La Conanine", Tetrahedron., (1971), pp. 401-410, vol. 27.
Kalvoda, J. et al., "93. Photolysis of Steroidal 20-Aryl-Substituted 11-Nitrites", Helvetica Chimica Acta, (1997), pp. 1221-1228, vol. 80.
Kasal, a. et al., "On Steroids. CVIII., Preparation and Properties of Some Androstan-18-Carboxylic Acid Derivatives", Collection Czechoslov, Chem. Commun., (1967), pp. 3733-3745, vol. 32.
Kirk, D.N. et al., "18-Substituted Steroids—9[1]Studies on the Stability of Aldosterone in Dilute Alkali", Journal of Steroid Biochemistry, (1982), pp. 269-276, vol. 16.
Majewska, M.D., "Neurosteroids: Endogenous Bimodal Modulators of the $GABA_A$ Receptor. Mechanism of Action and Physiological Significance", Progress in Neurobiology, (1992), pp. 379-395, vol. 38.
Mennerick, S. et al., "Effects on γ-Aminobutyric Acid ($GABA_A$) Receptors of a Neuroactive Steroid That Negatively Modulates Glutamate Neurotransmission and Augments GABA Neurotransmission", Molecular Pharmacology, (2001), pp. 732-741, vol. 60:4.
Milliet, P. et al., "Action Comparée De L'eau Oxygénée Et D'un Peracide Sur Un Sel D'immonium Pyrrolinique Stéroïdique Et Sur L'énamine Correspondante. Formation Et Propriétés D'un Sel D'oxaziridinium", Tetrahedron, (1981), pp. 4201-4208, vol. 37:24.
Miyano, M. et al., "Regioselective Synthesis Using the Deuterium Istope Effect", J. Org. Chem., (1981), pp. 1854-1857, vol. 46:9.
Perard, S. et al., "18-Functionalized Steroids: Synthesis of Thioderivative of Progesterone", Steroids, (1990), pp. 271-275, vol. 55.

(Continued)

*Primary Examiner*—Barbara P Badio
(74) *Attorney, Agent, or Firm*—Senniger Powers LLP

(57) ABSTRACT

Novel pentacyclic steroids and pentacyclic D-homosteroids comprising: (i) the tetracyclic steroid ring system or tetracyclic D-homosteroid ring system, respectively; (ii) a C(3) substituent selected from the group consisting of (a) a hydroxyl or carboxyl in the α-configuration and (b) a sulfate or other negatively charged moiety; and (iii) a fused fifth ring, the fused fifth ring comprising a hydrogen bond acceptor, and (a) in the case of the pentacyclic steroid the C(13) and C(17) carbons, or (b) in the case of the pentacyclic D-homosteroid the C(13) and C(17a) carbons, having utility as anesthetics and in the treatment of disorders relating to GABA function and activity.

39 Claims, 1 Drawing Sheet

OTHER PUBLICATIONS

Petrovic, G. et al., "Annulation of the Cyclohexane Ring by Tandem Free Radical Alkylation of a Nonactivated ζ-Carbon Atom—Intramolecular Carbanion Cycloalkylation", Organic Letters, (2000), pp. 3769-3772, vol. 2:24.

Sear, J.W., "ORG 21465, A New Water-Soluble Steroid Hypnotic: More of the Same or Something Different?", British Journal of Anaesthesia, (1997), pp. 417-419, vol. 79.

Upasani, R.B. et al., "3α-Hydroxy-3β-(Phenylethynyl)-5β-Pregnan-20-Ones: Synthesis and Pharmacological Activity of Neuroactive Steroids with High Affinity for $GABA_A$ Receptors", J. Med. Chem., (1997), pp. 73-84, vol. 40:1.

Van Moorselaar, R. et al., "Investigations on Sterols XXXIII, Synthesis of 18-Alkyl-9β, 10α-Pregnane Derivatives", Recueil, (1969), pp. 737-751, vol. 88.

Zorumski, C.F. et al., "Potential Clinical Uses of Neuroactive Steroids", Current Opinion in Investigational Drugs, (2000), pp. 360-369, vol. 1:3.

Bogan, P. et al., "17,18-Cyclo Steroids", Aust. J. Chem., Oct. 1979, pp. 2323-2326, vol. 32, No. 10.

Kashiwada Y. et al., Antitumor Agents. 180. Chemical Studies and Cytotoxic Evaluation of Cumingianosides and Cumindysoside A., Antileukemic Triterpene Glucosides with a 14,18-Cycloapotirucallane Skeleton, Journal of Natural Products, Nov. 1997, pp. 1105-1114, vol. 60, No. 11.

PCT International Search Report for PCT/US2004/17055 dated Nov. 29, 2004, 2 pages.

* cited by examiner

FIG. 1
Electrophysiological responses to GABA potentiated by cyclosteroids
FIG. 1A
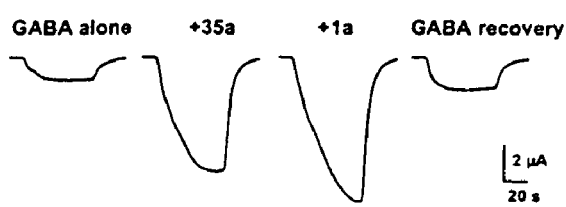
FIG. 1B
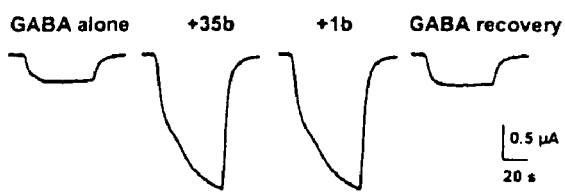
FIG. 1C
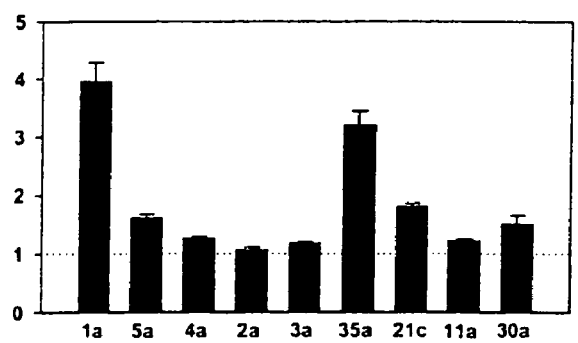
FIG. 1D
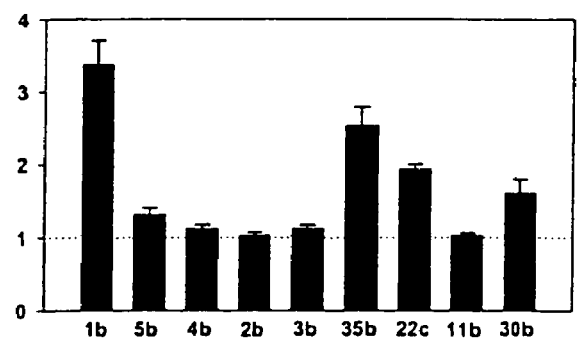

NEUROACTIVE 13, 24-CYCLO-18, 21-DINORCHOLANES AND STRUCTURALLY RELATED PENTACYCLIC STERIODS

CROSS REFERENCE TO RELATED APPLICATION

This application claims the benefit of U.S. Ser. No. 60/474,152, filed May 29, 2003, which is incorporated herein by reference in its entirety.

This invention was made with Government support under NIH Grant # 5 PO1 GM47969 awarded by the National Institutes of Health. The Government has certain rights in the invention.

BACKGROUND OF THE INVENTION

The present invention is directed to novel pentacyclic steroids and novel pentacyclic D-homosteroids that have utility as anesthetics and in the treatment of disorders relating to GABA function and activity.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are coupled to chloride ion channels; activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold) as well as anxiolytic and anesthetic effects. Recently, the effect of steroids on $GABA_A$ receptors has been demonstrated. As a result, researchers are pursuing the discovery and synthesis of neuroactive steroids that act as anesthetics and/or serve to provide treatment for disorders related to GABA function.

In addition to anesthetic properties, neuroactive steroids may be used to treat disorders related to GABA function. For example, neuroactive steroids may be used as sedative-hypnotics. Progesterone, for example, exhibits benzodiazepine-like actions, inducing reduced sleep latency and increased non-REM sleep with only small changes in slow wave and REM sleep. Further, systemic administration of GABA-enhancing steroids has demonstrated anticonvulsant effects in animals. In addition, drugs that enhance GABA responses are often used to treat anxiety in humans. Thus, it might be expected that GABA-potentiating steroids would exhibit anxiolytic effects. In addition to uses as sedative-hypnotics, anticonvulsants, and anxiolytics, neuroactive steroids may be used to treat depression. Accumulating evidence suggests that patients with major depression have decreased levels of GABAergic neurosteroids, and that certain treatments for depression alter levels of these steroids. Although GABA is not typically thought to play a critical role in the biology of depression, there is evidence that low GABAergic activity may predispose to mood disorders. Finally, inhibition of NMDA receptors and enhancement of $GABA_A$ receptors appear to play important roles in mediating the acute effects of ethanol in the nervous system. Recent studies suggest that GABAergic neurosteroids may be involved in some of the pharmacological effects of ethanol and that neuroactive steroids may be useful in treating ethanol withdrawal.

An alternative to developing GABAergic anesthetics is to focus on steroids that inhibit NMDA receptors. However, steroids that inhibit NMDA receptors often block $GABA_A$ receptors as well, resulting in complex effects on CNS excitability. Neuroactive steroids containing a 3β-sulfate group inhibit $GABA_A$ receptors non-competitively. These agents act by enhancing $GABA_A$ receptor desensitization and display different degrees of enantioselectivity. These compounds may be useful as memory enhancers and in reversing the anesthetic effects of compounds that potentiate GABA at $GABA_A$ receptors.

SUMMARY OF THE INVENTION

Among the various aspects of the present invention, therefore, is the provision of neuroactive 13,24-cyclo-18,21-dinorcholanes, and structurally related pentacyclic steroids and pentacyclic D-homosteroids, which potentiate the effects of GABA at $GABA_A$ receptors useful for producing anesthesia or treating disorders related to GABA function such as insomnia, mood disorders, convulsive disorders, anxiety, or symptoms of ethanol withdrawal. Another aspect of the present invention is the provision of neuroactive 13,24-cyclo-18,21-dinorcholanes, and structurally related pentacyclic steroids and pentacyclic D-homosteroids that inhibit the effect of GABA at $GABA_A$ receptors useful for memory enhancement and reversing the effects of compounds that potentiate GABA at $GABA_A$ receptors.

Briefly, therefore, the present invention is directed to pentacyclic steroids and pentacyclic D-homosteroids comprising:

(i) the tetracyclic steroid ring system or tetracyclic D-homosteroid ring system, respectively;

(ii) a C(3) substituent selected from the group consisting of (a) a hydroxyl or carboxyl in the α-configuration and (b) a sulfate or other negatively charged moiety; and (iii) a fused fifth ring, the fused fifth ring comprising a hydrogen bond acceptor, and (a) in the case of the pentacyclic steroid the C(13) and C(17) carbons, or (b) in the case of the pentacyclic D-homosteroid the C(13) and C(17a) carbons, wherein the tetracyclic steroid ring system corresponds to Formula (I)

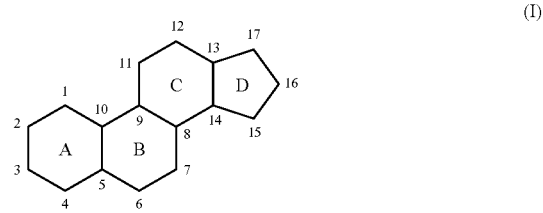

(I)

and the tetracyclic D-homosteroid ring system corresponds to Formula (II)

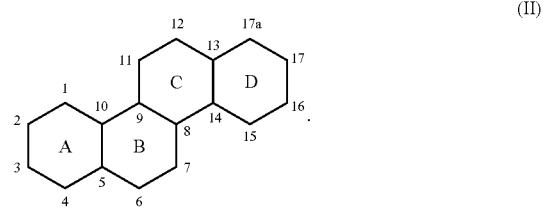

(II)

Other objects and features of the present invention will be in part apparent and in part pointed out hereafter.

BRIEF DESCRIPTION OF THE DRAWINGS

These and other features, aspects, and advantages of the present invention will become better understood with regard to the following description, appended claims and accompanying figures where:

FIG. 1 shows two current traces (chloride currents) (FIGS. 1A and 1B) and two tables (FIGS. 1C and 1D) demonstrating the effect of cyclosteroids on electrophysiological responses to GABA in oocytes. In particular, FIG. 1A and FIG. 1B depict current traces for application of GABA to GABA receptors in the absence of cyclosteroids and in the presence of certain cyclosteroids; compound 35a (FIG. 1A) and compound 35b (FIG. 1B) and reference compound 1a (FIG. 1A) and compound 1b (FIG. 1B). FIG. 1C shows a table of chloride current versus specific compounds, which summarizes the effects of certain cyclosteroids tested at 500 nM against the response to 2 μM GABA alone (dotted line denotes the normalized response to GABA alone). FIG. 1D depicts a similar summary for the 5β-reduced series.

DETAILED DESCRIPTION OF THE PREFERRED EMBODIMENTS

In general, the present invention is directed to pentacyclic steroids and D-homosteroids. The pentacyclic steroids comprise the tetracyclic ring system of Formula (I) and the pentacyclic D-homosteroids comprise the tetracyclic ring system of Formula (II):

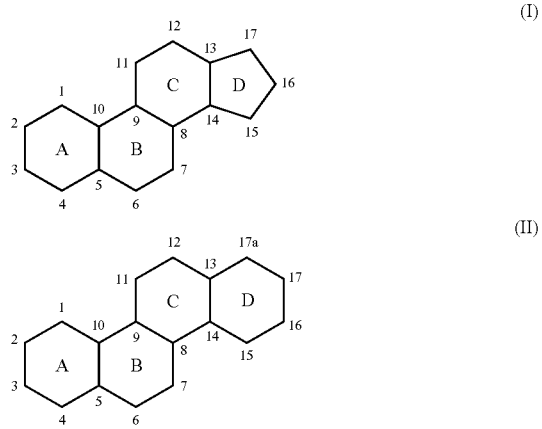

In addition, the pentacyclic steroids comprise a fifth fused ring, sometimes identified herein as the "E" ring, the fifth fused ring comprising the carbon atoms at the C(13) and C(17) positions of Formula (I). Similarly, the pentacyclic D-homosteroids comprise a fifth fused ring, sometimes identified herein as the "E" ring comprising the carbon atoms at the C(13) and C(17a) positions. The pentacyclic steroids or pentacyclic D-homosteroids further comprise an E ring hydrogen bond acceptor.

In one embodiment, the compound is a pentacyclic steroid wherein each of rings A, B, C, and D of Formula (I) are saturated and the E ring is a 5- or 6-membered carbocyclic ring. Further, the E ring may be saturated. Alternatively, at least one pair of ring atoms of the E ring share a double bond. While the E ring may be fully saturated or partially unsaturated, the E ring hydrogen bond acceptor is selected from the group consisting of keto (=O), cyano (CN), acyl, =CHX$_1$, —OX$_2$, —C(O)X$_2$, epoxide, an E ring alkene bond (that is, a carbon-carbon alkene bond between two E ring carbon atoms), and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl. Typically, the E ring hydrogen bond acceptor is selected from the group consisting of keto, cyano, methylene (=CH$_2$), methoxy (—OCH$_3$), acetyl (—C(O)CH$_3$), =CHCN, =CHC(O)CH$_3$, and an E ring alkene bond. Additionally, the E ring may comprise substituents selected from the group consisting of halo and alkyl. Further, for any of the above variations, the hydroxyl or carboxyl in the α-configuration at C(3) may be directly bonded to the C(3) position or bonded via a linking group. For example, when the E ring is saturated and the hydrogen bond acceptor is keto, cyano, methylene, methoxy, acetyl, =CHCN, or =CHC(O)CH$_3$, the hydroxyl in the α-configuration at C(3) may be directly bonded to the C(3) position or bonded via a linking group. Preferable linking groups include methylene, ethylene, methoxy, and ethoxy. Alternatively, when at least one pair of ring atoms of the E ring share a double bond and the hydrogen bond acceptor is keto, cyano, methylene, methoxy, acetyl, =CHCN, =CHC(O)CH$_3$, or an E ring alkene bond, the hydroxyl in the α-configuration at C(3) may be directly bonded to the C(3) position or bonded via a linking group.

In another embodiment, the compound is a pentacyclic steroid wherein at least one pair of ring atoms comprising rings A, B, C, and D of Formula (I) share a double bond and the E ring is a 5- or 6-membered carbocyclic ring. Further, the E ring may be saturated. Alternatively, at least one pair of ring atoms of the E ring share a double bond. While the E ring may be fully saturated or partially unsaturated, the E ring hydrogen bond acceptor is selected from the group consisting of keto, cyano, acyl, =CHX$_1$, —OX$_2$, —C(O)X$_2$, epoxide, an E ring alkene bond, and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl. Typically, the E ring hydrogen bond acceptor is selected from the group consisting of keto, cyano, methylene, methoxy, acetyl, =CHCN, =CHC(O)CH$_3$, and an E ring alkene bond. Additionally, the E ring may comprise substituents selected from the group consisting of halo and alkyl. Further, for any of the above variations, the hydroxyl or carboxyl in the α-configuration at C(3) may be directly bonded to the C(3) position or bonded via a linking group. For example, when the E ring is saturated and the hydrogen bond acceptor is keto, cyano, methylene, methoxy, acetyl, =CHCN, or =CHC(O)CH$_3$, the hydroxyl in the α-configuration at C(3) may be directly bonded to the C(3) position or bonded via a linking group. Preferable linking groups include methylene, ethylene, methoxy, and ethoxy. Alternatively, when at least one pair of ring atoms of the E ring share a double bond and the hydrogen bond acceptor is keto, cyano, methylene, methoxy, acetyl, =CHCN, =CHC(O)CH$_3$, or an E ring alkene bond, the hydroxyl in the α-configuration at C(3) may be directly bonded to the C(3) position or bonded via a linking group.

In another embodiment, the compound is a pentacyclic D-homosteroid wherein each of rings A, B, C, and D of Formula (II) are saturated and the E ring is a 5- or 6-membered carbocyclic ring. Further, the E ring may be saturated. Alternatively, at least one pair of ring atoms of the E ring share a double bond. While the E ring may be fully saturated or partially unsaturated, the E ring hydrogen bond acceptor is selected from the group consisting of keto, cyano, acyl, =CHX$_1$, —OX$_2$, —C(O)X$_2$, epoxide, an E ring alkene bond, and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl. Typically, the E ring hydrogen bond acceptor is selected from the group consisting of keto, cyano, methylene, methoxy, acetyl, =CHCN, =CHC(O)CH$_3$, and an E ring alkene bond. Additionally, the E ring may comprise substituents selected from the group consisting of halo and alkyl. Further, for any of the above variations, the hydroxyl or carboxyl in the α-configuration at C(3) may be directly bonded to the C(3) position or bonded via a linking group. For example, when the E ring is saturated and the hydrogen bond acceptor is keto, cyano, methylene, methoxy, acetyl, =CHCN, or =CHC(O)CH$_3$, the hydroxyl in the α-configuration at C(3) may be directly bonded to the C(3) position or bonded via a linking group. Preferable linking groups include methylene, ethylene, methoxy, and ethoxy. Alternatively, when at least one pair of ring atoms of the E ring share a double bond and the hydrogen bond acceptor is keto, cyano, methylene, methoxy, acetyl, =CHCN, =CHC(O)CH$_3$, or an E ring alkene bond, the hydroxyl in the α-configuration at C(3) may be directly bonded to the C(3) position or bonded via a linking group.

In yet another embodiment, the compound is a pentacyclic D-homosteroid wherein at least one pair of ring atoms comprising rings A, B, C, and D of Formula (II) share a double bond and the E ring is a 5- or 6-membered carbocyclic ring. Further, the E ring may be saturated. Alternatively, at least one pair of ring atoms of the E ring share a double bond. While the E ring may be fully saturated or partially unsaturated, the E ring hydrogen bond acceptor is selected from the group consisting of keto, cyano, acyl, =CHX$_1$, —OX$_2$, —C(O)X$_2$, epoxide, an E ring alkene bond, and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl. Typically, the E ring hydrogen bond acceptor is selected from the group consisting of keto, cyano, methylene, methoxy, acetyl, =CHCN, =CHC(O)CH$_3$, and an E ring alkene bond. Additionally, the E ring may comprise substituents selected from the group consisting of halo and alkyl. Further, for any of the above variations, the hydroxyl or carboxyl in the α-configuration at C(3) may be directly bonded to the C(3) position or bonded via a linking group. For example, when the E ring is saturated and the hydrogen bond acceptor is keto, cyano, methylene, methoxy, acetyl, =CHCN, or =CHC(O)CH$_3$, the hydroxyl in the α-configuration at C(3) may be directly bonded to the C(3) position or bonded via a linking group. Preferable linking groups include methylene, ethylene, methoxy, and ethoxy. Alternatively, when at least one pair of ring atoms of the E ring share a double bond and the hydrogen bond acceptor is keto, cyano, methylene, methoxy, acetyl, =CHCN, =CHC(O)CH$_3$, or an E ring alkene bond, the hydroxyl in the α-configuration at C(3) may be directly bonded to the C(3) position or bonded via a linking group.

In a preferred embodiment, the compound is a pentacyclic steroid comprising the tetracyclic steroid ring system, Formula (I), wherein each of rings A, B, C, and D of Formula (I) are fully saturated, the E ring is a 6-membered carbocyclic ring, the E ring hydrogen bond acceptor is an E ring alkene bond or is selected from the group consisting of keto, cyano, acyl, =CHX$_1$, —OX$_2$, —C(O)X$_2$, and an epoxide; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl, and the hydroxyl or carboxyl group is directly bonded to C(3). Alternatively, the hydroxyl or carboxyl group is bonded to C(3) via a linking group as defined for any of the previous embodiments.

In another preferred embodiment, the compound is a pentacyclic steroid comprising the tetracyclic steroid ring system, Formula (I), wherein at least one pair of ring atoms comprising rings A, B, C, and D share a double bond, the E ring is a 6-membered carbocyclic ring, the E ring hydrogen bond acceptor is an E ring alkene bond or is selected from the group consisting of keto, cyano, acyl, =CHX$_1$, —OX$_2$, —C(O)X$_2$, and an epoxide; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl, and the hydroxyl or carboxyl group is directly bonded to C(3). Alternatively, the hydroxyl or carboxyl group is bonded to C(3) via a linking group as defined for any of the previous embodiments.

In another embodiment, the pentacyclic steroids or pentacyclic D-homosteroids comprise Formulae (I) or (II), respectively, and the steroids or D-homosteroids have the standard steroid or D-homosteroid stereochemical configuration (8β, 9α,10β,13β,14α). In this embodiment, the hydrogen at C(5), if present, may be in either the α-configuration or the β-configuration.

In another embodiment, the pentacyclic steroids or pentacyclic D-homosteroids of the present invention correspond to Formula (A)

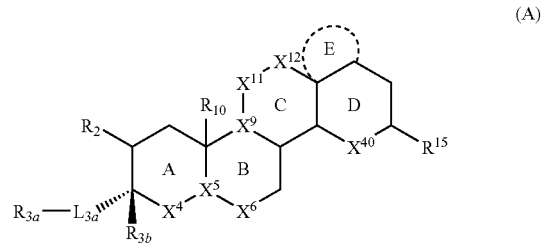

(A)

wherein

R$_2$ is selected from the group consisting of hydrogen, alkoxy, and substituted or unsubstituted morpholine;

R$_{3a}$ is hydroxy or carboxyl;

R$_{3b}$ is hydrogen, alkyl, alkenyl, or alkynyl optionally substituted with halo, hydroxy, or substituted or unsubstituted aryl;

R$_5$ is α- or β-hydrogen;

R$_{10}$ is hydrogen or C$_{1-4}$ alkyl;

R$_{15}$ is hydrogen or oxo;

R$_6$, R$_{11}$, and R$_{12}$ are independently hydrogen or oxo;

L$_{3a}$ is selected from the group consisting of a bond, C$_{1-3}$ alkyl, heterosubstituted C$_{1-3}$ alkyl, or alkoxy;

$X_4$-$X_5$-$X_6$ is selected from the group consisting of

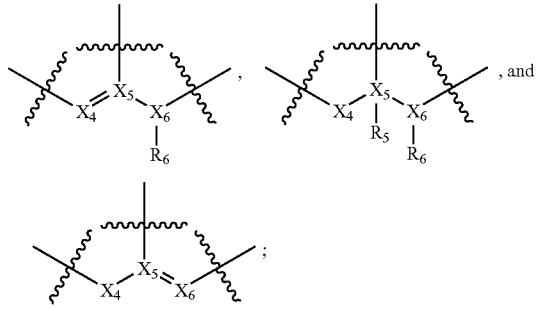

, and

;

$X_9$-$X_{11}$-$X_{12}$ is selected from the group consisting of

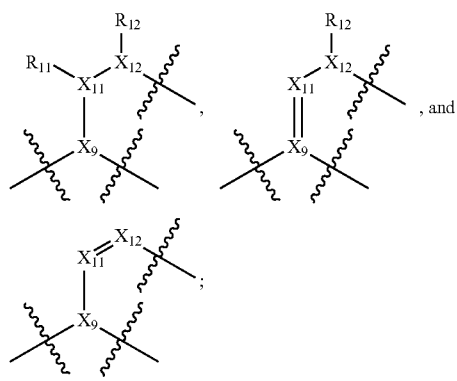

, and

;

$X_{40}$ is a bond or a carbon atom; and

E is a 5- or 6-membered carbocyclic ring, comprising a hydrogen bond acceptor.

In one embodiment where the compounds correspond to Formula (A), $X_{40}$ is a bond. In this embodiment the carbocyclic ring, E, may be in the β-configuration in relation to the C and D rings. Further, the E ring hydrogen bond acceptor may be an E ring alkene bond or may be selected from the group consisting of keto, cyano, acyl, =CHX$_1$, —OX$_2$, —C(O)X$_2$, epoxide, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl. Preferably, the E ring hydrogen bond acceptor is selected from the group consisting of keto, cyano, methylene, methoxy, acetyl, =CHCN, =CHC(O)CH$_3$, and an E ring alkene bond. In certain preferred embodiments, the hydrogen bond acceptor is keto, cyano, or =CHCN. While the E ring may be as defined above for this embodiment, $R_2$ may be selected from the group consisting of hydrogen and substituted or unsubstituted morpholine. Preferably, $R_2$ is hydrogen. While the E ring and $R_2$ may be as defined above for this embodiment, $L_{3a}$ may be a bond, methylene, ethylene, methoxy or ethoxy and $R_{3a}$ may be hydroxyl. Alternatively, $L_{3a}$ may be a bond, methylene, ethylene, methoxy or ethoxy and $R_{3a}$ may be carboxyl. $L_{3a}$ is preferably a bond. In certain instances of this embodiment, $X_4$-$X_5$-$X_6$ may be

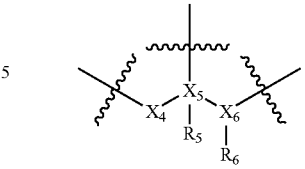

and $X_9$-$X_{11}$-$X_{12}$ may be

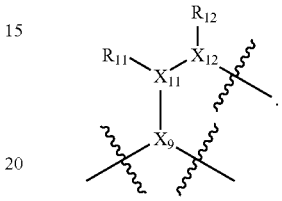

.

Further, $R_{3b}$ may be hydrogen or ethynyl substituted with alkyl or optionally substituted aryl. $R_{3b}$ is preferably hydrogen or ethynyl substituted with phenyl substituted with amino, dimethylamino, hydroxyl, carboxyl, or alkoxy. Still further, in this embodiment, $R_{10}$ may be hydrogen or β-methyl.

In another embodiment where the compounds correspond to Formula (A), $X_{40}$ is carbon. In this embodiment, the carbocyclic ring, E, may be in the β-configuration in relation to the C and D rings. Further, the E ring hydrogen bond acceptor may be an E ring alkene bond or may be selected from the group consisting of keto, cyano, acyl, =CHX$_1$, —OX$_2$, —C(O)X$_2$, epoxide, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl. Preferably, the E ring hydrogen bond acceptor is selected from the group consisting of keto, cyano, methylene, methoxy, acetyl, =CHCN, =CHC(O)CH$_3$, and an E ring alkene bond. In certain preferred embodiments, the hydrogen bond acceptor is keto, cyano, or =CHCN. While the E ring may be as defined above for this embodiment, $R_2$ may be selected from the group consisting of hydrogen and substituted or unsubstituted morpholine. Preferably, $R_2$ is hydrogen. While the E ring and $R_2$ may be as defined above for this embodiment, $L_{3a}$ may be a bond, methylene, ethylene, methoxy or ethoxy and $R_{3a}$ may be hydroxyl. Alternatively, $L_{3a}$ may be a bond, methylene, ethylene, methoxy or ethoxy and $R_{3a}$ may be carboxyl. $L_{3a}$ is preferably a bond. In certain instances of this embodiment, $X_4$-$X_5$-$X_6$ may be

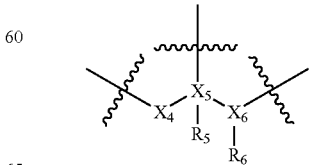

and $X_9$-$X_{11}$-$X_{12}$ may be

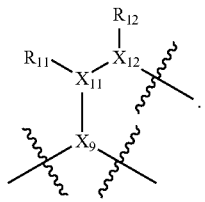

Further, $R_{3b}$ may be hydrogen or ethynyl substituted with alkyl or optionally substituted aryl. $R_{3b}$ is preferably hydrogen or ethynyl substituted with phenyl substituted with amino, dimethylamino, hydroxyl, carboxyl, or alkoxy. Still further, in this embodiment, $R_{10}$ may be hydrogen or β-methyl.

In a preferred embodiment, the compounds correspond to Formula (A), $X_{40}$ is a bond or carbon, $R_2$ is hydrogen, $R_{3b}$ is hydrogen, $R_{10}$ is β-methyl, $L_{3a}$ is a bond, and E is a 6-membered carbocyclic ring wherein the E ring hydrogen bond acceptor is an E ring alkene bond or is selected from the group consisting of keto, cyano, acyl, =CHX$_1$, —OX$_2$, —C(O)X$_2$, epoxide, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl. When the E ring hydrogen bond acceptor comprises an epoxide ring, the epoxide ring comprises two carbon atoms of the E ring, each in the alpha position relative to each other, and an oxygen atom.

In another embodiment of the present invention, the compounds correspond to Formula (B)

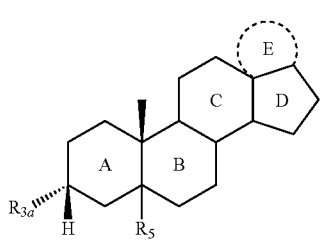

wherein
$R_{3a}$ is hydroxyl or carboxyl;
$R_5$ is α- or β-hydrogen; and
E is as previously defined for any of the above embodiments.

In yet another embodiment, the compounds of the present invention correspond to Formula (C)

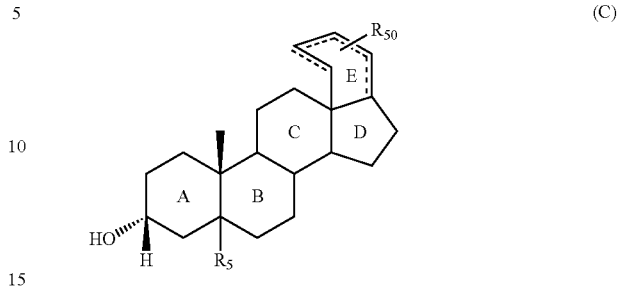

wherein
$R_5$ is α- or β-hydrogen;
$R_{50}$ is selected from the group consisting of hydrogen, keto, cyano, acyl, =CHX$_1$, —OX$_2$, —C(O)X$_2$ and an epoxide; $X_1$ is selected from the group consisting of hydrogen, cyano, hydrocarbyl, substituted hydrocarbyl and acyl; $X_2$ is selected from the group consisting of hydrogen, hydrocarbyl, substituted hydrocarbyl, and acyl, provided that when $R_{50}$ is hydrogen, at least one pair of E ring atoms share a double bond; and E is a 6-membered carbocyclic ring wherein the dashed lines represent optional double bonds provided E comprises no more than 2 double bonds and provided each carbon ring atom of E is sp$^2$ or sp$^3$ hybridized.

In one embodiment where the compounds correspond to Formula (C) and the E ring is in the β-configuration in relation to the C and D rings, $R_5$ may be α- or β-hydrogen and the E ring may be saturated or partially unsaturated. While the E ring and $R_5$ may be as defined above for this embodiment, $R_{50}$ is typically selected from the group consisting of hydrogen, keto, cyano, methylene, methoxy, acetyl, =CHCN, and =CHC(O)CH$_3$. In a preferred embodiment, $R_{50}$ is keto, cyano, or =CHCN.

In another embodiment where the compounds correspond to Formula (C), the compound is selected from the group consisting of

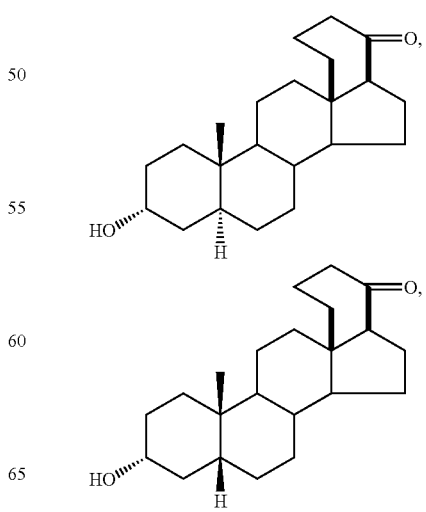

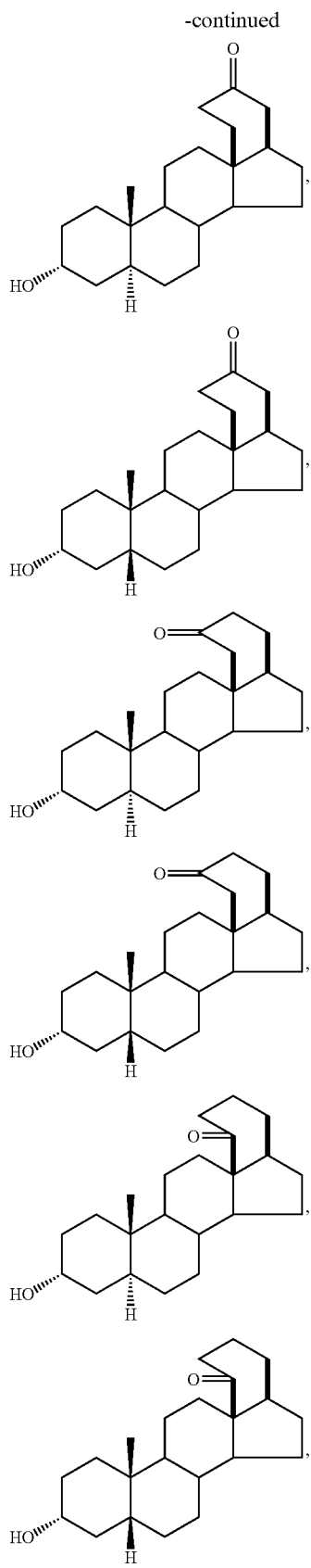
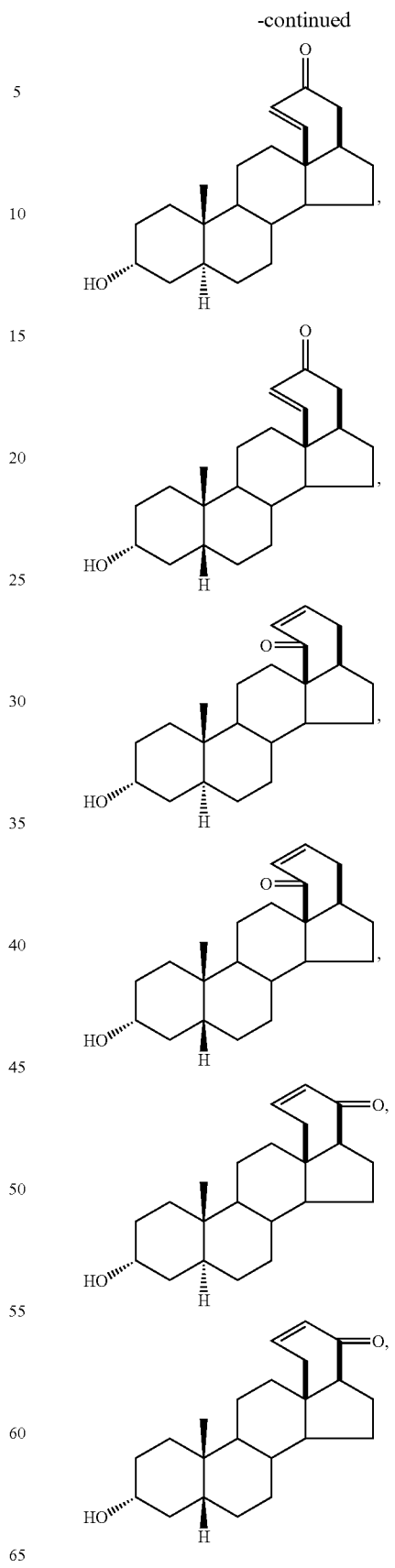

-continued
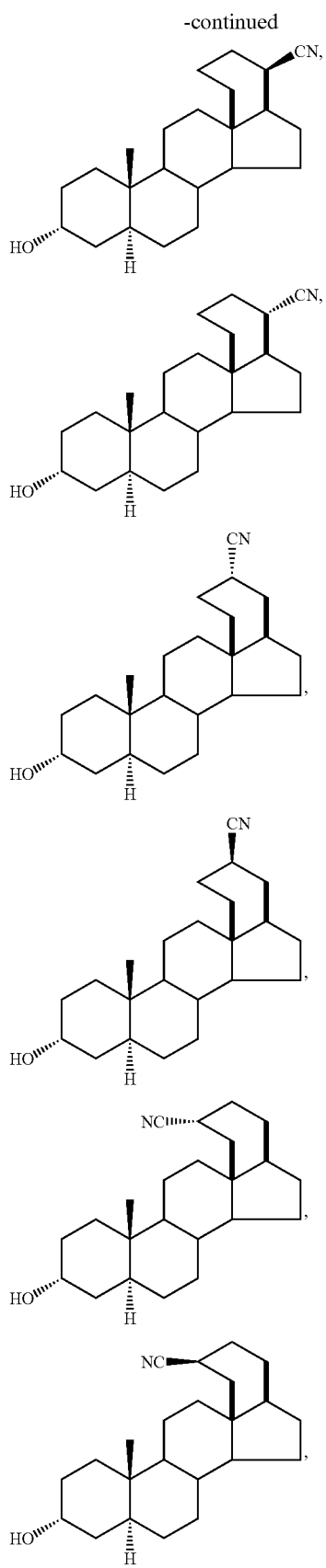
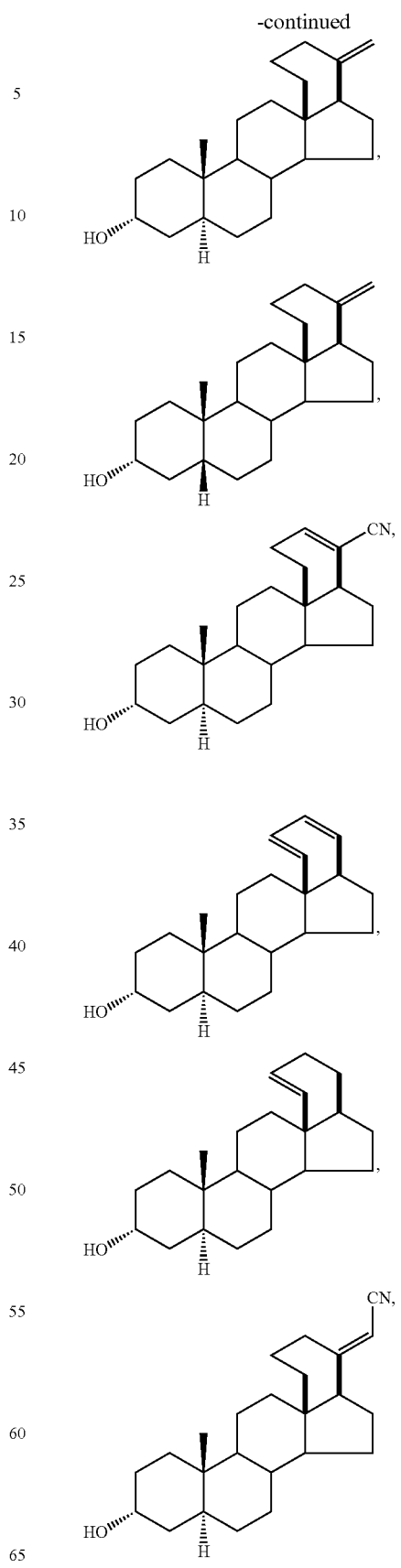

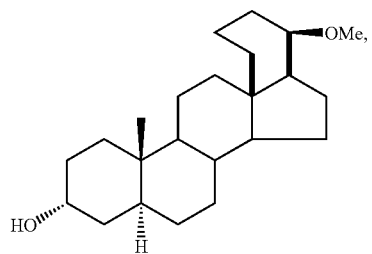
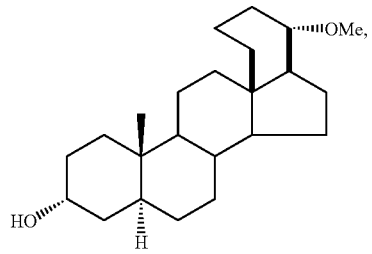
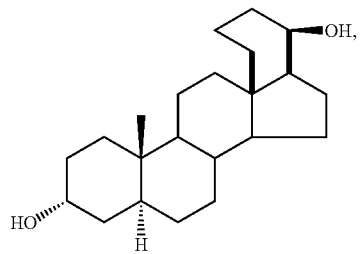
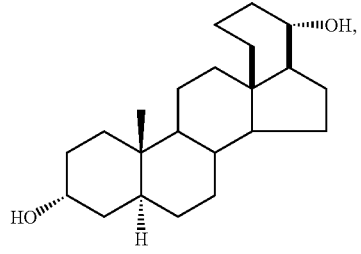
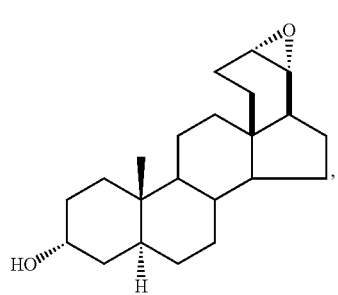
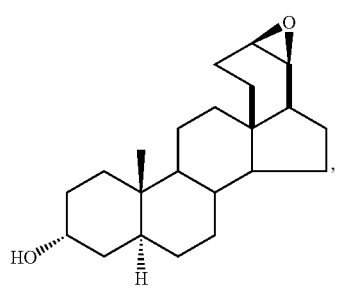
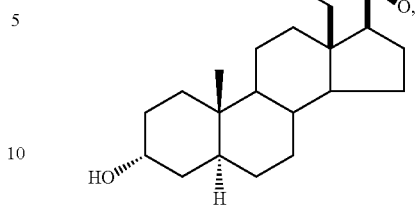
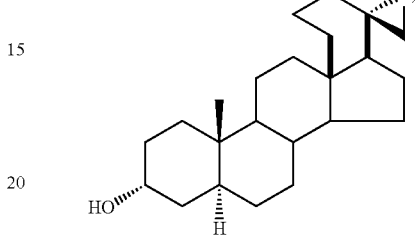
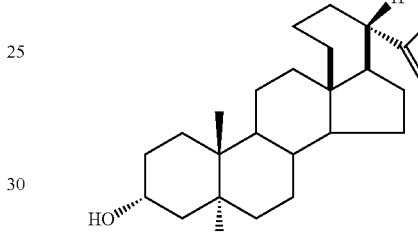
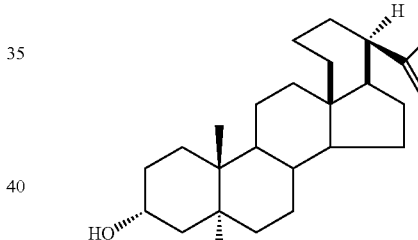
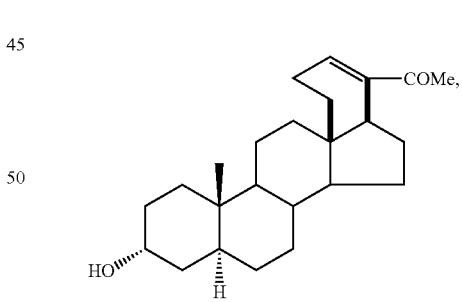
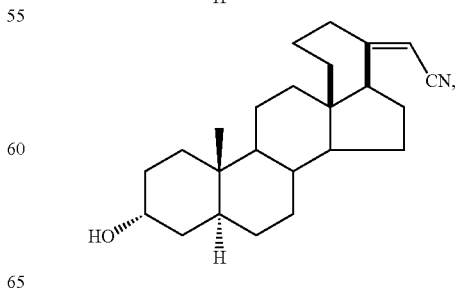

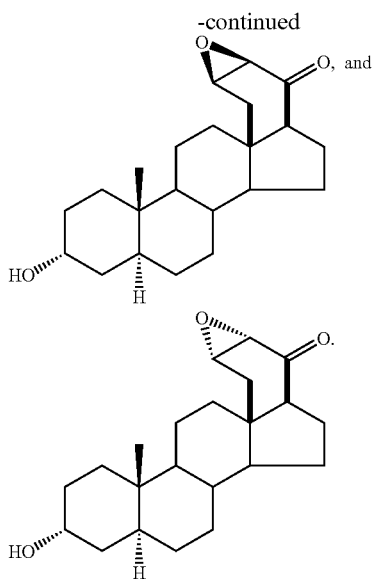

In another embodiment, the compounds of the present invention correspond to Formula (D)

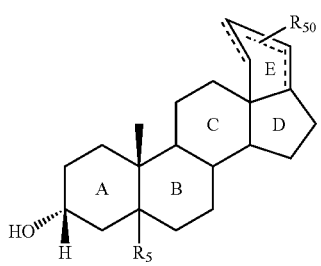

wherein $R_5$ is α- or β-hydrogen;

$R_{50}$ is selected from the group consisting of hydrogen, keto, cyano, acyl, =CHX$_1$, —OX$_2$, —C(O)X$_2$, and an epoxide; where $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl, provided that when $R_{50}$ is hydrogen, at least one pair of E ring atoms share a double bond; and E is a 5-membered carbocyclic ring wherein the dashed lines represent optional double bonds provided E comprises no more than 2 double bonds and each carbon ring atom of E ring is sp$^2$ or sp$^3$ hybridized.

In one embodiment where the compounds correspond to Formula (D), the E ring is in the β-configuration in relation to the C and D rings. In this embodiment, $R_5$ may be α- or β-hydrogen and the E ring may be saturated or partially unsaturated. While the E ring and $R_5$ may be as defined above for this embodiment, $R_{50}$ is typically selected from the group consisting of hydrogen, keto, cyano, methylene, methoxy, acetyl, =CHCN, and =CHC(O)CH$_3$. In a preferred embodiment, $R_{50}$ is =O, CN, or =CHCN.

In another embodiment where the compounds correspond to Formula (D), the compound is selected from the group consisting of

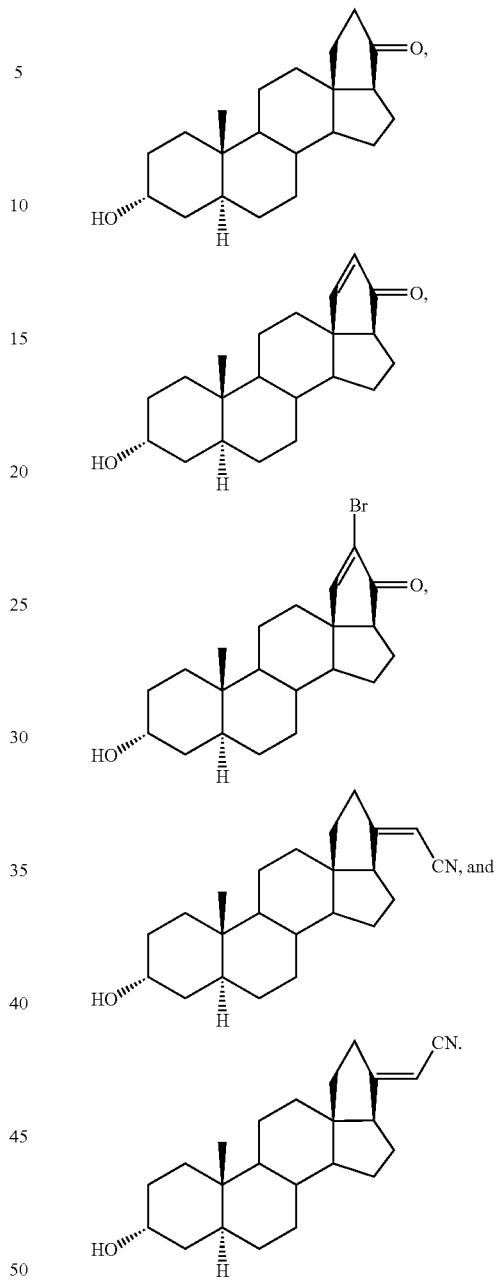

In still another embodiment, the compounds of the present invention are pentacyclic steroids and pentacyclic D-homosteroids comprising:

(i) the tetracyclic steroid ring system, Formula (I) or tetracyclic D-homosteroid ring system, Formula (II), respectively;

(ii) a negatively charged substituent at physiological pH at C(3); and (iii) a fused fifth ring, the fused fifth ring comprising a hydrogen bond acceptor, and (a) in the case of the pentacyclic steroid the C(13) and C(17) carbons, or (b) in the case of the pentacyclic D-homosteroid the C(13) and C(17a) carbons. In this embodiment, the negatively charged substituent at C(3) is typically selected from the group consisting of sulfate, carboxylate, phosphate, phosphonate, and combinations thereof, while rings A, B, C, D, and the fifth fused ring (the "E" ring) and all substituents are as previously defined for any of the above embodiments. In particular, each ring A, B, C, and D may be saturated or, alternatively, at least two of the ring atoms share a double bond. Further, the E ring may be a 5- or 6-membered carbocyclic fully saturated ring or, alternatively, at least one pair of ring atoms of the E ring share a double bond. As described previously for other embodiments, the E ring hydrogen bond acceptor may be selected from the group consisting of keto, cyano, acyl, =$CHX_1$, —$OX_2$, —$C(O)X_2$, epoxide, an E ring alkene bond, and combinations thereof; where $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl. Typically, the E ring hydrogen bond acceptor is selected from the group consisting of keto, cyano, methylene, methoxy, acetyl, =$CHCN$, =$CHC(O)CH_3$, or an E ring alkene bond.

In a preferred embodiment, the compound is a pentacyclic steroid comprising the tetracyclic steroid ring system, Formula (I), wherein each of rings A, B, C, and D of Formula (I) are saturated or, alternatively, at least one pair of ring atoms comprising rings A, B, C, and D of Formula (I) share a double bond, the E ring is a 6-membered carbocyclic ring, the E ring hydrogen bond acceptor is selected from the group consisting of keto, cyano, acyl, =$CHX_1$, —$OX_2$, —$C(O)X_2$, epoxide, an E ring alkene bond, and combinations thereof; where $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl, and the negatively charged substituent at C(3) is a sulfate or carboxylate group.

Steroids having the general Formula (A) may be obtained by the methods described in the examples. The starting material for the compounds of Formula (A) may be obtained using the reaction conditions set forth in Example 1 or a similar process. Generally, cyanoketone (compound 8a of Example 1) was prepared from the 20-ketosteroid 6a (Example 1) in two steps (40%). The 20-keto group was then protected with ethylene glycol to give compound 9a (83%), and this compound was reacted with DIBALH in toluene at room temperature to yield aldehyde 10a. As described for the preparation of a different 13,24-cyclo-18,21-dinorchol-22-en-20-one, treatment of aldehyde 10a with aqueous HCl removed the ketal protecting group and affected a Robinson annulation to yield the cyclosteroid 11a (57% from steroid 9a). Hydrogenation of the 22-en-20-one 11a gave the 20-one 2a (91%).

The compounds of Formula (A) of the present invention are useful for potentiating GABA at $GABA_A$ receptors thereby inducing anesthesia or treating disorders related to GABA function (i.e., insomnia, mood disorders, convulsive disorders, anxiety or symptoms of ethanol withdrawal) in mammals, including humans, and are preferably administered in the form of a pharmaceutical composition comprising an effective amount of a compound of the instant invention in combination with at least one pharmaceutically or pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic or other untoward reaction when administered to a mammal or human, as appropriate.

The pharmaceutical compositions containing the compounds of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, in: *Remington's Pharmaceutical Science* (A. Gennaro, ed.), Mack Publishing Co., Easton, Pa., (1985), pp.1492-1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

The compositions of the invention for oral administration comprise an effective amount of a compound of the invention in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption.

The compounds of the present invention are also preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30\text{-}60}$ sorbitol poly(oleate)$_{2\text{-}4}$, poly(oxyethylene)$_{15\text{-}20}$ monooleate, poly(oxyethylene)$_{15\text{-}20}$ mono 12-hydroxystearate, and poly(oxyethylene)$_{15\text{-}20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds., )(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia* 24, *The National Formulary* 19, (National Publishing, Philadelphia, Pa., 2000), A. J. Spiegel et al., and *Use of Nonaqueous Solvents in Parenteral Products*, J. of Pharm. Sciences, Vol. 52, No. 10, pp. 917-927 (1963).

Preferred solvents include oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor® EL solution or Cremophor® RH 40 solution). Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional minor components can be included in the compositions of the invention for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 weight % of the total composition, more preferably less than about 5 weight %, and most preferably less than about 0.5 weight % of the total composition. Some components, such as fillers or diluents, can constitute up to 90 wt. % of the total composition, as is well known in the formulation art. Such additives include cryoprotective agents for preventing reprecipitation of the steroid or D-homosteroid, surface active, wetting or emulsifying agents (e.g., lecithin, polysorbate-80, Tween® 80, pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the invention or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present invention should be sufficient to effect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as Cremophor® EL solution, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as Cremophor® EL solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsion, is added to the solution while stirring to form a pharmaceutically acceptable emulsion for parenteral administration to a patient. If desired, such emulsions can be formulated to contain a minimal amount of, or to be free of, ethanol or Cremophor® solution, which are known in the art to cause adverse physiological effects when administered at certain concentrations in parenteral formulations.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as Cremophor® solution, is added to the solution while stirring to form a pharmaceutically acceptable solution for parenteral administration to a patient. If desired, such solutions can be formulated to contain a minimal amount of, or to be free of, ethanol or Cremophor® solution, which are known in the art to cause adverse physiological effects when administered at certain concentrations in parenteral formulations.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

DEFINITIONS

The term "steroid" as used herein describes an organic compound containing in its chemical nucleus the perhydrocyclopentanophenanthrene ring.

The term "D-homosteroid" as used herein describes an organic compound containing in its chemical nucleus the perhydrochrysene ring.

The term "hydrogen bond acceptor" as described herein generally describes a substance that receives hydrogen atoms from another substance, the donor. Examples of hydrogen bond acceptors include, but are not limited to the following: halogens, =O, CN, =CHCN, =CH, =CHC(O)CH$_3$, acyl, =CHX$_1$, —OX$_2$ and an epoxide, where X$_1$ is selected from the group consisting of hydrogen, cyano, hydrocarbyl, substituted hydrocarbyl and acyl, and X$_2$ is selected from the group consisting of hydrogen, hydrocarbyl, substituted hydrocarbyl, and acyl. A sp$^2$ hybridized carbon atom may also function as a hydrogen bond acceptor.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

A "carboxyl" moiety as described herein is composed of a carbonyl group and a hydroxyl group bonded to a carbon atom, commonly shown as COOH or CO$_2$H.

The term "acyl," as used herein alone or as part of another group, denotes the moiety formed by removal of the hydroxyl group from the —COOH group of an organic carboxylic acid, e.g., RC(O)— wherein R is R$_a$, R$_a$O—, R$_a$S—, or R$_a$R$_b$N—, R$_a$ and R$_b$ are independently hydrogen, hydrocarbyl, substituted hydrocarbyl, or heterocyclo and "–" denotes the point of attachment.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

An "epoxide" moiety as described herein is an organic compound containing a reactive resulting from the union of an oxygen atom with two other atoms (usually carbon) that are joined in some other way.

As used herein, "Ac" means acetyl; "THF" means tetrahydrofuran, "NNHTs" means tosylhydrazone, "MOM" means methoxymethyl; "DMF" means dimethyl formamide, "DMSO" means dimethyl sulfoxide, "KHMDS" means potassium hexamethyldisilazane, "DBU" means 1,8-diazabicyclo[5.4.0]undec-7-ene; "DIBALH" means diisobutylaluminum hydride, and "HMPA" means hexamethylphosphoramide; "DEAD" means diethyl azodicarboxylate; "PCC" means pyridinium chlorochromate; "m-CPBA" means meta-chloroperbenzoic acid, and "NBS" means N-bromosuccinimide.

The following examples illustrate the invention.

EXAMPLE 1

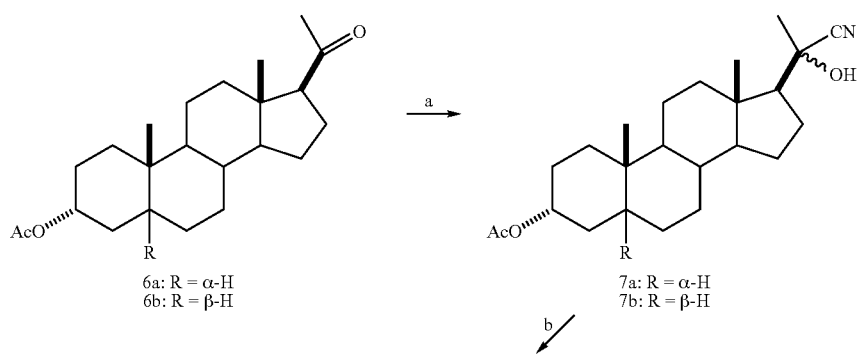

6a: R = α-H
6b: R = β-H

7a: R = α-H
7b: R = β-H

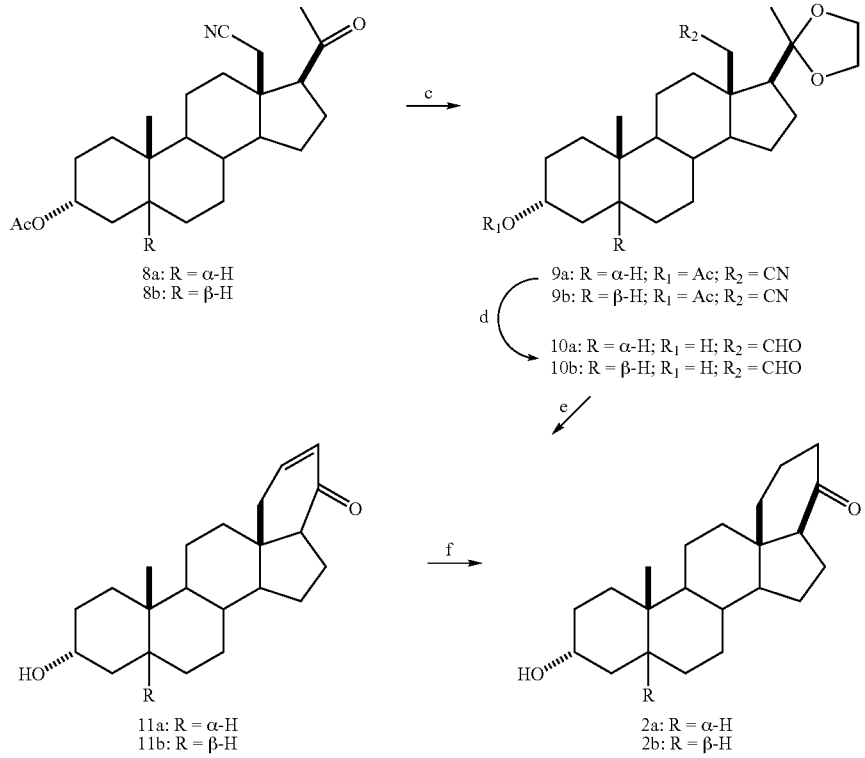
Reagents and conditions: (a) acetone cyanohydrin, Et$_3$N, 50° C. to 25° C.; (b) Pb(OAc)$_4$, CaCO$_3$, I$_2$, cyclohexane, reflux, hv; (c) ethylene glycol, pyridinium p-toluenesulfonate, toluene, reflux; (d) 1 M DIBALH in toluene, THF, −78° C. to 25° C.; (e) 4N aq. HCl, THF, 25° C.; (f) 5% Pd/BaSO$_4$, H$_2$, EtOAc, 40 psi, 25° C.
EXAMPLE 2
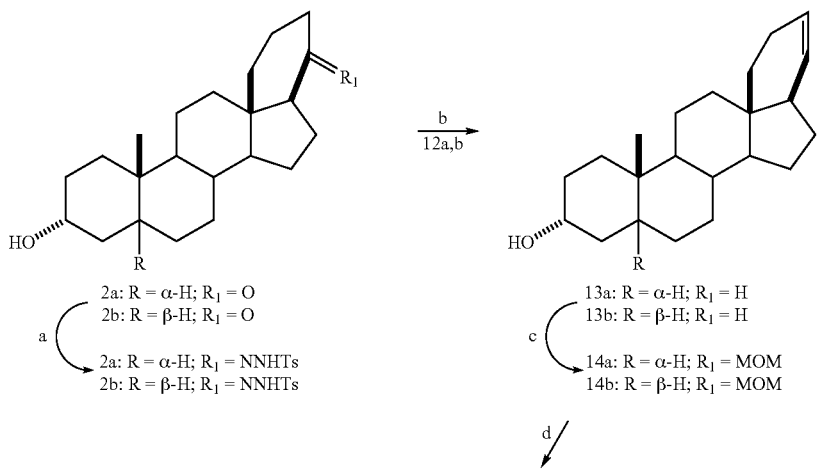

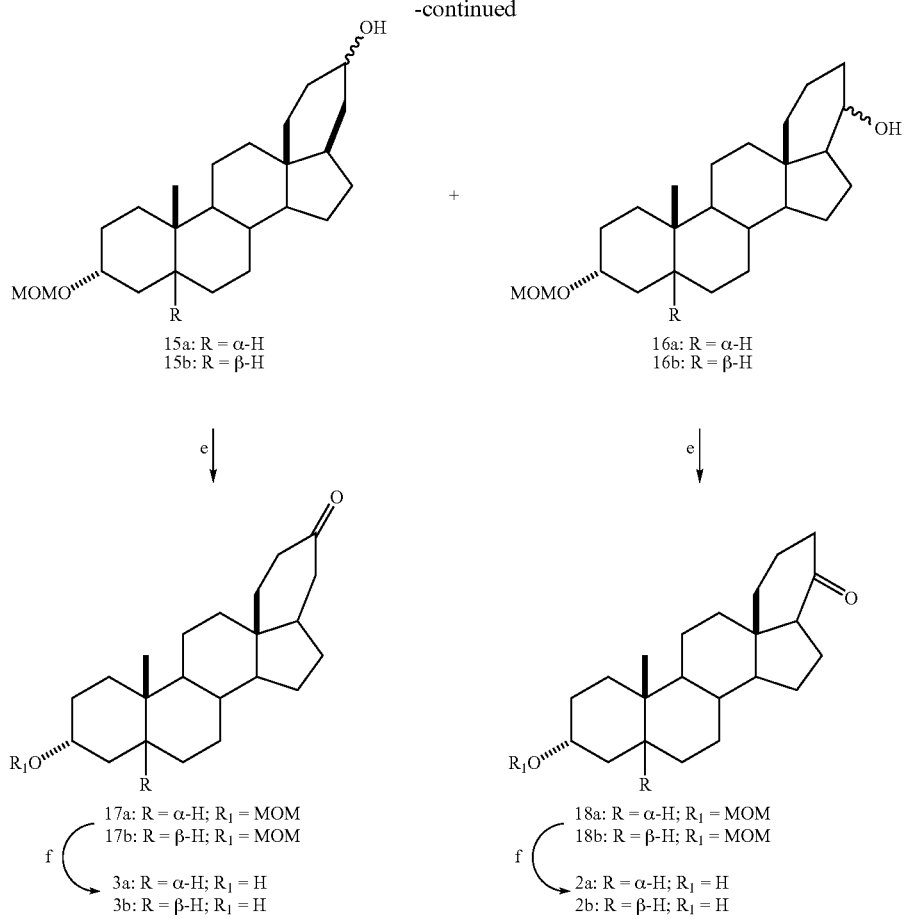
Reagents and conditions: (a) p-toluenesulfonhydrazide, MeOH, conc. $H_2SO_4$, 25° C.; (b) 2.5 N n-BuLi in hexanes, THF, 0° C. to 25° C.; (c) MOMCl, (i-Pr)$_2$NEt, $CH_2Cl_2$, 25° C.; (d) i) 1 M $BH_3$ in THF, 0° C. to 25° C.; ii) aq. NaOH, 30% $H_2O_2$, 0° C. to 25° C.; (e) pyridinium chlorochromate, NaOAc, $CH_2Cl_2$, 25° C.; (f) 37% aq. HCl, MeOH, 25° C.
EXAMPLE 3
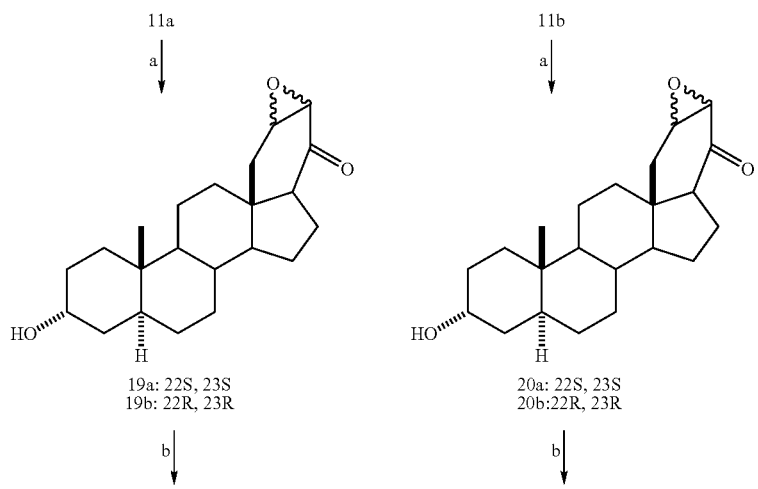

-continued
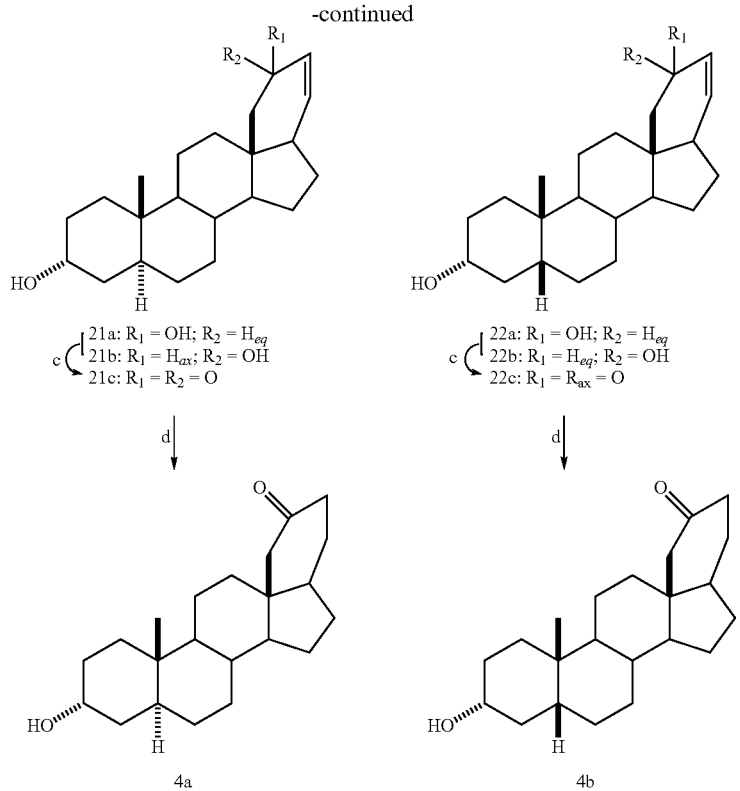
21a: $R_1$ = OH; $R_2$ = $H_{eq}$
21b: $R_1$ = $H_{ax}$; $R_2$ = OH
21c: $R_1$ = $R_2$ = O
22a: $R_1$ = OH; $R_2$ = $H_{eq}$
22b: $R_1$ = $H_{eq}$; $R_2$ = OH
22c: $R_1$ = $R_{ax}$ = O
Reagents and conditions: (a) 30% $H_2O_2$, aq. NaOH, MeOH/1,4-dioxane, 0° C.; (b) $NH_2NH_2 \cdot xH_2O$ (x~1.5), AcOH, MeOH, reflux; (c) $MnO_2$, $CHCl_3$, 25° C.; (d) 5% Pd/BaSO$_4$, MeOH, 40 psi, 25° C.
EXAMPLE 4
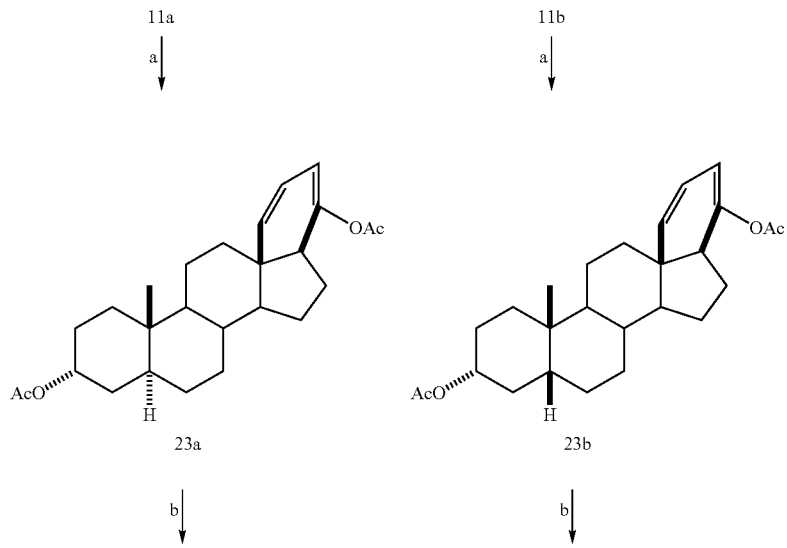

-continued
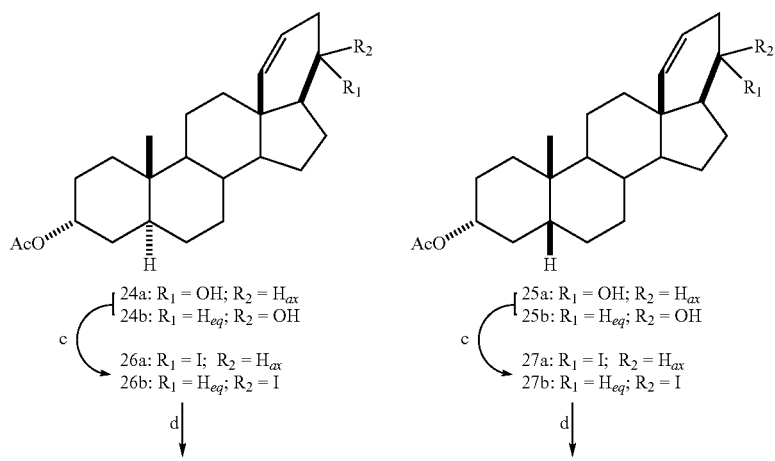
24a: R₁ = OH; R₂ = H$_{ax}$
24b: R₁ = H$_{eq}$; R₂ = OH
26a: R₁ = I; R₂ = H$_{ax}$
26b: R₁ = H$_{eq}$; R₂ = I
25a: R₁ = OH; R₂ = H$_{ax}$
25b: R₁ = H$_{eq}$; R₂ = OH
27a: R₁ = I; R₂ = H$_{ax}$
27b: R₁ = H$_{eq}$; R₂ = I
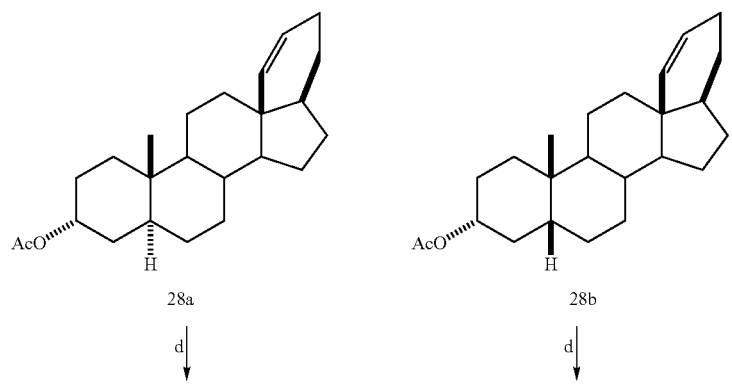
28a
28b
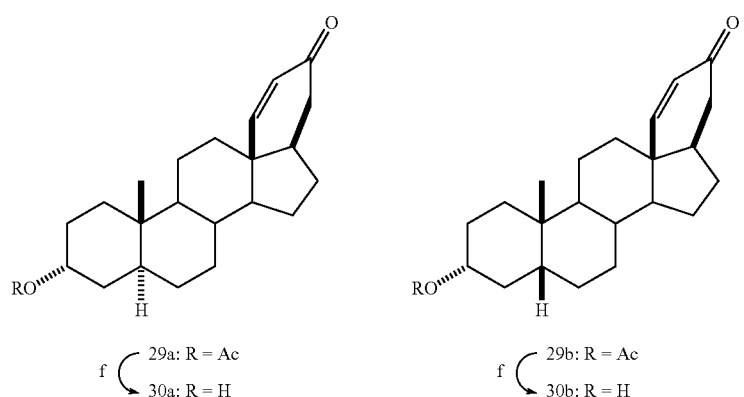
29a: R = Ac
30a: R = H
29b: R = Ac
30b: R = H Reagents and conditions: (a) NaI, Ac$_2$O, Me$_3$SiCl, 0° C. to 25° C.; (b) NaBH$_4$, EtOH, 25° C.; (c) Ph$_3$P, I$_2$, imidazole, toluene, 95° C.; (d) SmI$_2$, HMPA, i-PrOH, THF, 25° C.; (e) CrO$_3$, 3,5-dimethyl pyrazole, CH$_2$Cl$_2$, 25° C.; (f) aq. NaOH, MeOH, reflux.
EXAMPLE 5
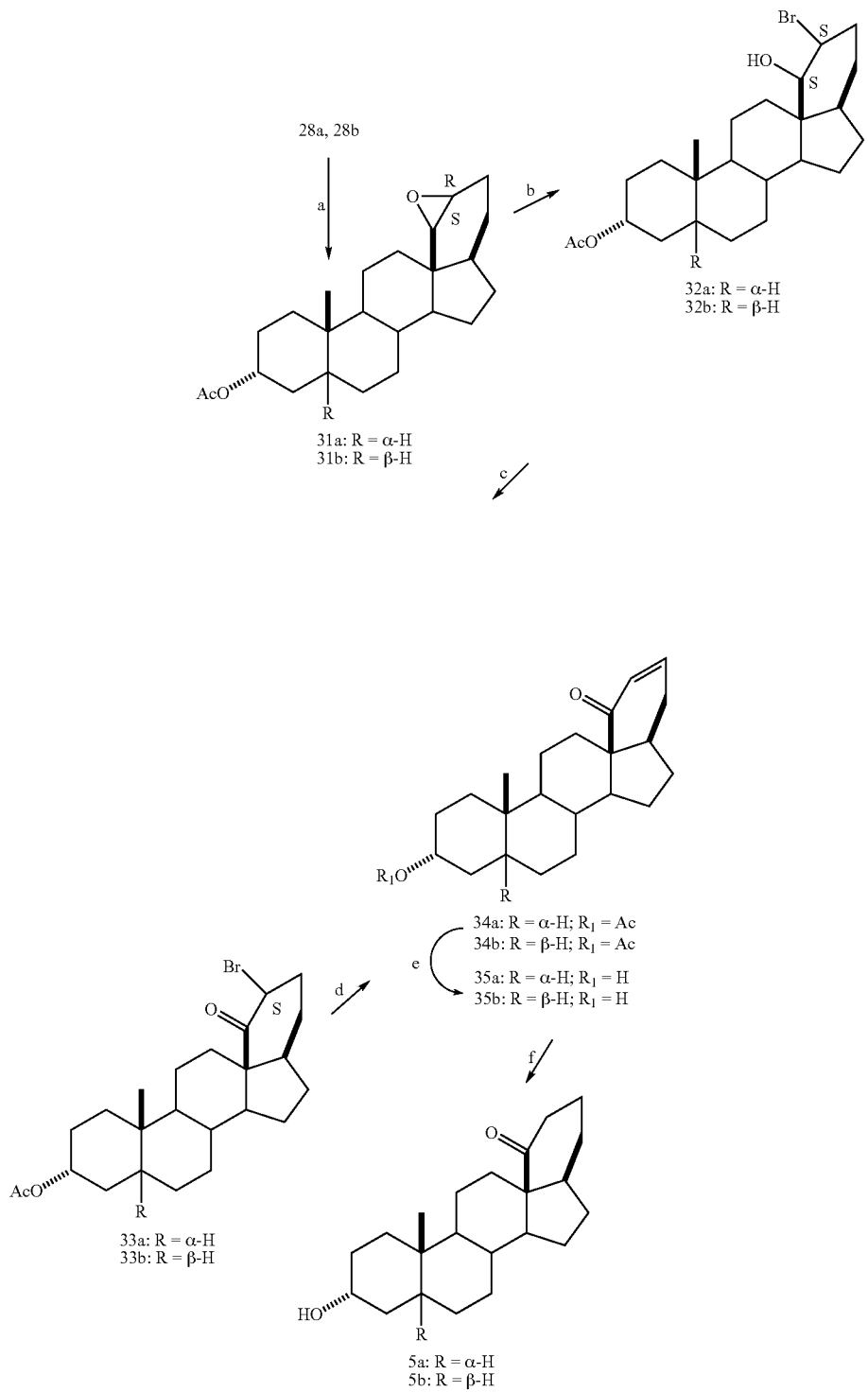

Reagents and conditions: (a) m-chloroperbenzoic acid, NaHCO$_3$, CH$_2$Cl$_2$, 25° C.; (b) 48% aq. HBr, MeCN, −40° C. to 25° C.; (c) Jones reagent, Me$_2$CO, 5° C.; (d) Li$_2$CO$_3$, LiBr, DMF, 125° C.; (e) aq. NaOH, MeOH, reflux; (f) 5% Pd/BaSO$_4$, EtOAc, 40 psi, 25° C.

EXAMPLE 6

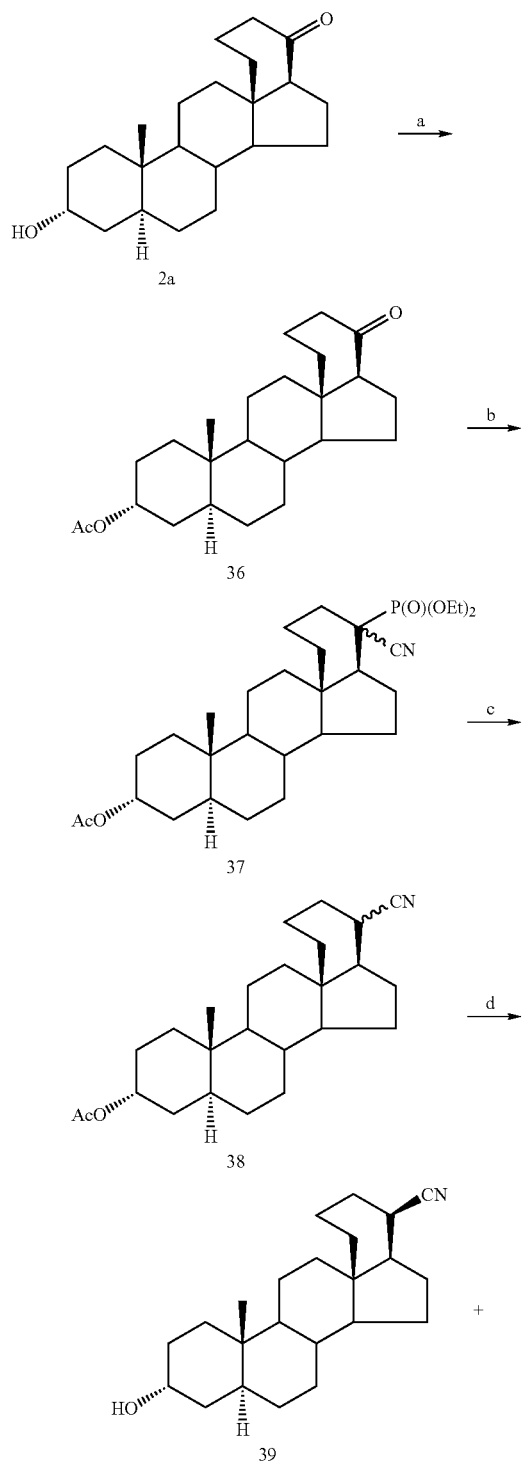

-continued

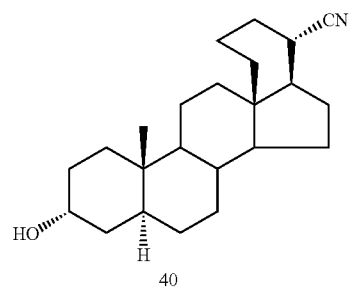

Reagents and conditions: (a) Ac$_2$O, pyridine, room temperature; (b) diethyl cyanophosphonate, LiCN in DMF, THF, room temperature; (c) SmI$_2$, MeOH, THF, room temperature; (d) NaOH, MeOH, room temperature.

EXAMPLE 7

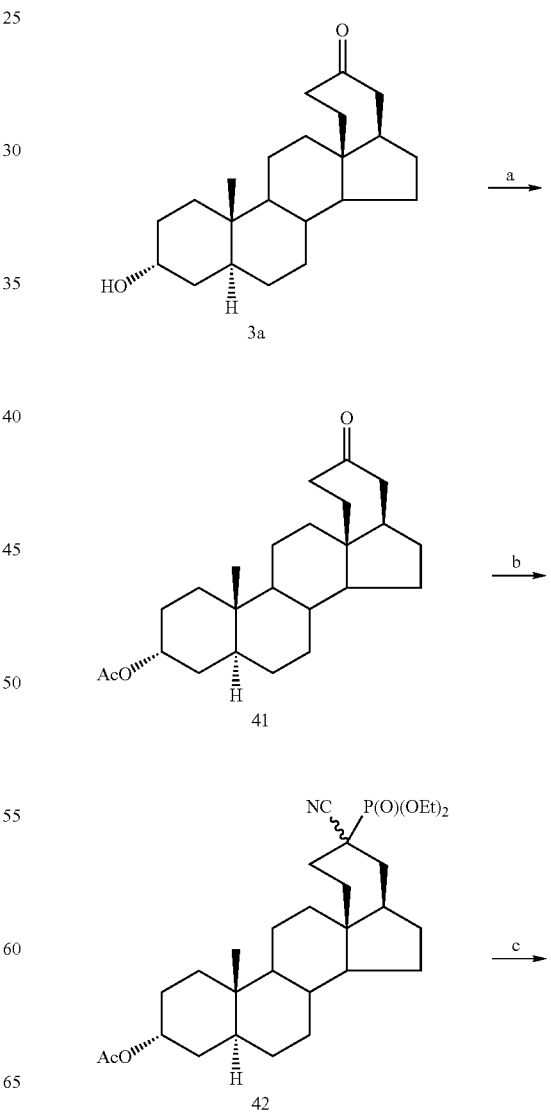

-continued
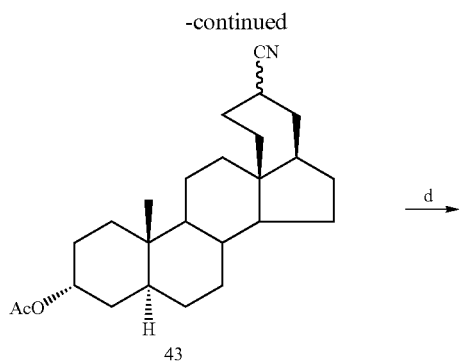
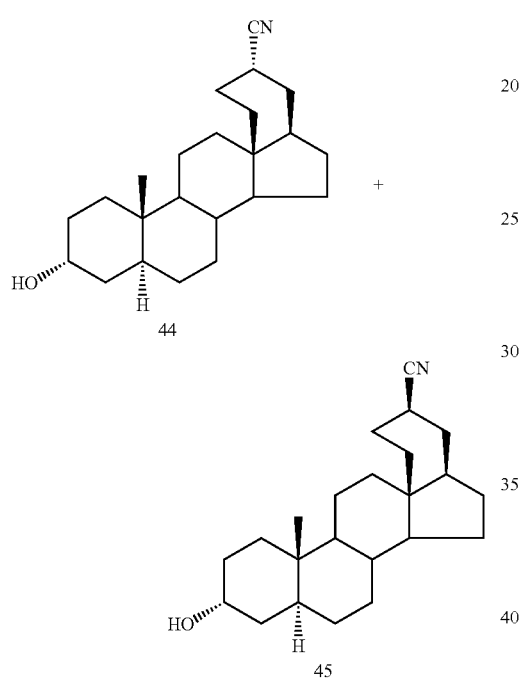
Reagents and conditions: (a) Ac$_2$O, pyridine, room temperature; (b) diethyl cyanophosphonate, LiCN in DMF, THF, room temperature; (c) SmI$_2$, MeOH, THF, room temperature; (d) NaOH, MeOH, room temperature.
EXAMPLE 8
-continued
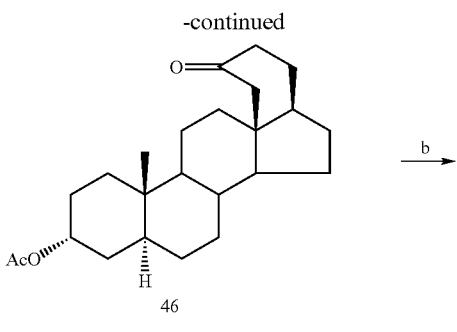
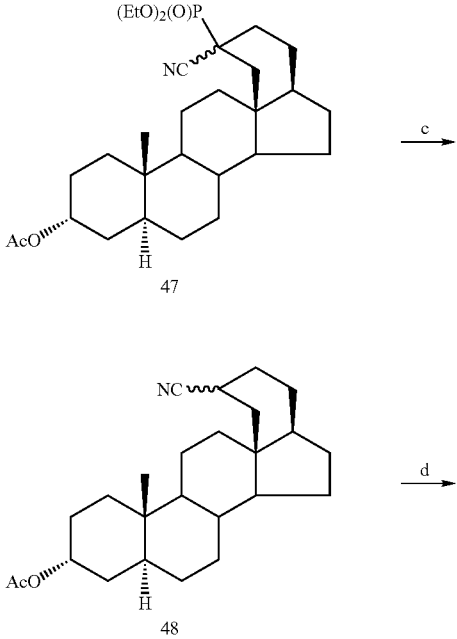
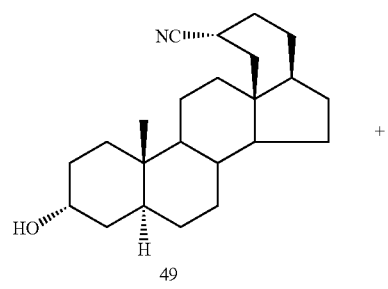
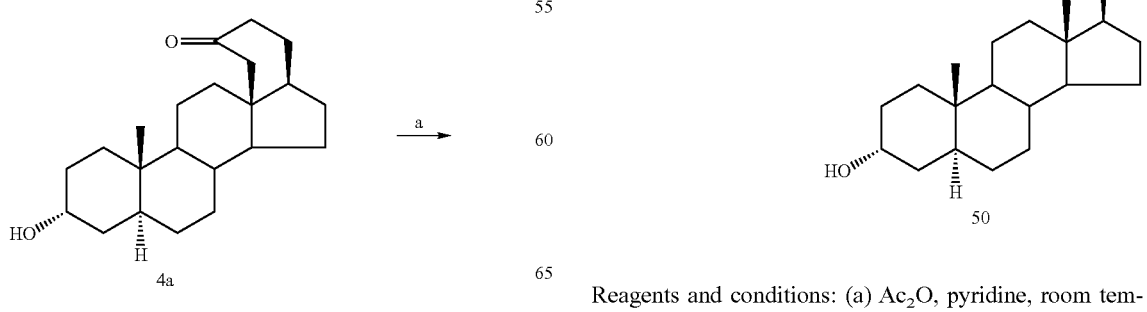
Reagents and conditions: (a) Ac$_2$O, pyridine, room temperature; (b) diethyl cyanophosphonate, LiCN in DMF, THF, room temperature; (c) SmI$_2$, MeOH, THF, room temperature; (d) NaOH, MeOH, room temperature.
EXAMPLE 9
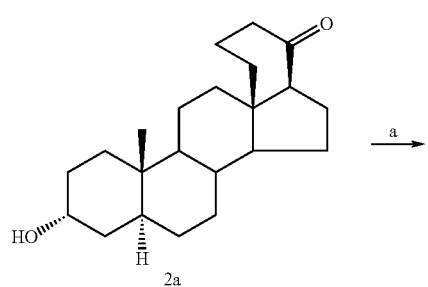
Reagents and conditions: (a) NaH, methyltriphenylphosphonium bromide, DMSO, 70° C.
EXAMPLE 10
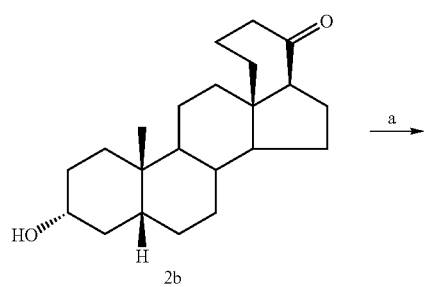
Reagents and conditions: (a) NaH, methyltriphenylphosphonium bromide, DMSO, 70° C.
EXAMPLE 11
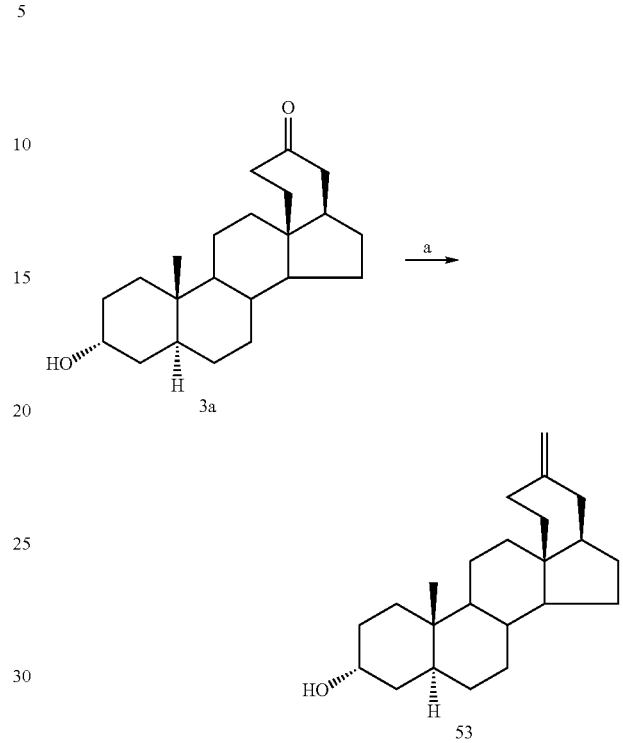
Reagents and conditions: (a) NaH, methyltriphenylphosphonium bromide, DMSO, 70° C.
EXAMPLE 12
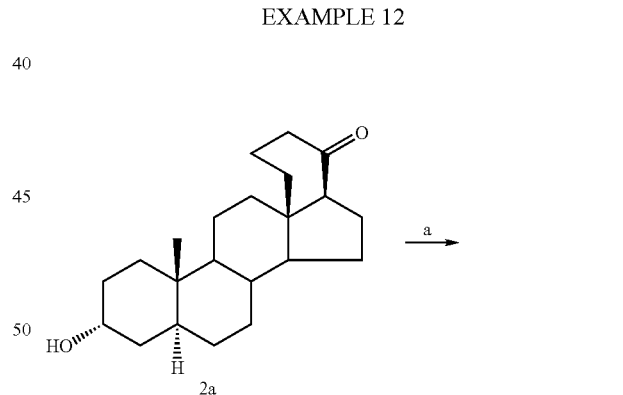
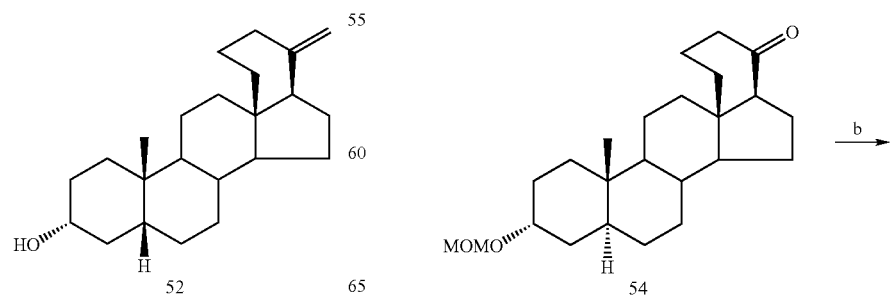

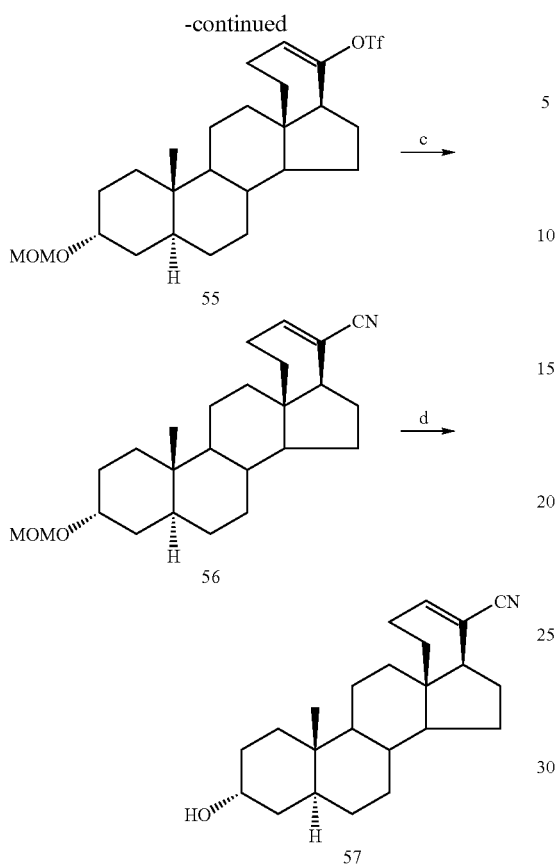

Reagents and conditions: (a) MOMCl, N,N-diisopropyl ethylamine, CH$_2$Cl$_2$, room temperature; (b) N-phenyltrifluoromethane sulfonamide, KHMDS, THF, −78° C. to room temperature; (c) Et$_3$N, Me$_3$SiCN, Pd(PPh$_3$)$_4$, benzene, reflux; (d) HCl, MeOH, CH$_2$Cl$_2$, room temperature.

EXAMPLE 13

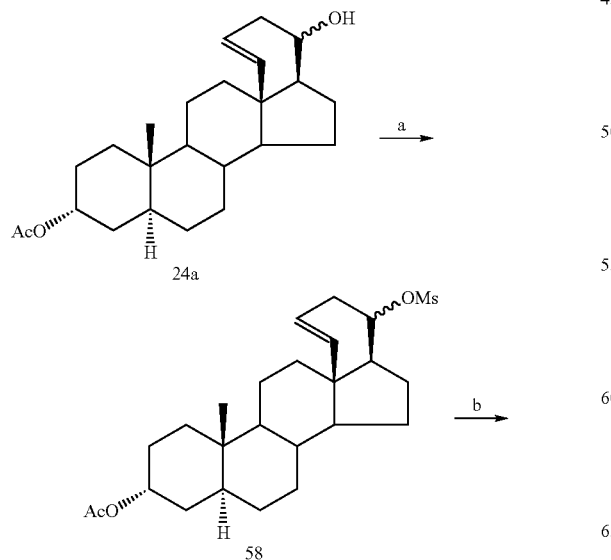

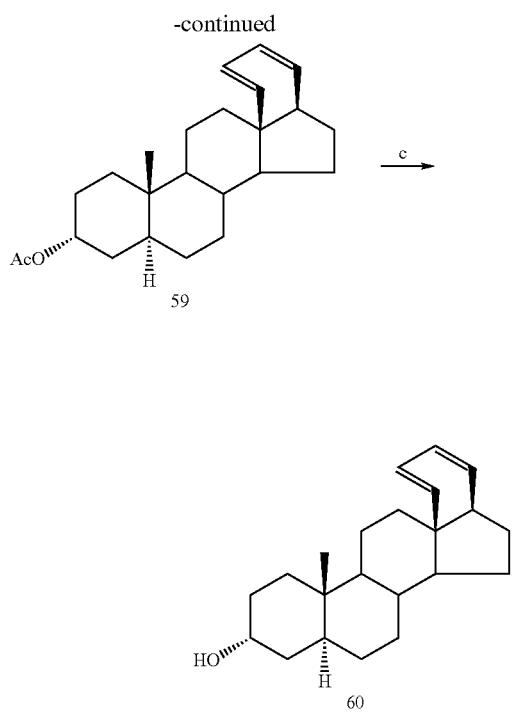

Reagents and conditions: (a) MsCl, Et$_3$N, CH$_2$Cl$_2$, 0° C. room temperature; (b) DBU, toluene, reflux; (c) LiAlH$_4$, THF, room temperature.

EXAMPLE 14

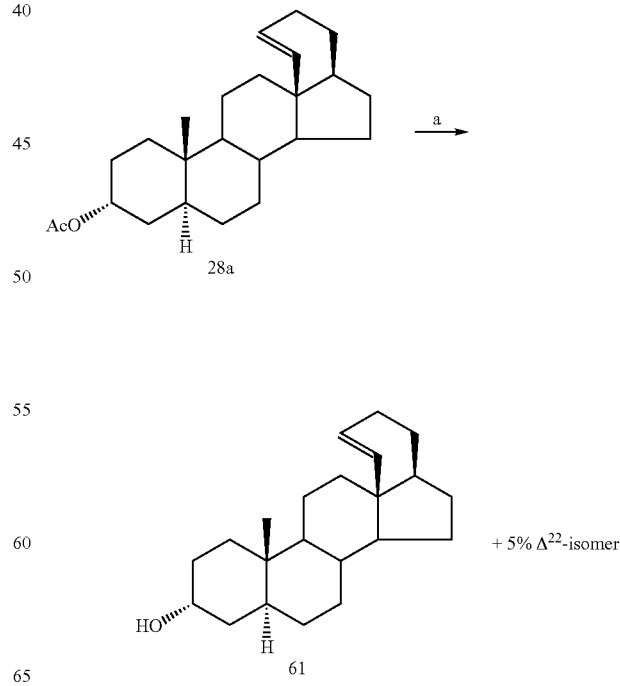

Reagents and conditions: (a) LiAlH₄, THF, room temperature.
EXAMPLE 15
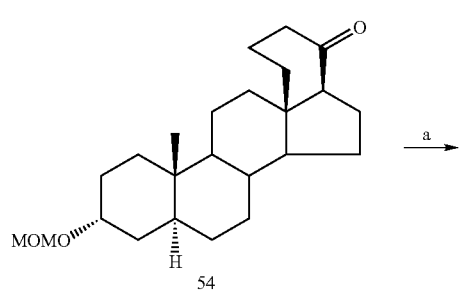
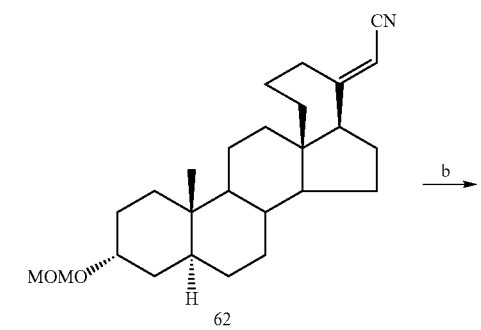
Reagents and conditions: (a) (triphenylphosphoranylidene)acetonitrile; (b) HCl, MeOH, CH₂Cl₂, room temperature.
EXAMPLE 16
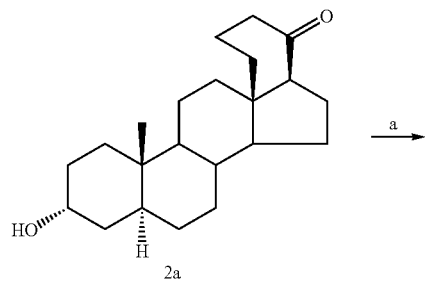
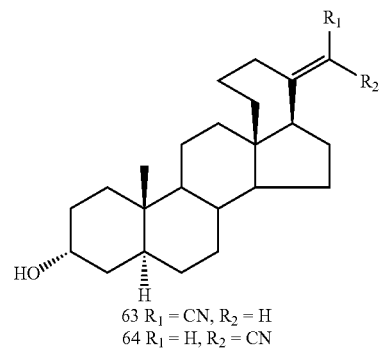
63 R₁ = CN, R₂ = H
64 R₁ = H, R₂ = CN
Reagents and conditions: (a) NaH, CNCH₂P(O)(OEt)₂, THF, reflux.
EXAMPLE 17
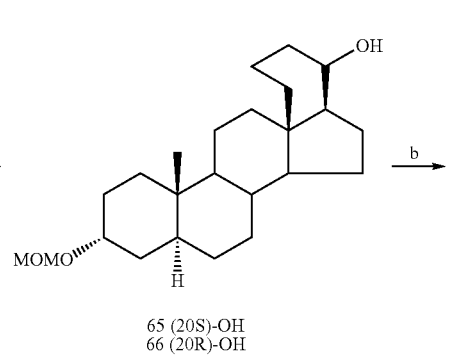
65 (20S)-OH
66 (20R)-OH
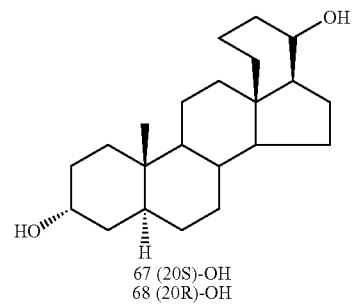
67 (20S)-OH
68 (20R)-OH Reagents and conditions: (a) NaBH$_4$, EtOH, 25° C.; (b) HCl, MeOH—H$_2$O, 25° C.
EXAMPLE 18
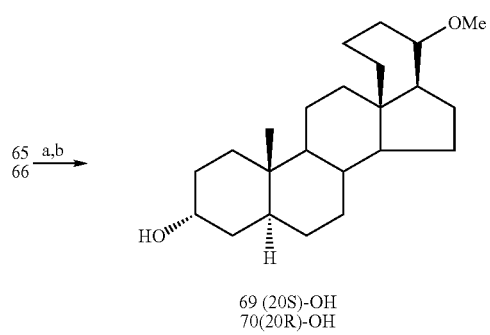
65 →(a,b) 66
69 (20S)-OH
70 (20R)-OH
Reagents and conditions: (a) NaH, MeI, THF, reflux; (b) HCl, MeOH—H$_2$O, 25° C.
EXAMPLE 19
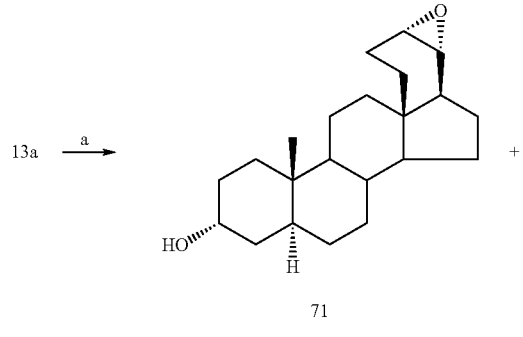
13a →(a)
71
72
Reagents and conditions: (a) m-CPBA, NaHCO$_3$, CH$_2$Cl$_2$, 25° C.
EXAMPLE 20
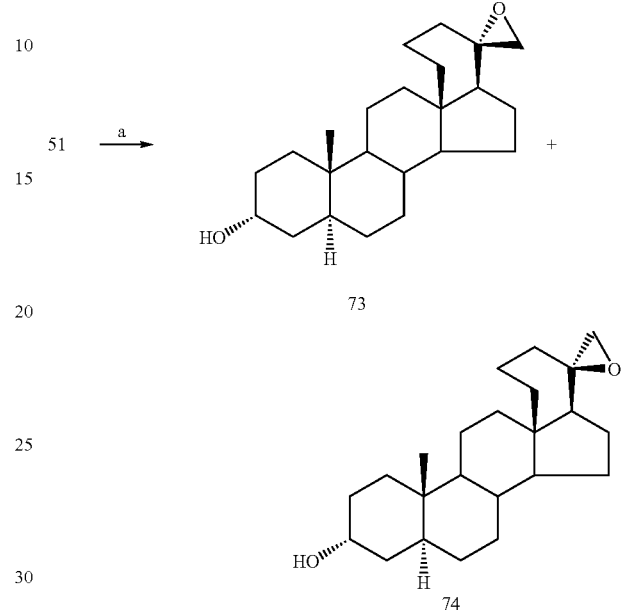
51 →(a)
73
74
Reagents and conditions: (a) m-CPBA, NaHCO$_3$, CH$_2$Cl$_2$, 25° C.
EXAMPLE 21
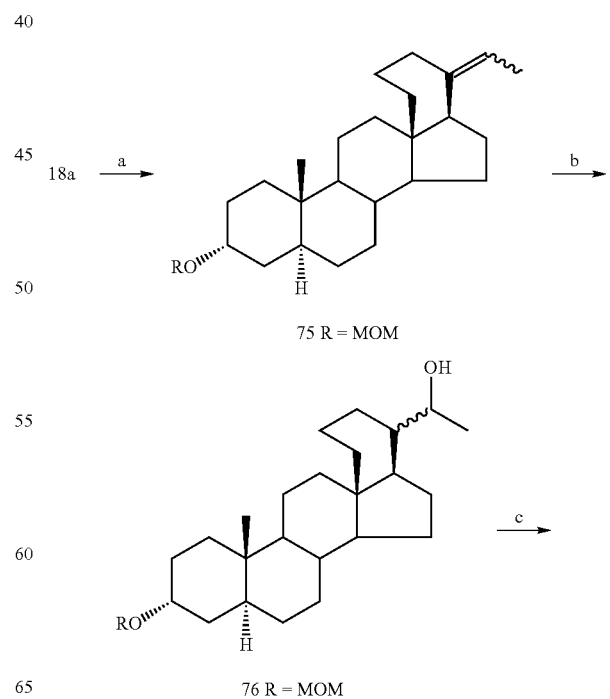
18a →(a) →(b)
75 R = MOM
76 R = MOM
→(c)

EXAMPLE 22
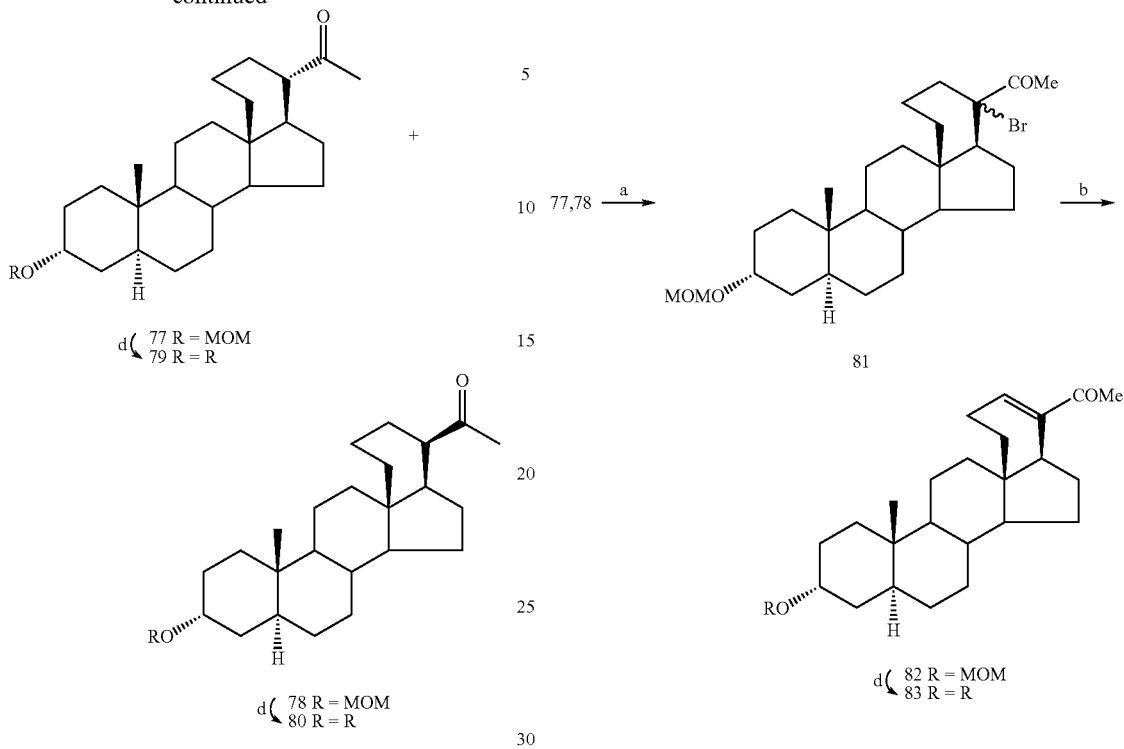
Reagents and conditions: (a) KOBu$^t$, ethyltriphenylphosphonium bromide, THF, reflux; (b) i) BH$_3$, THF, 0° C. to 25° C.; ii) aq. NaOH, 30% H$_2$O$_2$, 0° C. to 25° C.; (c) PCC, NaOAc, CH$_2$Cl$_2$, 25° C.; (d) LiBF$_4$, MeCN, H$_2$O, reflux.
Reagents and conditions: (a) NBS, CCl$_4$, hv, reflux; (b) LiCO$_3$, LiBr, DMF, 130° C.; (c) HCl, MeOH—H$_2$O, 25° C.
EXAMPLE 23
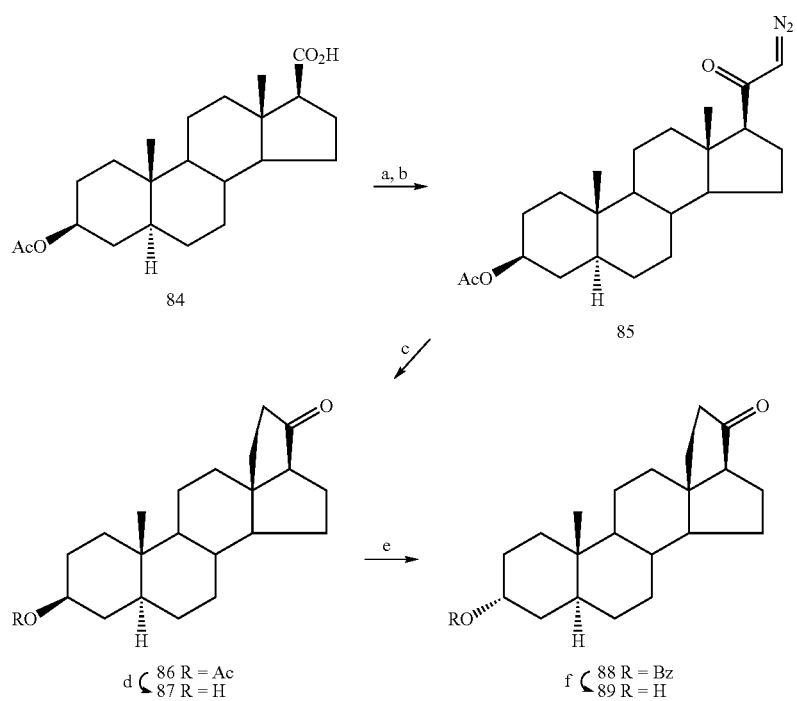

Reagents and conditions: (a) oxalyl chloride, benzene, 25° C.; (b) diazomethane, ether, 0° C. to 25° C.; (c) Rh$_2$(OCOCF$_3$)$_4$, CH$_2$Cl$_2$, 25° C.; (d) NaOH, MeOH—H$_2$O, reflux; (e) PhCO$_2$H, Ph$_3$P, DEAD, THF, 25° C.; (f) NaOH, EtOH—H$_2$O, reflux.

Reagents and conditions: (a) NaH, CNCH$_2$P(O)(OEt)$_2$, THF, reflux.

Experimental Section for Examples 1-25

General Methods. Melting points were determined on a Kofler micro hot stage and are uncorrected. NMR spectra were recorded in CDCl$_3$ at 300 MHz ($^1$H) or 75 MHz ($^{13}$C).

EXAMPLE 24

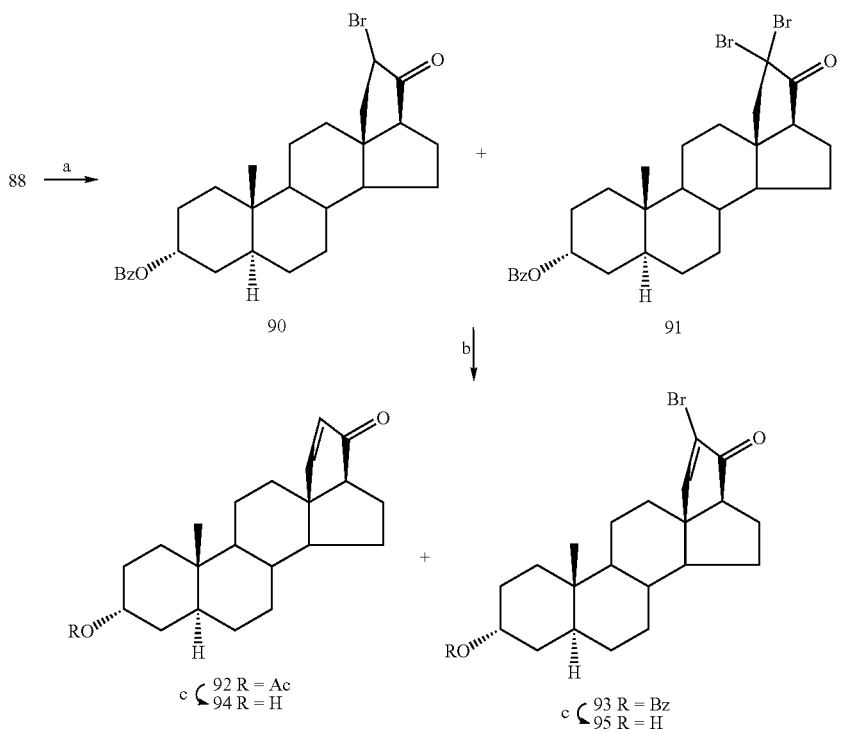

Reagents and conditions: (a) pyridinium tribromide, THF, 25° C.; (b) Li$_2$CO$_3$, LiBr, DMF, 130° C.; (c) NaOH, EtOH—H$_2$O, reflux.

EXAMPLE 25

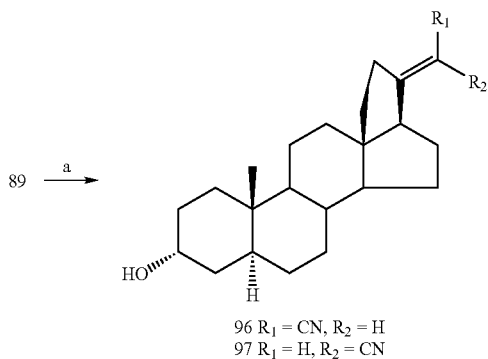

IR spectra were recorded as films on a NaCl plate. Elemental analyses were carried out by M-H-W Laboratories, Phoenix, Ariz. Solvents were used either as purchased or dried and purified by standard methodology. Flash chromatography was performed using silica gel (32-63 μm) purchased from Scientific Adsorbents, Atlanta, Ga.

As set forth in Example 1, compounds 11a, 11b, 2a, and 2b may be prepared by first adding a cyano group at C(20) of (3α,5α)- or (3α,5β)-(3-acetyloxy)pregnan-20-one using acetone cyanohydrin. The cyano group at C(20) migrates to C(18) through the use of a free radical initiator, such as Pb(OAc)$_4$. The ketone at C(20) may then be converted to a ketal using any alcohol or 1,2- or 1,3-glycol. The cyano group may then be reduced to form an aldehyde group using a reducing agent, such as DIBALH. To form the carbocyclic E ring, a cyclization reaction may be carried out in acidic conditions (pH≦5.5) forming compounds 11a and 11b. Hydrogenation of these compounds yields compounds 2a and 2b, respectively.

As set forth in Example 2, compounds 3a, 3b, 2a, and 2b may be prepared by first introducing a double bond into the E ring. Depending upon the starting material, the first step may involve converting the oxo group on the E ring to NNHTs using p-toluenesulfonylhydrazine. The NNHTs group, if present, may then be eliminated in the presence of a strong base, such as n-butyllithium, thereby introducing a double bond into the E ring. Alternatively, the elimination may be carried out by converting the compound to the tolyslate sodium salt to eliminate hydrogen. The hydroxyl group at C(3) may then be protected using a protecting group that is stable in acid or base, such as methoxymethyl. Using, for example, diborane, a hydroxyl group may then be introduced in the E ring at positions C(20) or C(22). A mild oxidizing agent may then be used to convert the hydroxyl group to an oxo, while leaving the protecting group at C(3) intact. One example of such an oxidizing agent is pyridinium chlorochromate. Finally, the hydroxyl at C(3) may be deprotected, using almost any acid, yielding compounds 3a, 3b, 2a, and 2b.

As set forth in Example 3, compounds 21c, 22c, 4a and 4b may be prepared using compounds 11a and 11b as starting materials, respectively, by first introducing an epoxide ring into the E ring using a peroxide or peracid, such as hydrogen peroxide. Hydrazine or substituted hydrazine may then be used as part of an elimination reaction to form an unsaturated E ring possessing a hydroxyl group at C(23). Oxidation of the allylic alcohol using an oxidizing agent selective for oxidation of the carbon atoms adjacent to a double bond, such as $MnO_2$, may then proceed yielding compounds 21c and 22c. These compounds may then be converted by catalytic hydrogenation to yield compounds 4a and 4b.

As set forth in Example 4, compounds 30a and 30b may be prepared starting from compounds 11a and 11b, respectively, using isopropenyl acetate and an acid catalyst or sodium iodide, acetic anhydride, and a trialkylsilyl halide to form the dienol acetate. A borohydride, such as sodium borohydride, may then be used to remove the acetate group from the E ring. The alcohol may then be converted to an iodide group using a nucleophilic displacement reaction. After reduction with $SmI_2$, the compounds may be oxidized to introduce an oxo group into the E ring. Finally, a saponification reaction or an acid catalyzed reaction yields compounds 30a and 30b.

As set forth in Example 5, compounds 5a and 5b may be prepared starting from compounds 28a and 28b, respectively, by first forming an epoxide ring using a peroxide, such as m-chloroperbenzoic acid. The epoxide ring may then be opened with HI, HCl, HBr, or HF and the compound subjected to an oxidation reaction using a chromium reagent, such as Jones reagent. The resulting compound may then be subjected to base-catalyzed elimination, acid or base hydrolysis, and hydrogenation to yield compounds 5a and 5b.

As set forth in Example 6, compounds 39 and 40 may be prepared by first acylating the starting compound, 2a, with an acylating agent such as $Ac_2O$. Diethyl cyanophosphate may then be used, followed by $SmI_2$ to form the cyano group at C(20). Finally, the acetate group at C(3) may be removed to form compounds 39 and 40. Compounds 44 and 45 of Example 7 and compounds 49 and 50 of Example 8 may be prepared in the same manner.

As set forth in Example 9, compound 51 is prepared by converting the carbonyl of compound 2a into a double bond using, for example, the Wilting reaction. Compound 52 of Example 10 and compound 53 of Example 11 may be prepared in the same manner.

As set forth in Example 12, compound 57 may be prepared by first protecting the C(3) hydroxyl of compound 2a with a group such as MOM or a silyl group. The carbonyl may then be modified using N-phenyltrifluoromethane sulfonamide. The triflate may then be converted to cyano and, finally, the C(3) hydroxyl group may be deprotected to yield compound 57.

As set forth in Example 13, compound 60 may be prepared by converting the hydroxyl group at C(20) into a leaving group, for example, by treating with MsCl, and then performing an elimination reaction under basic conditions yielding compound 60.

As set forth in Example 14, compound 61 may be prepared by removal of the acetate group at C(3) by hydrolysis or reduction of compound 28a.

As set forth in Example 15, compound 63 may be prepared by subjecting compound 54 to a Wittig reaction using (triphenylphosphoranylidene)acetonitrile and then removing the protecting group at C(3).

As set forth in Example 16, compounds 63 and 64 may be prepared by subjecting compound 2a to a Wittig reaction with (triphenylphosphoranyidene)acetonitrile.

As set forth in Example 17, compounds 67 and 68 may be prepared by reduction of the ketone group of compound 18a using a hydride reducing agent such as sodium borohydride to obtain compounds 65 and 66 and subsequent removal of the methyoxymethyl group by acid catalyzed hydrolysis.

As set forth in Example 18, compounds 69 and 70 are prepared by methylation of the hydroxyl group of compounds 65 and 66 followed by removal of the methoxymethyl group by acid catalyzed hydrolysis.

As set forth in Example 19, compounds 71 and 72 may be prepared by epoxidation of the double bond of compound 13a using a peracid such as meta-chloroperbenzoic acid.

As set forth in Example 20, compounds 73 and 74 may be prepared by epoxidation of the double bond of compound 51 using a peracid such as meta-chloroperbenzoic acid.

As set forth in Example 21, compounds 79 and 80 may be prepared from compound 18a by a Wittig reaction using ethyltriphenylphosphonium bromide to obtain the methyl-substituted olefin 75, hydroboration of the double bond of compound 75 to obtain the hydroxyl group present in compound 76, PCC oxidation of the hydroxyl group of compound 76 to give the ketone group shown in compounds 77 and 78 and removal of the methoxymethyl group by acid catalyzed hydrolysis to obtain compounds 79 and 80.

As set forth in Example 22, compound 83 may be prepared by bromination of a mixture of compounds 77 and 78 using a reagent such as N-bromosuccinimide, elimination of the bromine to form the double bond shown in compound 82 and removal of the methoxymethyl group by acid catalyzed hydrolysis to obtain compound 83.

As set forth in Example 23, compound 89 may be prepared from compound 84 by conversion of the carboxylic acid group to the corresponding acid chloride group and then reaction of this acid chloride with diazomethane to give the known compound 85. Compound 85 is then cyclized using $Rh_2(OCOCF_3)_4$ to give compound 86. The acetate group is hydrolyzed from compound 86 using base catalysis to give compound 87 and the beta configuration of the hydroxyl group in compound 87 is changed using a Mitsunobu reaction that yields compound 88 with a benzoate ester in the alpha configuration. The ester is hydrolyzed from compound 88 using base catalysis to yield compound 89.

As set forth in Example 24, compounds 94 and 95 may be prepared by bromination of compound 88 using a brominating reagent such a pyridinium tribromide to obtain compounds 90 and 91 that are then subjected to an elimination reaction to obtain compounds 92 and 93. Hydrolysis of the benzoate ester of compounds 92 and 93 under conditions of basic catalysis yields compounds 94 and 95.

As set forth in Example 25, compounds 96 and 97 may be prepared by subjecting compound 89 to a Wittig reaction with (triphenylphosphoranyidene)acetonitrile.

In addition, the hydrogen bond accepting groups on the E ring exemplified in Examples 1-25 may be converted into various other hydrogen bond accepting groups such as an epoxide, carboxy, thioester, alcohol, or ether. Generally, an epoxide ring may be formed from conversion of a ketone to the olefin intermediate, followed by treatment with peracid. A carboxy group may be formed from the hydrolysis of a cyano group. The C=ONH$_2$ hydrolyzes to COOH, which, if desired, can then be converted to an ester. A thioester may be formed from the accession from COOH. Ethers may be formed from the alkylation of oxygen.

(3α,5α)-3-(Acetyloxy)-20-hydroxypregnane-20-carbonitrile (7a)

Compound 7a was prepared using a reported procedure. (See, Mickova, R., et al., *Isolation and the Structure of the Product of Cholesterol Biodegradation by the Mutant Mycobacterium sp. CCM* 3529, *Coll. Czech. Chem. Comm.* 1985, 50:1110-1113). Et$_3$N (0.2 mL) was added to (3α,5α)-3-(acetyloxy)pregnan-20-one (6a, 1.0 g, 2.77 mmol) in acetone cyanohydrin (2 mL) at 50° C. The reaction mixture was slowly cooled to room temperature with stirring. After 3 h, water (5 mL) was added to the reaction mixture, and the white solid precipitate (mixture of compound 6a and 7a) was filtered and washed thoroughly with water, then dried under high vacuum at room temperature for 24 h. The precipitate was used without further purification.

An analytical sample of 7a was purified by column chromatography (silica gel; hexanes/EtOAc, 7:1) and obtained as white crystals: mp 192-195° C. (EtOAc-hexanes); $^1$H NMR δ 0.81 (s, 3H, 19-CH$_3$), 1.00 (s, 3H, 18-CH$_3$), 1.62 (s, 3H, 21-CH$_3$), 2.05 (s, 3H, CH$_3$CO$_2$), 5.01 (m, 1H, CHOAc); $^{13}$C NMR δ 11.3, 13.0, 20.5, 21.5, 24.0, 25.0, 26.1, 28.2, 30.6, 31.8, 32.8 (2×C), 34.9, 35.8, 40.0, 40.2, 43.5, 54.1, 55.9, 59.1, 70.1, 71.7, 122.0 (CN), 170.7 (CO$_2$); IR ν$_{max}$ 3389, 2924, 2231, 1701, 1281 cm$^{-1}$. Anal. (C$_{24}$H$_{37}$NO$_3$) C, H, N.

(3α,5α)-3-(Acetyloxy)-20-oxo-pregnane-18-carbonitrile (8a)

Compound 8a was prepared using a reported procedure. (See, Kalvoda, J., et al., *Reactions of Steroid Hypoiodites. VII. 1,4-Shift of the Nitrile Group (18-Cyanopregnanes), Helv. Chim. Acta* 1966, 49: 424-436)12 (1.6 g, 6.30 mmol) was added to a refluxing mixture of Pb(OAc)$_4$ (6.0 g, 13.5 mmol) and CaCO$_3$ (2 g, 20.0 mmol) in cyclohexane (200 mL). The purple solution was refluxed for 1 h and the mixture of compound 6a and 7a obtained in last step [prepared from 6a (1.0 g, 2.77 mmol)] was added. The reaction mixture was refluxed while irradiated with a 300 W tungsten lamp for 3 h and then cooled to room temperature. After filtration, the precipitate was washed thoroughly with ether. The combined filtrate was washed successively with 10% Na$_2$S$_2$O$_3$ and brine, and dried over Na$_2$SO$_4$. Removal of solvent under reduced pressure gave a residue which was purified by column chromatography (silica gel; hexanes/EtOAc, 4:1) to give compound 8a (400 mg, 40% from 6a) and recovered compound 6a (400 mg).

Compound 8a was obtained as a colorless oil: $^1$H NMR δ 0.80 (s, 3H, 19-CH$_3$), 2.06 (s, 3H, CH$_3$CO$_2$), 2.29 (s, 3H, 21-CH$_3$), 2.70 (t, J=9.0 Hz, 1H, CHCOCH$_3$), 5.02 (m, 1H, CHOAc); $^{13}$C NMR δ 11.3, 16.4, 20.6, 21.5, 23.1, 24.0, 26.0, 28.0, 31.6, 32.5, 32.7, 32.7, 35.5, 35.7, 36.0, 39.8, 46.1, 53.7, 56.5, 62.0, 69.8, 118.1 (CN), 170.5 (CO$_2$), 208.7 (CO); IR ν$_{max}$ 2933, 2249, 1732, 1704, 1245 cm$^{-1}$. Anal. (C$_{24}$H$_{35}$NO$_3$) C, H, N.

(3α,5α)-3-(Acetyloxy)-20,20-[1,2-ethanediylbis(oxy)]pregnane-18-carbonitrile (9a)

A mixture of compound 8a (1.93 g, 5.00 mmol), ethylene glycol (3.1 g, 50 mmol) and PPTS (0.64 g, 2.55 mmol, 30% W/W) in toluene (50 mL) was refluxed using a Dean-Stark apparatus under N$_2$ for 2 h. The reaction mixture was cooled to room temperature, washed with 10% NaHCO$_3$ and brine, and dried over Na$_2$SO$_4$. The solvent was removed and the residue was purified by column chromatography (silica gel; hexanes/EtOAc, 9:1) to give compound 9a (1.78 g, 83%).

Compound 9a was obtained as white crystals: mp 176-177° C. (EtOAc-hexanes); $^1$H NMR δ 0.80 (s, 3H, 19-CH$_3$), 1.29 (s, 3H, 21-CH$_3$), 2.05 (s, 3H, CH$_3$CO$_2$), 2.27 (d, J=16.8 Hz, 1H, CH$_2$CN), 2.52 (d, J=16.8 Hz, 1H, CH$_2$CN), 4.04 (m, 4H, OCH$_2$CH$_2$O), 5.01 (m, 1H, CHOAc); $^{13}$C NMR δ 11.2, 16.7, 20.3, 21.4, 23.0, 23.2, 23.4, 25.9, 28.0, 31.4, 32.6 (2×C), 35.0, 35.6, 36.6, 39.7, 43.7, 53.7, 56.0, 56.3, 63.0, 63.7, 69.8, 110.8 (20-C), 119.8 (CN), 170.4 (CO$_2$); IR ν$_{max}$ 2937, 2241, 1730, 1237 cm$^{-1}$. Anal. (C$_{26}$H$_{39}$NO$_4$) C, H, N.

(3α,5α)-20,20-[1,2-Ethanediylbis(oxy)]-3-hydroxypregnane-18-carboxaldehyde (10a)

Compound 9a (2.0 g, 4.66 mmol) in THF (120 mL) was cooled to −78° C. and DIBALH (1.0 M in toluene, 23.3 mL, 23.3 mmol) was added. The colorless solution was stirred at ambient temperature for 26 h and then cooled to 0° C. After H$_2$O (5 mL) was added dropwise to quench the reaction, the solvent was removed at room temperature. EtOAc (50 mL) and H$_2$O (20 mL) were added to the residue. Insoluble Al(OH)$_3$ was filtered through a pad of Celite 545® and washed thoroughly with EtOAc. The combined filtrate was washed with water and dried over Na$_2$SO$_4$. Solvent removal under reduced pressure gave aldehyde 10a as a white solid that was partially characterized and immediately converted into cyclosteroid 11a. Aldehyde 10a had: $^1$H NMR δ 0.77 (s, 3H, 19-CH$_3$), 1.29 (s, 3H, 21-CH$_3$), 3.85 (m, 4H, OCH$_2$CH$_2$O), 4.03 (m, 1H, CHOH), 9.82 (t, J=2.4 Hz, 1H, CHO); $^{13}$C NMR δ 11.1, 20.2, 22.9, 23.4, 23.5, 28.3, 28.9, 31.7, 32.0, 34.8, 35.7, 36.0, 36.3, 39.0, 40.2, 44.1, 54.1, 57.6, 57.7, 62.6, 64.0, 66.2, 111.1 (20-C), 204.9 (CHO).

(3α,5α)-3-Hydroxy-13,24-cyclo-18,21-dinorchol-22-en-20-one (11a)

A solution of aldehyde 10a in THF (100 mL) and aqueous HCl (4 N, 32 mL) was stirred under N$_2$ at room temperature for 16 h. THF was removed under reduced pressure. The residue was extracted with EtOAc. The combined EtOAc extracts were washed with 10% NaHCO$_3$ and brine, and dried over Na$_2$SO$_4$. After solvent removal under reduced pressure, the residue was purified by column chromatography (silica gel; CH$_2$Cl$_2$/EtOAc, 8:1) to give enone 11a (0.86 g, 57% from 9a).

Compound 11a was obtained as white crystals: mp 230-232° C. (EtOAc-hexanes); $^1$H NMR δ 0.79 (s, 3H, 19-CH$_3$), 4.05 (m, 1H, CHOH), 5.96 (dd, J=3.0 Hz, J=9.9 Hz, 1H, CH=CHCO), 6.83 (m, 1H, CH=CHCO); $^{13}$C NMR δ 11.2, 20.3, 25.8, 26.2, 27.2, 28.3, 28.9, 32.0, 32.1, 33.9, 35.3, 35.8, 36.1, 39.0, 47.5, 53.7, 56.3, 57.7, 66.3, 127.4 (CH=CHCO), 148.3 (CH=CHCO), 202.3 (CO); IR ν$_{max}$ 3429, 2924, 1666, 1444 cm$^{-1}$. Anal. (C$_{22}$H$_{32}$O$_2$) C, H.

(3α,5α)-3-Hydroxy-13,24-cyclo-18,21-dinorcholan-20-one (2a)

Enone 11a (328 mg, 1.0 mmol) was dissolved in EtOAc (50 mL) and hydrogenated (40 psi, $H_2$, 5% Pd/BaSO$_4$, 100 mg) for 1.5 h. The reaction mixture was filtered through a pad of Celite 545® to remove catalyst and the solvent was removed under reduced pressure. The product was purified by column chromatography (silica gel; hexanes/EtOAc/CH$_2$Cl$_2$, 6:1:0.3) to give compound 2a (300 mg, 91%) as white crystals: mp 200-202° C. (EtOAc-hexanes); $^1$H NMR δ 0.79 (s, 3H, 19-CH$_3$), 2.50 (m, 1H, CHCO), 4.04 (m, 1H, CHOH); $^{13}$C NMR δ 11.2, 20.3, 22.1 (2×C), 25.1, 27.0, 28.4, 29.0, 32.1, 32.2, 33.5, 35.2, 35.8, 36.1, 37.3, 39.0, 49.6, 53.9, 56.7, 61.5, 66.4, 215.6 (CO); IR $\nu_{max}$ 3548, 2928, 1701, 1253 cm$^{-1}$. Anal. (C$_{22}$H$_{34}$O$_2$) C, H.

(3α,5α)-13,24-Cyclo-18,21-dinorchol-20(22)-en-3-ol (13a)

To the solution of compound 2a (330 mg, 1.0 mmol) and p-toluenesulfonhydrazide (186 mg, 1.0 mmol) in MeOH (40 mL) was added 3 drops of 96% H$_2$SO$_4$. The reaction mixture was stirred at room temperature for 3-4 h and the MeOH was removed under reduced pressure. The residue was dissolved in EtOAc (50 mL) and washed with 10% NaHCO$_3$ and brine, and dried over Na$_2$SO$_4$. After solvent removal, hydrazone 12a was obtained and used without further purification or characterization.

n-BuLi (2.5 M in hexanes, 1.6 mL, 4 mmol) was added dropwise to the solution of hydrazone 12a (obtained from 1.0 mmol ketone 2a) in anhydrous THF (10 mL) under N$_2$ at 0° C. The orange solution was stirred overnight (14 h) at ambient temperature and quenched with water (0.4 mL) at 0° C. EtOAc (50 mL) was added and the mixture was washed with saturated aqueous NH$_4$Cl and brine, and dried over Na$_2$SO$_4$. After solvent removal under reduced pressure, the residue was purified by column chromatography (silica gel; hexanes/EtOAc, 10:1) to give compound 13a (201 mg, 64% from ketone 2a).

Compound 13a was obtained as white crystals: mp 169-170° C. (hexanes); $^1$H NMR δ 0.79 (s, 3H, 19-CH$_3$), 4.04 (m, 1H, CHOH), 5.55 (m, 1H, CH=), 5.76 (m, 1H, CH=); $^{13}$C NMR δ 11.2, 19.8, 20.2, 21.6, 24.7, 28.6, 29.1, 30.6, 32.3 (2×C), 33.2, 34.7, 35.9, 36.2, 39.3, 40.9, 46.6, 54.7, 56.1, 66.6, 124.4 (CH=), 130.9 (CH=); IR $\nu_{max}$ 3307, 3019, 2927, 1430, 1002 cm$^{-1}$. Anal. (C$_{22}$H$_{34}$O) C, H.

(3α,5α)-3-Methoxymethoxy-13,24-cyclo-18,21-dinorchol-20(22)-ene (14a)

Methoxy methylchloride (0.11 mL, 1.5 mmol) was added to compound 13a (158 mg, 0.5 mmol) and N,N-diisopropyl ethylamine (0.44 mL, 5 mmol) in CH$_2$Cl$_2$ (20 mL). The resultant solution was stirred at room temperature for 24 h. The solvent was partially removed and the residue was purified by column chromatography (silica gel; hexanes/EtOAc, 10:1) to give compound 14a (170 mg, 95%) as white crystals: mp 77-78° C. (hexanes); $^1$H NMR δ 0.80 (s, 3H, 19-CH$_3$), 3.37 (s, 3H, CH$_3$O), 3.83 (m, 1H, CHOCH$_2$), 4.66 (m, 2H, OCH$_2$O), 5.56 (m, 1H, CH=), 5.76 (m, 1H, CH=); $^{13}$C NMR δ 11.4, 19.8, 20.2, 21.6, 24.7, 26.4, 28.7, 30.6, 32.3, 32.9, 33.3, 33.7, 34.7, 36.0, 39.9, 40.9, 46.6, 54.7, 55.1, 56.2, 71.7, 94.6 (OCH$_2$O), 124.4 (CH=), 130.9 (CH=); IR $\nu_{max}$ 3016, 2927, 1455, 1043 cm$^{-1}$. Anal. (C$_{24}$H$_{38}$O$_2$) C, H.

(3α,5α)-3-Hydroxy-13,24-cyclo-18,21-dinorcholan-22-one (3a)

BH$_3$ (1.0 M in THF, 1.59 mL, 1.59 mmol) was added to compound 14a (190 mg, 0.53 mmol) in anhydrous THF (20 mL) under N$_2$ at 0° C. The resultant solution was stirred at room temperature for 3.5 h and cooled to 0° C. Water (0.1 mL) was added to quench the reaction followed by aq. NaOH (3N, 3.0 mL) and 30% H$_2$O$_2$ (3.0 mL). The reaction mixture was stirred at ambient temperature for 1.5 h and extracted with CH$_2$Cl$_2$. The combined CH$_2$Cl$_2$ extracts were washed with brine until the pH was neutral and then dried over Na$_2$SO$_4$. After solvent removal under reduced pressure, the residue (a mixture of two pairs of diastereomers of 15a and 16a) was used without further purification or characterization.

NaOAc (130 mg, 1.59 mmol) and PCC (228 mg, 1.06 mmol) were added to the solution of compounds 15a and 16a in CH$_2$Cl$_2$ (30 mL). The reaction mixture was stirred at room temperature for 2 h and Et$_2$O (50 mL) was added. The mixture was filtered through a pad of Celite 545® and washed thoroughly with ether. Solvent was removed from the combined filtrate to give a mixture of ketones 17a and 18a which was dissolved in CH$_3$OH (12 mL). Then, 37% aqueous HCl (4 mL) was added. The solution was stirred at room temperature for 1 h and MeOH was removed under reduced pressure. EtOAc (30 mL) was added to the residue and the solution was washed with water, 10% NaHCO$_3$, brine, and dried over Na$_2$SO$_4$. Solvent removal under reduced pressure gave ketones 3a and 2a which were separated by column chromatography (silica gel; EtOAc/CH$_2$Cl$_2$, 1:15) to give ketone 3a (90 mg, 51% from 14a) and recovered compound 2a (58 mg, 33% from 14a).

Compound 3a was obtained as white crystals: mp 195-197° C. (EtOAc-hexanes); $^1$H NMR δ 0.79 (s, 3H, 19-CH$_3$), 2.39 (m, 1H, CH$_2$CO), 2.54 (dd, J=6.0 Hz, J=14.4 Hz, 1H, CH$_2$CO), 4.05 (m, 1H, CHOH); $^{13}$C NMR δ 11.2, 20.4, 23.3, 23.6, 27.7, 28.4, 29.0, 32.0, 32.2, 32.7, 35.6, 35.8, 36.2, 36.9, 39.1, 41.2, 41.5, 48.9, 54.4, 55.6, 66.4, 213.4 (CO); IR $\nu_{max}$ 3308, 2918, 1712, 1449, 1007 cm$^{-1}$. Anal. (C$_{22}$H$_{34}$O$_2$) C, H.

(3α,5α,22S,23S)-22,23-Epoxy-3-hydroxy-13,24-cyclo-18,21-dinorcholan-20-one (19a) and (3α,5α,22R,23R)-22,23-Epoxy-3-hydroxy-13,24-cyclo-18,21-dinorcholan-20-one (19b)

A mixture of MeOH (5 mL), 30% H$_2$O$_2$ (1.5 mL) and aqueous NaOH (4N, 0.25 mL) was added to a solution of enone 11a (100 mg, 0.30 mmol) in 1:1 MeOH and 1,4-dioxane (20 mL) at 0° C. The resultant solution was stirred at 0° C. for 3-4 h. EtOAc (30 mL) was added and the organic phase was washed with water and brine, and dried over Na$_2$SO$_4$. Solvent removal under reduced pressure gave a residue which was purified by column chromatography (silica gel; hexanes/EtOAc/CH$_2$Cl$_2$, 4:1:0.2) to give a mixture of compound 19a and 19b (1.8:1) 90 mg (86%). Analytical samples were obtained by HPLC separation (silica gel; hexanes/EtOAc, 6:1).

Compound 19a was obtained as white crystals: mp 238-240° C. (EtOAc-hexanes); $^1$H NMR δ 0.81 (s, 3H, 19-CH$_3$), 3.15 (d, J=3.3 Hz, 1H, epoxide H-22), 3.55 (s, 1H, epoxide H-23), 4.05 (m, 1H, CHOH); $^{13}$C NMR δ 11.2, 20.1, 20.9, 24.7, 27.6, 28.3, 29.0, 32.0, 32.1, 35.1, 35.7, 36.1, 36.4, 39.0, 42.0, 51.8, 53.7, 54.8, 56.4, 57.0, 66.4, 207.1 (CO); IR $\nu_{max}$ 3551, 2925, 1691 cm$^{-1}$. Anal. (C$_{22}$H$_{32}$O$_3$) C, H.

Compound 19b was obtained as white crystals: mp 194-195° C. (EtOAc-hexanes); $^1$H NMR δ 0.79 (s, 3H, 19-CH$_3$), 3.23 (d, J=3.6 Hz, 1H, epoxide H-22), 3.55 (t, J=3.6 Hz, 1H, epoxide H-23), 4.05 (m, 1H, CHOH); $^{13}$C NMR δ 11.3, 20.2, 24.2, 25.5, 26.0, 28.3, 29.0, 32.0, 32.2, 35.1, 35.8, 36.1, 36.4, 39.0, 51.5, 53.6, 54.5, 56.7, 57.9, 59.2, 66.4, 209.2 (CO); IR $v_{max}$ 3435, 2926, 1699 cm$^{-1}$. Anal. (C$_{22}$H$_{32}$O$_3$) C, H.

(3α,5α,23S)-13,24-Cyclo-18,21-dinorchol-20(22)-ene-3,23-diol (21a) and (3α,5α,23R)-13,24-Cyclo-18,21-dinorchol-20(22)-en-3,23-diol (21b)

The mixture of epoxides 19a and 19b (68 mg, 0.20 mmol), NH$_2$NH$_2$.xH$_2$O (x~1.5, 136 µL, 2.4 mmol) and AcOH (2.35 µL) in MeOH (4 mL) was refluxed for 2 h. Water (20 mL) was added and the product was extracted with CH$_2$Cl$_2$. The combined CH$_2$Cl$_2$ extracts were washed with water until the pH was neutral and then dried over Na$_2$SO$_4$. Solvent removal under reduced pressure gave a residue which was purified by column chromatography (silica gel; CH$_2$Cl$_2$/hexanes/EtOAc, 1:1:0.2) to give compound 21a (26 mg, 40%) and compound 21b (14 mg, 22%).

Compound 21a was obtained as white crystals: mp 94-96° C. (EtOAc-hexanes); $^1$H NMR δ 0.82 (s, 3H, 19-CH$_3$), 4.05 (m, 1H, CHOH), 4.22 (m, 1H, CH=CHCHOH), 5.72 (m, 1H, CH=CHCHOH), 5.97 (m, 1H, CH=CHCHOH); $^{13}$C NMR δ 11.3, 20.4, 25.3, 28.1, 28.6, 29.1, 30.4, 32.2, 32.3, 34.8, 35.7, 35.9, 36.3, 39.3, 40.0, 46.6, 54.7, 57.0, 64.8, 66.6, 125.6 (CH=), 133.9 (CH=); IR $v_{max}$ 3359, 3018, 2927, 1446, 1003 cm$^{-1}$.

Compound 21b was obtained as white crystals: mp 215-217° C. (EtOAc-hexanes); $^1$H NMR δ 0.81 (s, 3H, 19-CH$_3$), 4.05 (m, 1H, CHOH), 4.28 (m, 1H, CH=CHCHOH), 5.57 (d, J=10.2, 1H, CH=CHCHOH), 5.85 (m, 1H, CH=CHCHOH); $^{13}$C NMR δ 11.3, 20.2, 24.9, 28.5, 29.0, 29.8, 31.0, 32.2, 32.3, 34.2, 34.7, 35.9, 36.2, 39.2, 44.2, 46.4, 54.6, 56.4, 65.9, 66.6, 128.4 (CH=), 132.6 (CH=); IR $v_{max}$ 3328, 3019, 2926, 1446, 1003 cm$^{-1}$.

(3α,5α)-3-Hydroxy-13,24-cyclo-18,21-dinorchol-20(22)-en-23-one (21c)

Activated MnO$_2$ (420 mg, 4.83 mmol) was added to a mixture of compounds 21a and 21b (60 mg, 0.18 mmol) in CHCl$_3$ (20 mL). The reaction mixture was stirred at room temperature for 48 h. The MnO$_2$ was removed by filtration and the CHCl$_3$ was removed under reduced pressure. The residue was purified by column chromatography (silica gel; CH$_2$Cl$_2$/EtOAc, 20:1) to give compound 21c (28 mg, 47%) and a recovered mixture of compounds 21a and 21b (27 mg).

Compound 21c was obtained as white crystals: mp 209-210° C. (EtOAc-hexanes); $^1$H NMR δ 0.78 (s, 3H, 19-CH$_3$), 2.37 (d, J=16.2 Hz, 1H, CH$_2$CO), 4.05 (m, 1H, CHOH), 5.90 (d, J=9.9 Hz, 1H, C(O)CH=CH), 6.96 (dd, J=5.4, J=9.9 Hz, 1H, C(O)CH=CH); $^{13}$C NMR δ 11.3, 19.7, 26.3, 28.3, 29.0, 29.4, 32.0, 32.2, 34.2, 34.8, 35.8, 36.2, 38.0, 39.1, 47.3, 47.4, 54.2, 56.1, 66.5, 127.2 (C(O)CH=CH), 152.1 (C(O)CH=CH), 200.3 (CO); IR $v_{max}$ 3467, 2926, 1664, 1451, 1004 cm$^{-1}$. Anal. (C$_{22}$H$_{32}$O$_2$) C, H.

(3α,5α)-3-Hydroxy-13,24-cyclo-18,21-dinorcholan-23-one (4a)

Compound 21c (28 mg, 0.085 mmol) was dissolved in MeOH (10 mL) and hydrogenated (40 psi, H$_2$, 5% Pd/BaSO$_4$, 9 mg) for 2 h. The reaction mixture was filtered through a pad of Celite 545® to remove catalyst and the solvent was removed under reduced pressure. The product was purified by column chromatography (silica gel; hexanes/EtOAc, 4:1) to give compound 4a (26 mg, 94%).

Compound 4a was obtained as white crystals: mp 185-186° C. (EtOAc-hexanes); $^1$H NMR δ 0.76 (s, 3H, 19-CH$_3$), 4.04 (m, 1H, CHOH); $^{13}$C NMR δ 11.2, 19.8, 24.3, 24.9, 25.2, 28.3, 29.0, 31.9, 32.2, 34.2, 34.9, 35.8, 36.2, 36.5, 39.1, 40.5, 44.7, 48.8, 54.3, 56.3, 66.5, 213.7 (CO); IR $v_{max}$ 3435, 2921, 1704, 1005 cm$^{-1}$. Anal. (C$_{22}$H$_{34}$O$_2$) C, H.

(3α,5α)-13,24-Cyclo-18,21-dinorchola-20(22),23-diene-3,20-diol, 3,20-diacetate (23a)

A mixture of compound 11a (200 mg, 0.61 mmol), NaI (366 mg, 2.44 mmol) and Ac$_2$O (9 mL) was cooled to 0° C. under N$_2$ and Me$_3$SiCl (0.31 mL, 2.44 mmol) was added dropwise. The reaction mixture was stirred at ambient temperature for 24 h and then poured into 10% NaHCO$_3$ (50 mL). After the mixture was stirred for 10 min, the product was extracted using hexanes (4×50 mL). The combined extracts were washed with 10% NaHCO$_3$ (5 mL), 10% Na$_2$S$_2$O$_3$ (2×10 mL), water, and dried over Na$_2$SO$_4$. The solvent was removed under reduced pressure and the residue was purified by column chromatography (silica gel; hexanes/EtOAc, 30:1) to give compound 23a (173 mg, 69%).

Compound 23a was obtained as white crystals: mp 135-136° C. (hexanes); $^1$H NMR δ 0.82 (s, 3H, 19-CH$_3$), 2.06 (s, 3H, CHOC(O)CH$_3$), 2.15 (s, 3H, =COC(O)CH$_3$), 5.02 (m, 1H, CHOAc), 5.56 (d, J=5.7 Hz, 1H, CH=COAc), 5.65 (d, J=9.6 Hz, 1H, CH=CHCH=), 5.84 (dd, J=5.7 Hz, J=9.6 Hz, 1H, CH=CHCH=); $^{13}$C NMR δ 11.4, 20.1, 21.2, 21.5, 26.1, 28.4, 29.7, 32.3 (2×C), 32.9, 33.0, 35.9, 36.0, 37.5, 40.1, 47.9, 48.4, 54.2, 56.2, 70.1, 107.9 (CH=COAc), 122.4 (=CHCH=COAc), 127.7 (CCH=CH), 154.6 (=COAc), 169.1 (OC(O)CH$_3$), 170.7 (OC(O)CH$_3$); IR $v_{max}$ 3039, 2932, 1763, 1734, 1204. Anal. (C$_{26}$H$_{36}$O$_4$) C, H.

(3α,5α,20R)-13,24-Cyclo-18,21-dinorchol-23-en-3, 20-diol, 3-acetate (24a) and (3α,5α,20S)-13,24-Cyclo-18,21-dinorchol-23-en-3,20-diol, 3-acetate (24b)

Compound 23a (170 mg, 0.41 mmol) was dissolved in EtOH (15 mL), and NaBH$_4$ (78 mg, 2.05 mmol) was added. The solution was stirred under N$_2$ for 6 h. Most of the EtOH was removed under reduced pressure and the residue was dissolved in EtOAc (50 mL), washed with 5% HCl (10 mL), aqueous NaHCO$_3$ (10 mL), brine (10 mL), and dried over Na$_2$SO$_4$. The solvent was removed and the residue obtained was filtered through a short column (silica gel; hexanes/EtOAc, 8:1) to give a mixture of compounds 24a and 24b (140 mg, 92%). Analytical samples of compounds 24a and 24b were obtained by column chromatography (silica gel; hexanes/EtOAc, 20:1).

Compound 24a was obtained as white crystals: mp 159-161° C.; $^1$H NMR δ 0.81 (s, 3H, 19-CH$_3$), 2.06 (s, 3H, CH$_3$C(O)O), 4.10 (m, 1H, CHOH), 5.01 (m, 1H, CHOAc), 5.54 (m, 1H, =CHCH$_2$), 5.66 (d, 1H, J=10.5 Hz, CH=CHCH$_2$); $^{13}$C NMR δ 11.3, 20.6, 20.7, 21.5, 25.8, 26.0, 28.3, 30.7, 32.2, 32.8, 32.9, 35.3, 35.9, 38.6, 40.0, 47.9, 51.0, 54.5, 55.1, 66.8, 70.0, 124.7 (CH=), 129.6 (CH=), 170.6 (C(O)O); IR $v_{max}$ 3399, 3023, 2929, 1734, 1245. Anal. (C$_{24}$H$_{36}$O$_3$) C, H.

Compound 24b was obtained as white crystals: mp 168-169° C.; $^1$HNMR δ 0.83 (s, 3H, 19-CH$_3$), 2.06 (s, 3H, CH$_3$C(O)O), 4.06 (m, 1H, CHOH), 5.02 (m, 1H, CHOAc), 5.65 (m, 1H, CH$_2$CH=), 5.86 (d, J=10.5 Hz, 1H, CCH=); $^{13}$C NMR δ 11.3, 20.7, 21.5, 25.8, 26.1 (2×C), 28.3, 30.0, 32.2, 32.8 (2×C), 34.9, 35.9, 39.7, 40.0, 42.8, 50.1, 54.2, 55.7, 68.4, 70.1, 124.0 (CH=), 129.7 (CH=), 170.7 (C(O)O); IR $v_{max}$ 3442, 3021, 2931, 1735, 1249 cm$^{-1}$. Anal. (C$_{24}$H$_{36}$O$_3$) C, H.

(3α,5α)-3-(Acetyloxy)-13,24-cyclo-18,21-dinorchol-23-ene (28a)

A mixture of compounds 24a and 24b (150 mg, 0.40 mmol), Ph$_3$P (195 mg, 0.74 mmol), imidazole (101 mg, 1.48 mmol) and I$_2$ (150 mg, 0.59 mmol) in toluene (15 mL) was heated at 95° C. for 1.5 h. The toluene was removed under reduced pressure and the residue was purified by column chromatography (silica gel, CH$_2$Cl$_2$) to give a mixture of compounds 26a and 26b in quantitative yield. This product mixture was used without further purification or characterization.

The mixture of compounds 26a and 26b, i-PrOH (0.20 mL) and HMPA (0.50 mL) in THF (1 mL) was added to a freshly made SmI$_2$-THF solution (0.1 M, 10 mL) under Ar. The purple solution was stirred at room temperature for 30 min and quenched with saturated aqueous NH$_4$Cl (1 mL). The solution was extracted with CH$_2$Cl$_2$. The combined CH$_2$Cl$_2$ extracts were washed with saturated aqueous NH$_4$Cl, water, and dried over Na$_2$SO$_4$. The solvent was removed under reduced pressure and the residue was purified by column chromatography (silica gel; hexanes/EtOAc, 30:1) to give compound 28a contaminated with about 20% of the 20(22),23-diene. The mixture was dissolved in acetone (15 mL) and a 2% solution of 4-phenyl-1,2,4-triazoline-3,5-dione in acetone was added dropwise at 0° C. until the pink color persisted. After all of the diene was reacted with 4-phenyl-1,2,4-triazoline-3,5-dione (monitored by TLC), the solvent was removed and the residue was purified by column chromatography (silica gel; hexanes/EtOAc, 50:1) to give compound 28a (94 mg, 66% from compound 24a and 24b) as a single spot on TLC (silica gel plate). NMR analysis showed that product 28a contained ~10% of another inseparable and unidentified isomeric olefin product.

Compound 28a was obtained as a white solid: mp 117-119° C.; $^1$H NMR δ 0.82 (s, 3H, 19-CH$_3$), 2.05 (s, 3H, CH$_3$C(O)O), 5.01 (m, 1H, CHOAc), 5.67 (bs, 2H, CH=CH); $^{13}$C NMR δ 11.4, 20.5, 20.9, 21.2, 21.5, 24.5, 26.1, 26.1, 28.4, 32.3, 32.9 (2×C), 35.0, 35.9, 38.5, 40.1, 43.3, 43.8, 54.5, 55.1, 70.1, 128.0 (CH=), 129.7 (CH=), 170.7 (C(O)O); IR ν$_{max}$ 3019, 2932, 1736, 1446 cm$^{-1}$. Anal. (C$_{24}$H$_{36}$O$_2$) C, H.

(3α,5α)-3-(Acetyloxy)-13,24-cyclo-18,21-dinorchol-23-en-22-one (29a)

A solution of CrO$_3$ (280 mg, 2.8 mmol) in CH$_2$Cl$_2$ (4 mL) was cooled to −15° C. and 3,5-dimethylpyrazole (274 mg, 2.85 mmol) was added in one portion. The resultant brown slurry was stirred for 30 min followed by addition of compound 28a (40 mg, 0.112 mmol) in CH$_2$Cl$_2$ (4 mL). The mixture was stirred at −15° C. for 3 h and a 1:1 mixture of hexanes and ethyl acetate (20 mL) was added. The reaction mixture was filtered through a pad of silica gel. Solvent was removed under reduced pressure to give a residue which was purified by column chromatography (silica gel; hexanes/EtOAc, 10:1) to give compound 29a (28 mg, 67%). This product was contaminated with ~5% of an unidentified impurity which was removed after hydrolysis of the acetate group.

Partially purified compound 29a was obtained as white solid: mp 133-138° C.; $^1$H NMR δ 0.86 (s, 3H, 19-CH$_3$), 2.07 (s, 3H, CH$_3$C(O)O), 2.41 (dm, J=17.4 Hz, 1H, CH$_2$CO), 2.62 (dd, J=4.5 Hz, J=17.4 Hz, 1H, CH$_2$CO), 5.03 (m, 1H, CHOAc), 6.01 (d, J=10.5 Hz, 1H, =CHCO), 6.97 (dd, J=1.5 Hz, J=10.5 Hz, 1H, CH=CHCO); $^{13}$C NMR δ 11.4, 20.7, 21.5, 26.0, 26.7, 27.0, 28.1, 32.0, 32.8, 32.9, 35.3, 35.9, 36.4, 38.2, 40.0, 45.2, 45.6, 54.2, 56.9, 69.9, 130.1 (=CHCO), 152.3 (CH=CHCO), 170.6 (C(O)O), 199.7 (CO).

(3α,5α)-3-Hydroxy-13,24-Cyclo-18,21-dinorchol-23-en-22-one (30a)

Compound 29a (30 mg, 0.08 mmol) was dissolved in MeOH (2 mL) and 15% aq. NaOH (0.2 mL) was added. The solution was refluxed for 20 min and cooled to room temperature. EtOAc (20 mL) was added and the organic layer was washed with water and dried over Na$_2$SO$_4$. Solvent removal under reduced pressure gave a residue which was purified by column chromatography (silica gel; CH$_2$Cl$_2$/EtOAc, 20:1) to give compound 30a (22 mg, 83%).

Compound 30a was obtained as white crystals: mp 168-170° C. (Et$_2$O-EtOAc); $^1$H NMR δ 0.84 (s, 3H, 19-CH$_3$), 2.41 (dm, J=17.1 Hz, 1H, CH$_2$CO), 2.62 (dd, J=4.5 Hz, J=17.1 Hz, 1H, CH$_2$CO), 4.07 (m, 1H, CHOH), 6.00 (d, J=10.2 Hz, 1H, =CHCO), 6.97 (dd, J=1.8 Hz, J=10.2 Hz, 1H, CH=CHCO); $^{13}$C NMR δ 11.3, 20.7, 26.7, 27.6, 28.4, 29.0, 32.1, 32.2, 35.4, 35.8, 36.2, 36.5, 38.2, 39.1, 43.9, 45.6, 54.3, 56.9, 66.4, 130.1 (=CHCO), 152.5 (CH=CHCO), 199.9 (CO); IR ν$_{max}$ 3320, 3028, 2926, 1679, 1445. Anal. (C$_{22}$H$_{32}$O$_2$) C, H.

(3α,5α,23R,24R)-23,24-Epoxy-13,24-cyclo-18,21-dinorcholan-3-ol, acetate (31a)

A mixture of NaHCO$_3$ (33 mg, 0.40 mmol), m-CPBA (103 mg, 0.60 mmol) and compound 28a (71 mg, 0.20 mmol) in CH$_2$Cl$_2$ (15 mL) was stirred at room temperature for 5 hrs. It was washed successively with 5% Na$_2$S$_2$O$_3$, 10% NaHCO$_3$ and brine, and dried over Na$_2$SO$_4$. After solvent removal under reduced pressure, the residue obtained was purified by column chromatography (silica gel; hexanes/EtOAc, 50:1) to give compound 31a (67 mg, 90%).

Compound 31a was obtained as a white solid: mp 126-128° C. [containing ~10% (23S, 24R)-epoxide]; $^1$H NMR δ 0.81 (s, 3H, 19-CH$_3$), 2.06 (s, 3H, CH$_3$C(O)O), 2.96 (d, J=3.9 Hz, 1H, epoxide 24-H), 3.16 (m, 1H, epoxide 23-H), 5.02 (m, 1H, CHOAc); $^{13}$C NMR δ 11.4, 18.3, 19.4, 21.1, 21.5, 24.5, 26.0, 26.1, 28.3, 32.3, 32.8, 32.9, 34.5, 34.7, 35.9, 40.0, 40.7, 41.3, 54.3, 54.4, 54.6, 55.8, 70.0, 170.6 (C(O)O); IR ν$_{max}$ 2930, 1735, 1235 cm$^{-1}$.

(3α,5α,23S,24R)-23-Bromo-13,24-cyclo-18,21-dinorcholan-3,24-diol, 3-acetate (32a)

Compound 31a (71 mg, 0.19 mmol) in MeCN (10 mL) was cooled to −40° C. and hydrobromic acid (48%, 0.25 mL) was added dropwise. The solution was stirred at 0° C. for 2 h and then at room temperature for 1 h. EtOAc (50 mL) was added and the organic layer was washed with water to neutral pH, and dried over Na$_2$SO$_4$. The solvent was removed under reduced pressure and the residue was purified by column chromatography (silica gel; hexanes/EtOAc, 50:1) to give compound 32a (60 mg, 70%).

Compound 32a was obtained as a white solid: mp 161.5-163.5° C.; $^1$H NMR δ 0.77 (s, 3H, 19-CH$_3$), 2.05 (s, 3H, CH$_3$C(O)O), 3.65 (dd, J=1.8 Hz, J=10.5 Hz, 1H, CHOH), 4.32 (m, 1H, CHBr), 5.00 (m, 1H, CHOAc); $^{13}$C NMR δ 11.2, 21.6, 22.6, 23.3, 24.8, 24.9, 26.1, 28.4, 31.9, 32.5, 32.9 (2×C), 33.0, 35.3, 36.1, 40.3, 47.7, 48.2, 54.6, 58.3, 63.7, 70.3, 74.4, 170.7 (C(O)O); IR ν$_{max}$ 3554, 2931, 1733, 1261 cm$^{-1}$. Anal. (C$_{24}$H$_{37}$BrO$_3$) C, H.

(3α,5α,23S)-3-(Acetyloxy)-23-bromo-13,24-cyclo-18,21-dinorcholan-24-one (33a)

Jones reagent was added dropwise to a solution of compound 32a (58 mg, 0.13 mmol) in acetone (15 mL) at 5° C.

until an orange color persisted. The resultant mixture was stirred at 0-5° C. for 1 h. 2-propanol was added to consume excess oxidant and the acetone was removed under reduced pressure. The residue obtained was dissolved in EtOAc (30 mL) and washed with water to neutral pH, and dried over $Na_2SO_4$. The solvent was removed and the residue was purified by column chromatography (silica gel; hexanes/EtOAc, 20:1) to give compound 33a (57 mg, 98%).

Compound 33a was obtained as a white solid: mp 207-209° C.; $^1$H NMR δ 0.76 (s, 3H, 19-$CH_3$), 2.04 (s, 3H, $CH_3C(O)O$), 4.92 (dd, J=6.0 Hz, J=12.9 Hz, 1H, CHBr), 5.00 (m, 1H, CHOAc); $^{13}$C NMR δ 11.5, 21.5, 21.6, 23.6, 25.2, 25.4, 26.0, 28.2, 32.3, 32.8, 32.9, 35.2 (2×C), 35.8, 36.3, 40.0, 49.3, 54.6, 56.3, 57.0, 59.8, 70.0, 170.6 (C(O)O), 205.0 (CO); IR $v_{max}$ 2942, 1733, 1240 $cm^{-1}$. Anal. ($C_{24}H_{35}BrO_3$) C, H.

(3α,5α)-3-(Acetyloxy)-13,24-cyclo-18,21-dinorchol-22-en-24-one (34a)

A mixture of compound 33a (54 mg, 0.12 mmol), $Li_2CO_3$ (89 mg, 1.2 mmol) and LiBr (42 mg, 0.48 mmol) in DMF was heated at 125° C. under $N_2$ for 24 h. After cooling to room temperature, EtOAc (30 mL) was added and the organic layer was washed with water until neutral pH, and dried over $Na_2SO_4$. The solvent was removed and the residue was purified by column chromatography (silica gel; hexanes/EtOAc, 45:1) to give compound 34a (31 mg, 70%).

Compound 34a was obtained as white crystals: mp 122-124° C.; $^1$H NMR δ 0.87 (s, 3H, 19-$CH_3$), 2.05 (s, 3H, $CH_3C(O)O$), 5.02 (m, 1H, CHOAc), 5.80 (m, 1H, =CHCO), 6.62 (m, 1H, =$CHCH_2$); $^{13}$C NMR δ 11.5, 20.3, 21.5, 24.3, 26.1, 26.7, 27.7, 28.3, 32.7 (2×C), 32.9, 33.1, 35.4, 36.0, 40.3, 45.1, 53.5, 54.3, 57.2, 70.2, 129.4 (=CHCO), 144.4 (=$CHCH_2$), 170.6 (C(O)O), 204.0 (CO); IR $v_{max}$ 3031, 2938, 1734, 1666, 1247 $cm^{-1}$. Anal. ($C_{24}H_{34}O_3$) C, H.

(3α,5α)-3-Hydroxy-13,24-cyclo-18,21-dinorchol-22-en-24-one (35a)

Using the same procedure described for the preparation of compound 30a from compound 29a, compound 35a (21 mg, 80%) was prepared from compound 34a (30 mg, 0.08 mmol).

Compound 35a was obtained as white crystals: mp 242-243° C.; $^1$H NMR δ 0.86 (s, 3H, 19-$CH_3$), 4.05 (m, 1H, CHOH), 5.80 (m, 1H, =CHCO), 6.62 (m, 1H, =$CHCH_2$); $^{13}$C NMR δ 11.3, 20.3, 24.3, 26.8, 27.7, 28.5, 29.1, 32.4, 32.8 (2×C), 35.5, 36.0, 36.3, 39.4, 45.1, 53.5, 54.4, 57.2, 66.6, 129.4 (=CHCO), 144.5 (=$CHCH_2$), 204.1 (CO); IR $v_{max}$ 3439, 3031, 2908, 1647 $cm^{-1}$. Anal. ($C_{22}H_{32}O_2$) C, H.

(3α,5α)-3-Hydroxy-13,24-cyclo-18,21-dinorcholan-24-one (5a)

Using the same procedure described for the preparation of compound 2a from compound 11a, compound 5a (37 mg, 92%) was prepared from compound 35a (40 mg, 0.12 mmol).

Compound 5a was obtained as white crystals: mp 203-204° C. ($Et_2O$-hexanes); $^1$H NMR δ 0.75 (s, 3H, 19-$CH_3$), 4.04 (m, 1H, CHOH); $^{13}$C NMR δ 11.3, 21.6, 23.9, 23.9, 24.0, 25.4, 28.5, 29.0, 32.3, 32.6, 35.1, 35.3, 35.9, 36.2, 39.3, 40.2, 49.7, 54.9, 56.4, 58.5, 66.6, 216.7 (CO); IR $v_{max}$ 3317, 2923, 1708, 1003 $cm^{-1}$. Anal. ($C_{22}H_{34}O_2$) C, H.

(3α,5α)-3-(Acetyloxy)-13,24-cyclo-18,21-dinorcholan-20-one (36)

Compound 2a (100 mg, 0.303 mmol) was dissolved in pyridine (1 mL), and $Ac_2O$ (0.3 mL) was added. The mixture was stirred at room temperature for 20 h and then poured into saturated aqueous $NaHCO_3$ (10 mL). After stirring at room temperature for 10 min, the product was extracted with EtOAc. The combined EtOAc extracts were washed with 3% HCl, 5% $NaHCO_3$ and water and dried over $Na_2SO_4$. Solvent removal under reduced pressure gave a residue which was purified by column chromatography (silica gel; hexanes/EtOAc, 50:1) to give compound 36 (105 mg, 94%).

Compound 36 was obtained as white crystals: mp 197-198° C. (hexanes); IR $v_{max}$ 2938, 1732, 1696, 1244 $cm^{-1}$; $^1$H NMR δ 0.80 (s, 3H), 2.05 (s, 3H), 2.50 (m, 1H), 5.01 (m, 1H); $^{13}$C NMR δ 11.4, 20.4, 21.5, 22.2 (2×C), 25.1, 26.1, 27.0, 28.2, 32.1, 32.8 (2×C), 33.5, 35.2, 35.9, 37.4, 40.0, 49.6, 53.9, 56.8, 61.6, 70.0, 170.7, 215.5.

(3α,5α,20R)-3-Hydroxy-13,24-cyclo-18,21-dinorcholane-20-carbonitrile (39) and (3α,5α,20S)-3-Hydroxy-13,24-cyclo-18,21-dinorcholane-20-carbonitrile (40)

To the solution of compound 36 (53 mg, 0.142 mmol) in anhydrous THF (8 mL) was added diethyl cyanophosphonate (100 mg, 0.570 mmol) and LiCN (0.5 M solution in DMF, 1.14 mL, 0.57 mmol). The mixture was stirred at room temperature for 3 h and the solvent was removed under reduced pressure. The residue obtained was then purified by column chromatography (silica gel; hexanes/EtOAc, 4:1) to give compound 37 as a colorless oil that was used without further separation.

The mixture of compound 37 and MeOH (0.12 mL) in THF (3 mL) was added to a freshly made $SmI_2$-THF solution (0.1 M, 20 mL) under Ar. The resultant dark blue solution was stirred at room temperature overnight and then cooled to 0° C. 3% HCl (5 mL) was added to quench the reaction. Solvent was removed under reduced pressure and the residue was dissolved in EtOAc and washed with 5% $NaHCO_3$, 5% $Na_2S_2O_3$ and brine and dried over $Na_2SO_4$. After solvent removal under reduced pressure, compound 38 was obtained and it was dissolved in MeOH (8 mL). Then, 2.5 N NaOH (1.2 mL) was added. The solution obtained was stirred at room temperature overnight and MeOH was removed under reduced pressure. The residue was dissolved in $CH_2Cl_2$ and washed with water, 3% HCl and water and dried over $Na_2SO_4$. Solvent removal under reduced pressure gave a residue which was purified by column chromatography (silica gel; dichloroethane) to give compound 39 (25 mg, 51% from 36) and compound 40 (22 mg, 45% from 36).

Compound 39 was obtained as white crystals: mp 213-214° C. (EtOAc-hexanes); IR $v_{max}$ 3409, 2929, 2232, 1443, 1001 $cm^{-1}$; $^1$H NMR δ 0.76 (s, 3H), 2.75 (m, 1H), 4.04 (m, 1H); $^{13}$C NMR δ 11.2, 20.0, 20.3, 21.7, 22.9, 23.5, 24.8, 27.3, 28.4, 29.0, 31.9, 32.2, 32.8, 34.6, 35.9, 36.2, 39.1, 41.7, 46.8, 54.3, 56.8, 66.5, 122.5.

Compound 40 was obtained as white crystals: mp 250-251° C. (EtOAc-hexanes); IR $v_{max}$ 3319, 2922, 2234, 1448, 1009 $cm^{-1}$; $^1$H NMR δ 0.77 (s, 3H), 2.42 (m, 1H), 2.76 (m, 1H), 4.04 (m, 1H); $^{13}$C NMR δ 11.2, 17.9, 20.2, 22.5, 23.6, 23.8, 25.9, 27.1, 28.4, 29.0, 32.0, 32.1, 34.1, 34.5, 35.8, 36.2, 39.1, 41.5, 46.9, 54.3, 57.1, 66.5, 123.3.

(3α,5α)-3-(Acetyloxy)-13,24-cyclo-18,21-dinorcholan-22-one (41)

Using the same procedure described for the preparation of compound 36, compound 41 (60 mg, 97%) was prepared from compound 3a (55 mg, 0.167 mmol).

Compound 41 was obtained as white crystals: mp 178-180° C. (hexanes); IR $\nu_{max}$ 2936, 1733, 1237 cm$^{-1}$; $^1$H NMR δ 0.80 (s, 3H), 2.06 (s, 3H), 2.39 (dt, J=5.7, 14.4 Hz, 1H), 2.54 (dd, J=5.7, 14.4 Hz, 1H), 5.02 (m, 1H); $^{13}$C NMR δ 11.4, 20.4, 21.5, 23.4, 23.7, 26.1, 27.7, 28.2, 32.0, 32.7, 32.9, 32.9, 35.6, 35.9, 37.0, 40.1, 41.3, 41.6, 49.0, 54.3, 55.6, 70.0, 170.6, 213.3.

(3α,5α,22S)-3-Hydroxy-13,24-cyclo-18,21-dinorcholane-22-carbonitrile (44) and (3α,5α,22R)-3-Hydroxy-13,24-cyclo-18,21-dinorcholane-22-carbonitrile (45)

Using the same procedure described for the preparation of compound 39 and 40, compound 44 (14 mg, 26% from 41) and compound 45 (36 mg, 68% from 41) were prepared from compound 41 (58 mg, 0.156 mmol). Compounds 44 and 45 were separated by HPLC (silica gel, hexanes/EtOAc, 25:1, 2 mL/min).

Compound 44 was obtained as white crystals: mp 199-200° C. (Et$_2$O-hexanes); IR $\nu_{max}$ 3345, 2926, 2238, 1444, 1003 cm$^{-1}$; $^1$H NMR δ 0.76 (s, 3H), 2.02 (m, 1H), 2.58 (m, 1H), 4.04 (m, 1H); $^{13}$C NMR δ 11.2, 20.1, 21.9, 23.8, 24.0, 25.0, 25.2, 28.4 (2×C), 29.0, 32.0, 32.2, 32.9, 34.7, 35.9, 36.2, 39.2, 40.5, 44.7, 54.4, 56.7, 66.5, 123.3.

Compound 45 was obtained as white crystals: mp 244-246° C. (CH$_2$Cl$_2$-EtOAc-hexanes); IR $\nu_{max}$ 3513, 2929, 2234, 1456, 1016 cm$^{-1}$; $^1$H NMR δ 0.78 (s, 3H), 2.20 (m, 1H), 2.85 (m, 1H), 4.05 (m, 1H); $^{13}$C NMR δ 11.2, 19.1, 20.1, 23.4, 23.6, 23.9, 25.8, 25.9, 28.5, 29.0, 32.0, 32.2, 33.1, 34.6, 35.9, 36.2, 39.2, 41.1, 44.5, 54.5, 56.9, 66.5, 124.2.

(3α,5α)-3-(Acetyloxy)-13,24-cyclo-18,21-dinorcholan-23-one (46)

Using the same procedure described for the preparation of compound 36, compound 46 (59 mg, 95%) was prepared from compound 4a (55 mg, 0.167 mmol).

Compound 46 was obtained as white crystals: mp 183-185° C. (hexanes); IR $\nu_{max}$ 2931, 1734, 1712, 1247, 1235 cm$^{-1}$; $^1$H NMR δ 0.78 (s, 3H), 2.05 (s, 3H), 2.50 (m, 1H), 5.01 (m, 1H); $^{13}$C NMR δ 11.4, 19.8, 21.5, 24.3, 24.9, 25.2, 26.0, 28.1, 31.8, 32.8, 32.8, 34.2, 34.8, 35.9, 36.4, 40.0, 40.5, 44.7, 48.7, 54.2, 56.3, 70.0, 170.5, 213.5.

(3α,5α,20R)-3-Hydroxy-13,24-cyclo-18,21-dinorcholane-23-carbonitrile (49) and (3α,5α,20S)-3-Hydroxy-13,24-cyclo-18,21-dinorcholane-23-carbonitrile (50)

Using the same procedure described for the preparation of compounds 39 and 40, compound 49 (27 mg, 53% from 46) and compound 50 (15 mg, 29% from 46) were prepared from compound 46 (56 mg, 0.150 mmol). Compounds 49 and 50 were separated by HPLC (silica gel, hexanes/EtOAc, 6:1, 2 mL/min).

Compound 49 was obtained as white crystals: mp 182-183° C. (EtOAc-hexanes); IR $\nu_{max}$ 3343, 2929, 2232, 1451, 1003 cm$^{-1}$; $^1$H NMR δ 0.79 (s, 3H), 2.66 (m, 1H), 2.88 (m, 1H), 4.05 (m, 1H); $^{13}$C NMR δ 11.2, 20.1, 20.9, 22.9, 23.7, 24.0, 24.0, 24.7, 28.5, 29.1, 32.1, 32.1, 34.2, 34.6, 35.8, 36.2, 39.2, 41.0, 44.7, 54.5, 58.1, 66.5, 123.8.

Compound 50 was obtained as white crystals: mp 157-159° C. (Et$_2$O-hexanes); IR $\nu_{max}$ 3401, 2927, 2239, 1446, 1003 cm$^{-1}$; $^1$H NMR δ 0.79 (s, 3H), 2.43 (m, 1H), 4.05 (m, 1H); $^{13}$C NMR δ 11.3, 20.1, 23.4, 23.8, 24.3, 24.7, 24.8, 27.1, 28.4, 29.0, 32.0, 32.2, 33.1, 34.6, 35.9, 36.2, 39.2, 41.4, 44.3, 54.5, 57.0, 66.5, 123.5.

(3α,5α)-20-Methylene-13,24-cyclo-18,21-dinorcholan-3-ol (51)

A suspension of NaH (60% in mineral oil, 75 mg, 1.88 mmol) in anhydrous DMSO (3 mL) was heated at 75° C. for 45 min and cooled to room temperature. Methyltriphenylphosphonium bromide (690 mg, 1.93 mmol) in DMSO (2 mL) was added and stirred at room temperature for 10 min. Compound 2a (127 mg, 0.385 mmol) in DMSO (1.5 mL) was then added. The mixture obtained was heated at 70° C. for 4 h and cooled to room temperature. Brine was added and the product was extracted with EtOAc. The combined EtOAc extracts were washed with water and brine and dried over Na$_2$SO$_4$. Solvent removal under reduced pressure gave a residue which was purified by column chromatography (silica gel; hexanes/EtOAc, 5:1) to give compound 51 (116 mg, 92%).

Compound 51 was obtained as a white solid: mp 211-213° C. (EtOAc-hexanes); IR $\nu_{max}$ 3295, 2927, 1645, 1436, 1001 cm$^{-1}$; $^1$H NMR δ 0.77 (s, 3H), 4.04 (m, 1H), 4.61 (m, 2H); $^{13}$C NMR δ 11.2, 20.4, 22.6, 23.2, 24.7, 27.4, 28.6, 29.1, 30.9, 32.3 (2×C), 33.3, 35.0, 35.9, 36.2, 39.2, 44.9, 54.5, 55.9, 56.9, 66.6, 107.8, 150.2.

(3α,5α)-20-Methylene-13,24-cyclo-18,21-dinorcholan-3-ol (52)

Using the same procedure described for the preparation of compound 51, compound 52 (41 mg, 82%) was prepared from compound 2b (50 mg, 0.152 mmol).

Compound 52 was obtained as a white solid: mp 131-133° C. (hexanes); IR $\nu_{max}$ 3299, 2927, 1645, 1451, 1040 cm$^{-1}$; $^1$H NMR δ 0.91 (s, 3H), 3.63 (m, 1H), 4.61 (m, 2H); $^{13}$C NMR δ 20.4, 22.5, 23.1, 23.4, 24.7, 26.7, 27.1, 27.5, 30.5, 30.9, 33.4, 34.7, 35.3, 35.4, 36.4, 40.6, 42.1, 44.9, 55.9, 56.9, 71.8, 107.8, 150.1.

(3α,5α)-22-Methylene-13,24-cyclo-18,21-dinorcholan-3-ol (53)

Using the same procedure described for the preparation of compound 51, compound 53 (17 mg, 43%) was prepared from compound 3a (40 mg, 0.121 mmol).

Compound 53 was obtained as a white solid: mp 187-188° C. (hexanes); IR $\nu_{max}$ 3312, 2926, 1450 cm$^{-1}$; $^1$H NMR δ 0.77 (s, 3H), 4.04 (m, 1H), 4.58 (s, 1H), 4.69 (s, 1H); $^{13}$C NMR δ 11.2, 20.3, 23.9, 24.4, 25.5, 28.5, 29.1, 30.5, 32.2, 32.2, 33.0, 34.3, 34.9, 35.9, 36.2, 39.3, 41.3, 47.7, 54.6, 56.8, 66.6, 108.3, 147.9.

(3α,5α)-3-Methoxymethoxy-13,24-cyclo-18,21-dinorcholan-20-one (54)

Chloromethyl methyl ether (84 mg, 1.05 mmol) was added to a solution of compound 2a (115 mg, 0.35 mmol) and N,N-diisopropyl ethylamine (0.30 mL, 1.75 mmol) in CH$_2$Cl$_2$ (10 mL). The resultant solution was stirred at room temperature for 20 h. The solvent was partially removed and the residue was purified by column chromatography (silica gel; hexanes/EtOAc, 15:1) to give compound 54 (126 mg, 97%).

Compound 54 was obtained as white crystals: mp 138-139° C. (Hexanes); IR $v_{max}$ 2928, 1702, 1446, 1045 cm$^{-1}$; $^1$H NMR δ 0.79 (s, 3H), 2.50 (m, 1H), 3.36 (s, 3H), 3.83 (m, 1H), 4.65 (m, 2H); $^{13}$C NMR δ 11.3, 20.3, 22.1 (2×C), 25.0, 26.2, 26.9, 28.4, 32.1, 32.7, 33.5, 33.5, 35.1, 35.8, 37.3, 39.6, 49.5, 53.9, 55.0, 56.7, 61.4, 71.5, 94.5, 215.3.

(3α,5α)-3-Methoxymethoxy-13,24-cyclo-18,21-dinorchol-20(22)-en-20-ol trifluoromethanesulfonate (55)

A solution of compound 54 (128 mg, 0.342 mmol) and N-phenyltrifluoromethanesulfonimide (367 mg, 1.03 mmol) in anhydrous THF (20 mL) was cooled to −78° C. and KHMDS (0.5 M solution in toluene, 1.37 mL, 0.685 mmol) was added. The mixture was stirred at room temperature for 1 h and saturated aqueous NH$_4$Cl (1 mL) was added. The product was extracted with ether and the combined ether extracts were washed with aqueous NH$_4$Cl and brine and dried over Na$_2$SO$_4$. The solvent was removed and the residue was purified by column chromatography (silica gel; hexanes/EtOAc, 50:1) to give compound 55 (169 mg, 97%). Compound 55 was partially characterized. It had $^1$H NMR δ 0.79 (s, 3H), 3.37 (s, 3H), 3.83 (m, 1H), 4.66 (m, 2H), 5.61 (m, 1H).

(3α,5α)-3-Methoxymethoxy-13,24-cyclo-18,21-dinorchol-20(22)-ene-20-carbonitrile (56)

A mixture of compound 55 (165 mg, 0.333 mmol), triethylamine (3 mL), trimethylsilyl cyanide (0.5 mL) and tetrakis(triphenylphosphine)palladium(0) (96.3 mg, 0.083 mmol) in benzene (10 mL) was refluxed under N$_2$ for 20 h. The solvent was partially removed and the residue was purified by column chromatography (silica gel; hexanes/EtOAc, 30:1) to give compound 56 (45 mg, 35%).

Compound 56 was obtained as white crystals: mp 136-138° C. (hexanes); IR $v_{max}$ 2927, 2212, 1456, 1041 cm$^{-1}$; $^1$H NMR δ 0.79 (s, 3H), 3.37 (s, 3H), 3.83 (m, 1H), 4.66 (m, 2H), 6.50 (t, 1H, J=3.6 Hz); $^{13}$C NMR δ 11.4, 18.5, 19.9, 22.6, 24.4, 26.3, 28.5, 29.6, 32.0, 32.8, 32.8, 33.6, 34.8, 35.9, 39.7, 41.1, 47.4, 54.3, 55.1, 55.5, 71.5, 94.5, 116.5, 119.9, 142.6.

(3α,5α)-3-Hydroxy-13,24-cyclo-18,21-dinorchol-20(22)-ene-20-carbonitrile (57)

12 N HCl (0.6 mL) was added to a solution of compound 56 (41 mg, 0.106 mmol) in MeOH (3 mL) and CH$_2$Cl$_2$ (0.5 mL) and stirred at room temperature for 2 h. EtOAc (20 mL) was added and the organic phase was washed with water, 5% NaHCO$_3$ and brine and dried over Na$_2$SO$_4$. Solvent removal under reduced pressure gave a residue which was purified by column chromatography (silica gel; hexanes/EtOAc, 8:1) to give compound 57 (32 mg, 89%).

Compound 57 was obtained as white crystals: mp 193-195° C. (EtOAc-hexanes); IR $v_{max}$ 3426, 2925, 2212, 1455, 1002 cm$^{-1}$; $^1$H NMR δ 0.79 (s, 3H), 4.04 (m, 1H), 6.50 (t, 1H, J=3.6 Hz); $^{13}$C NMR δ 11.2, 18.5, 19.9, 22.6, 24.4, 28.4, 29.0, 29.6, 32.0, 32.2, 32.7, 34.8, 35.8, 36.2, 39.1, 41.1, 47.4, 54.3, 55.5, 66.4, 116.4, 119.9, 142.6.

(3α,5α)-13,24-Cyclo-18,21-dinorchol-20(22),23-dien-3-ol acetate (59)

Mesyl chloride (20 μL, 0.258 mmol) was added to a solution of compound 24a (24 mg, 0.065 mmol) and triethylamine (80 μL, 0.581 mmol) in CH$_2$Cl$_2$ (5 mL) at 0° C. and stirred at room temperature for 1 h. The reaction mixture was washed with water and 3% HCl and water and dried over Na$_2$SO$_4$. The solvent was removed under reduced pressure to give crude mesylate 58. It was dissolved in toluene (2 mL) and DBU (0.1 mL) was added. The mixture was refluxed for 5 h and cooled to room temperature. The reaction mixture was washed with 3% HCl and water and dried over Na$_2$SO$_4$. Solvent removal under reduced pressure gave a residue which was purified by column chromatography (silica gel; hexanes/EtOAc, 20:1) to give compound 59 (19 mg, 83% from 24a).

Compound 59 was obtained as a colorless oil; IR $v_{max}$ 3032, 2932, 1736, 1445, 1246 cm$^{-1}$; $^1$H NMR δ 0.83 (s, 3H), 2.06 (s, 3H), 5.02 (m, 1H), 5.73-5.80 (m, 2H), 5.88 (m, 1H), 5.95 (m, 1H); $^{13}$C NMR δ 11.4, 20.1, 21.5, 26.1, 28.4, 30.1, 32.4, 32.9, 33.0, 33.2, 35.7, 35.9, 37.4, 40.1, 44.5, 44.9, 54.3, 56.3, 70.1, 121.4, 124.1, 130.0, 131.1, 170.7.

(3α,5α)-13,24-Cyclo-18,21-dinorchol-20(22),23-dien-3-ol (60).

LiAlH$_4$ (10 mg, 0.263 mmol) was added to a solution of compound 59 (20 mg, 0.056 mmol) in anhydrous THF (5 mL) and stirred at room temperature for 20 min. The reaction mixture was cooled to 0° C. and water (0.1 mL) was added dropwise to quench the reaction. The precipitate that formed was filtered through a pad of Celite 545. The solvent was removed from the filtrate and the residue was purified by column chromatography (silica gel; hexanes/EtOAc, 10:1) to give compound 60 (16 mg, 91%).

Compound 60 was obtained as a white solid: mp 136-138° C. (Hexanes); IR $v_{max}$ 3318, 3034, 2928, 1445, 1004 cm$^{-1}$; $^1$H NMR δ 0.82 (s, 3H), 4.05 (m, 1H), 5.74-5.80 (m, 2H), 5.88 (m, 1H), 5.95 (m, 1H); $^{13}$C NMR δ 11.2, 20.1, 28.6, 29.1, 30.1, 32.3, 32.5, 33.2, 35.7, 35.9, 36.2, 37.5, 39.2, 44.5, 44.9, 54.4, 56.3, 66.6, 121.3, 124.0, 130.1, 131.2.

(3α,5α)-13,24-Cyclo-18,21-dinorchol-23-en-3-ol (61)

Using the same procedure described for the preparation of compound 60, compound 61 (45 mg, 85%) was prepared from compound 28a (60 mg, 0.169 mmol).

Compound 61 was obtained as a white solid: mp 166.5-169° C. (hexanes); $^1$H NMR δ 0.81 (s, 3H), 4.04 (m, 1H), 5.68 (bs, 2H); $^{13}$C NMR δ 11.2, 20.5, 20.9, 21.3, 24.6, 26.2, 28.6, 29.1, 32.2, 32.4, 35.1, 35.9, 36.3, 38.5, 39.2, 43.4, 43.8, 54.7, 55.2, 66.6, 127.9, 129.8.

(3α,5α,20E)-3-Methoxymethoxy-13,24-cyclo-18-norcholan-20-ene-21-carbonitrile (62)

Compound 54 (50 mg, 0.134 mmol) and (triphenylphosphoranylidene)acetonitrile (100 mg, 0.332 mmol) was heated at 160° C. under N$_2$ for 15 h and then purified by column chromatography (silica gel; hexanes/EtOAc, 10:1) to give compound 62 (37 mg, 70%).

Compound 62 was obtained as white crystals: mp 159-161° C. (hexanes); IR $v_{max}$ 2928, 2215, 1625, 1446, 1041 cm$^{-1}$; $^1$H NMR δ 0.77 (s, 3H), 2.07 (t, 1H, J=9.0 Hz), 2.22 (m, 1H), 2.76 (m, 1H), 3.37 (s, 3H), 3.83 (m, 1H), 4.66 (m, 1H), 5.03 (d, 1H, J=1.8 Hz); $^{13}$C NMR δ 11.4, 20.3, 22.4, 22.7, 24.7, 26.3, 28.0, 28.5, 29.0, 32.1, 32.8, 33.2, 33.6, 35.1, 35.9, 40.0, 47.4, 54.2, 55.1, 56.4, 57.0, 71.6, 92.5, 94.5, 117.2, 170.1.

(3α,5α,20E)-3-Hydroxy-13,24-cyclo-18-norcholan-20-ene-21-carbonitrile (63)

Using the same procedure described for the preparation of compound 57, compound 63 (34 mg, 94%) was prepared from compound 62 (41 mg, 0.103 mmol).

Compound 63 was obtained as white crystals: mp 210-212° C.(ether-hexanes); IR $v_{max}$ 3308, 2928, 2217, 1444 cm$^{-1}$; $^1$H NMR δ 0.77 (s, 3H), 2.07 (t, 1H, J=9.0 Hz), 2.22 (m, 1H), 2.77 (m, 1H), 4.04 (m, 1H), 5.04 (d, 1H, J=1.5 Hz); $^{13}$C NMR δ 11.2, 20.3, 22.4, 22.7, 24.7, 28.0, 28.4, 28.9, 29.0, 32.2 (2×C), 33.2, 35.0, 35.8, 36.1, 39.1, 47.4, 54.2, 56.4, 56.9, 66.5, 92.5, 117.2, 170.0.

(3α,5α,20E)-3-Hydroxy-13,24-cyclo-18-norcholan-20-ene-21-carbonitrile (63) and (3α,5α,20Z)-3-Hydroxy-13,24-cyclo-18-norcholan-20-ene-21-carbonitrile (64)

Diethyl cyanomethylphosphonate (0.78 mL, 4.83 mmol) was added dropwise to the mixture of NaH (60% in mineral oil, 175 mg, 4.38 mmol) and THF (10 mL) at room temperature and refluxed for 10 min. Compound 2a (280 mg, 0.85 mmol) in THF (20 mL) was then added and reflux was continued for 20 min. The reaction mixture was then cooled to room temperature. EtOAc (100 mL) was added and the organic phase was washed with water and dried over Na$_2$SO$_4$. Solvent removal under reduced pressure gave a residue that was purified by column chromatography (silica gel; CH$_2$Cl$_2$/EtOAc, 40:1) to give compound 63 (164 mg, 55%) and compound 64 (109 mg, 36%).

Compound 63 was obtained as white crystals: mp. 214-216° C. (EtOAc-hexanes); $^1$H NMR δ 0.77 (s, 3H), 2.07 (t, 1H, J=9.0 Hz), 2.22 (m, 1H), 2.77 (dm, 1H, J=15.6 Hz), 4.04 (m, 1H), 5.04 (d, 1H, J=1.5 Hz); $^{13}$C NMR δ 11.1, 20.2, 22.2, 22.6, 24.6, 27.9, 28.3, 28.9 (2×C), 32.1 (2×C), 33.1, 34.9, 35.7, 36.0, 39.0, 47.3, 54.1, 56.3, 56.8, 66.3, 92.4, 117.2, 170.0; IR $v_{max}$ 3308, 2928, 2217, 1444 cm$^{-1}$.

Compound 64 was obtained as white crystals: mp. 201.5-203° C. (ether-hexanes); $^1$H NMR δ 0.77 (s, 3H), 2.18 (m, 1H), 2.32 (m, 1H), 2.69 (t, 1H, J=9.3 Hz), 4.04 (m, 1H), 5.05 (d, 1H, J=1.8 Hz); $^{13}$C NMR δ 11.2, 20.2, 22.3, 23.0, 24.7, 27.3, 28.4, 29.0, 31.8, 32.1, 32.1, 32.9, 35.0, 35.8, 36.1, 39.1, 47.4, 53.0, 54.1, 56.8, 66.4, 92.8, 117.1, 170.1; IR $v_{max}$ 3401, 2927, 2215, 1621, 1445 cm$^{-1}$.

(3α,5α,20S)-3-Methoxymethoxy-13,24-cyclo-18,21-dinorcholan-20-ol (65) and (3α,5α,20R)-3-Methoxymethoxy-13,24-cyclo-18,21-dinorcholan-20-ol (66)

The mixture of compound 18a (180 mg, 0.48 mmol) and NaBH$_4$ (60 mg, 1.58 mmol) in EtOH (10 mL) was stirred at room temperature for 30 min and EtOH was removed under reduced pressure. EtOAc (30 mL) was added and the solution was washed with water, 5% HCl and water and dried over Na$_2$SO$_4$. Solvent was removed under reduced pressure and the residue purified by column chromatography (silica gel; hexanes/EtOAc, 10:1) gave compound 65 (55 mg, 30%) and compound 66 (115 mg, 64%).

Compound 65 was obtained as white solid: mp. 131-133° C; $^1$H NMR δ 0.78 (s, 3H), 2.29 (m, 1H), 3.37 (s, 3H), 3.82 (m, 1H), 3.91 (bs, 1H), 4.66 (m, 2H); $^{13}$C NMR δ 11.4, 15.5, 20.4, 23.0, 24.1, 25.4, 26.3, 28.5, 28.8, 32.0, 32.8, 33.6, 34.4, 35.5, 35.9, 39.7, 41.1, 53.0, 54.4, 55.1, 57.3, 69.7, 71.6, 94.5; IR $v_{max}$ 3369, 2923, 1445, 1040 cm$^{-1}$.

Compound 66 was obtained as white solid: mp. 136-138° C.; $^1$H NMR δ 0.77 (s, 3H), 1.97 (m, 1H), 3.37 (s, 3H), 3.82 (m, 1H), 3.87 (m, 1H), 4.66 (m, 2H); $^{13}$C NMR δ 11.4, 20.2, 20.4, 20.6, 22.2, 23.6, 26.3, 28.5, 30.0, 32.1, 32.8, 33.6 (2×C), 34.9, 36.0, 39.8, 44.4, 52.6, 54.6, 55.1, 57.1, 69.7, 71.6, 94.5; IR $v_{max}$ 3401, 2923, 1446, 1041 cm$^{-1}$.

(3α,5α,20S)-13,24-cyclo-18,21-dinorcholane-3,20-diol (67)

37% aqueous HCl (0.6 mL) was added the solution of compound 65 (25 mg, 66 µmol) in CH$_3$OH (2 mL). The solution was stirred at room temperature for 1 h and EtOAc (30 mL) was added. It was washed with water, 10% NaHCO$_3$, and brine and dried over Na$_2$SO$_4$. Solvent was removed under reduced pressure and the residue was purified by column chromatography (silica gel; hexanes/EtOAc, 6:1) to give compound 67 (21 mg, 95%).

Compound 67 was obtained as white crystals: mp 261-262° C. (CHCl$_3$-hexanes); $^1$H NMR (CDCl$_3$/CD$_3$OD) δ 0.77 (s, 3H), 2.29 (m, 1H), 3.90 (m, 1H), 4.01 (m, 1H); $^{13}$C NMR δ 11.1, 15.4, 20.3, 22.8, 24.0, 25.3, 28.4, 28.5, 28.6, 32.0, 32.0, 34.3, 35.2, 35.6, 36.0, 39.0, 40.9, 52.6, 54.3, 57.2, 66.2, 69.4; IR $v_{max}$ 3307, 2916, 1443, 1001 cm$^{-1}$.

(3α,5α,20R)-13,24-cyclo-18,21-dinorcholane-3,20-diol (68)

Using the same procedure described for the preparation of compound 67 from compound 65, compound 68 (20 mg, 91%) was prepared from compound 66 (25 mg, 66 µmol).

Compound 68 was obtained as white crystals: mp 269-271° C. (methanol); $^1$H NMR (CDCl$_3$/CD$_3$OD) δ 0.78 (s, 3H), 2.00 (m, 1H), 3.85 (m, 1H), 3.98 (m, 1H); $^{13}$C NMR δ 11.7, 20.9, 21.1 (2×C), 22.8, 24.2, 29.2 (2×C), 29.9, 32.8, 32.9, 34.3, 35.6, 36.2, 36.8, 39.8, 44.9, 53.2, 55.4, 57.8, 66.7, 69.9; IR $v_{max}$ 3338, 2929, 1444, 1049 cm$^{-1}$.

(3α,5α,20S)-20-Methoxy-13,24-cyclo-18,21-dinorcholan-3-ol (69)

The solution of compound 65 (30 mg, 80 µmol) in THF (3 mL) was added to the slurry of NaH (60% in mineral oil, 16 mg, 0.40 mmol) in THF (2 mL) and stirred for 10 min. MeI (27 µL, 0.44 mmol) was added and refluxed overnight. The same amount of NaH and MeI was added again and refluxed for another 1 h and cooled to room temperature. Water was added to the reaction mixture and it was extracted with EtOAc. The combined EtOAc extracts were washed with water to neutral pH and then dried over Na$_2$SO$_4$. Solvent was removed under reduced pressure and the oil obtained was dissolved in MeOH (3 mL) and 37% HCl (1 mL) was added and stirred at room temperature for 2 h. EtOAc (30 mL) was added and it was washed with water and brine to neutral pH and then dried over Na$_2$SO$_4$. Solvent was removed under reduced pressure and the residue purified by column chromatography (silica gel; hexanes/EtOAc, 8:1) gave compound 69 (24 mg, 87%).

Compound 69 was obtained as white crystals: mp 182-183° C. (EtOAc-hexanes); $^1$H NMR δ 0.76 (s, 3H), 2.25 (m, 1H), 3.28 (s, 3H), 3.32 (m, 1H), 4.03 (m, 1H); $^{13}$C NMR δ 11.2, 16.1, 20.2, 23.1, 24.2, 25.4 (2×C), 28.5, 29.0, 32.1 (2×C), 34.5, 34.8, 35.9, 36.2, 39.2, 41.3, 48.6, 54.5, 56.0, 57.4, 66.6, 78.7; IR $v_{max}$ 3306, 2927, 1446, 1089 cm$^{-1}$.

(3α,5α,20R)-20-Methoxy-13,24-cyclo-18,21-dinorcholan-3-ol (70)

Using the same procedure described for the preparation of compound 69 from compound 65, compound 70 (29 mg, 90%) was prepared from compound 66 (35 mg, 93 µmol).

Compound 70 was obtained as white crystals: mp 200-202° C. (hexanes); $^1$H NMR δ 0.77 (s, 3H), 1.97 (m, 1H), 3.31 (s, 3H), 3.39 (m, 1H), 4.04 (m, 1H); $^{13}$C NMR δ 11.2, 20.2, 20.4, 20.7, 22.5, 23.6, 26.6, 28.5, 29.0, 32.1, 32.2, 33.8, 34.9, 35.9, 36.2, 39.2, 44.1, 49.3, 54.6, 55.4, 57.1, 66.5, 78.5; IR $v_{max}$ 3293, 2921, 1445, 1103 cm$^{-1}$.

(3α,5α,20R,22S)-20,22-Epoxy-13,24-cyclo-18,21-dinorcholan-3-ol (71) and (3α,5α,20S,22R)-20,22-epoxy-13,24-cyclo-18,21-dinorcholan-3l (72)

The mixture of compound 13a (96 mg, 0.31 mmol), NaHCO$_3$ (46 mg, 0.55 mmol) and m-CPBA (77% max, 106 mg, 0.47 mmol) in CH$_2$Cl$_2$ (15 mL) was stirred at room temperature for 4 h. The solution was washed with water, 5% NaHCO$_3$, 5% Na$_2$S$_2$O$_3$ and water and dried over Na$_2$SO$_4$. Solvent was removed under reduced pressure and the residue purified by column chromatography (silica gel; CH$_2$Cl$_2$/EtOAc, 50:1) gave compound 71 (33 mg, 33%) and compound 72 (54 mg, 54%).

Compound 71 was obtained as white crystals: mp 206-208° C. (EtOAc-hexanes); $^1$H NMR δ 0.75 (s, 3H), 3.05 (dd, 1H, J=1.5, 3.9 Hz), 3.18 (dd, 1H, J=3.9, 6.3 Hz), 4.03 (m, 1H); $^{13}$C NMR δ 11.1, 18.8, 20.0, 20.4, 24.3, 24.6, 28.5, 29.0, 32.1 (2×C), 34.3, 34.9, 35.8, 36.1, 39.1, 41.5, 44.7, 52.3, 54.4, 55.9, 56.7, 66.5; IR $v_{max}$ 3400, 2927, 1435 cm$^{-1}$.

Compound 72 was obtained as white crystals: mp 203.5-205° C. (acetone-hexanes); $^1$H NMR δ 0.77 (s, 3H), 3.13 (m, 1H), 3.22 (m, 1H), 4.03 (m, 1H); $^{13}$C NMR δ 11.1, 15.5, 19.8, 20.1, 24.3, 25.1, 28.5, 28.9, 32.2 (2×C), 33.8, 34.8, 35.8, 36.2, 39.1, 39.8, 43.8, 53.1, 53.6, 54.4, 55.7, 66.4; IR $v_{max}$ 3233, 2921, 1432, 1000 cm$^{-1}$.

(3α,5α,20S)-20,21-Epoxy-13,24-cyclo-18-norcholan-3-ol (73) and (3α,5α,20R)-20,21-Epoxy-13,24-cyclo-18-norcholan-3-ol (74)

Using the same procedure described for the preparation of compound 71 and 72 from compound 13a, compound 73 (30 mg, 48%) and compound 74 (26 mg, 41%) was prepared from compound 51 (60 mg, 0.18 mmol). Compounds 73 and 74 were separated by column chromatography (silica gel; CH$_2$Cl$_2$/EtOAc, 30:1).

Compound 73 was obtained as white crystals: mp. 186-192° C. (EtOAc-hexanes, decomposed); $^1$H NMR δ 0.78 (s, 3H), 2.00 (m, 1H), 2.25 (m, 1H), 2.48 (d, 1H, J=4.8 Hz), 2.46 (d, 1H, J=4.8 Hz), 4.04 (m, 1H); $^{13}$C NMR δ 11.2, 19.2, 20.2, 22.2, 24.4, 24.9, 28.5, 29.0, 29.3, 32.1, 32.2, 33.8, 34.7, 35.8, 36.2, 39.1, 43.6, 51.4, 53.4, 54.4, 56.8, 58.9, 66.5; IR $v_{max}$ 3307, 2927, 1445 cm$^{-1}$.

Compound 74 was obtained as white crystals: mp. 206-211° C. (EtOAc-hexanes, decomposed); $^1$H NMR δ 0.78 (s, 3H), 2.02 (m, 2H), 2.59 (d, 1H, J=5.4 Hz), 2.55 (dd, 1H, J=1.5, 5.4 Hz), 4.05 (m, 1H); $^{13}$C NMR δ 11.2, 20.2, 21.3, 22.2, 23.6, 24.2, 28.4, 28.9, 29.3, 31.4, 32.2, 33.5, 35.0, 35.9, 36.2, 39.1, 45.7, 53.5, 54.4, 55.7, 56.8, 59.4, 66.5; IR $v_{max}$ 3306, 2928, 1455 cm$^{-1}$.

(3α,5α)-3-Methoxymethoxy-21-methyl-13,24-cyclo-18-norchol-20-ene (75)

Ethyltriphenylphosphonium bromide (870 mg, 2.35 mmol) was added to the mixture of KOBu$^t$ (240 mg, 2.14 mmol) in THF (12 mL) at room temperature and refluxed for 30 min. Compound 18a (165 mg, 0.44 mmol) in THF (10 mL) was then added and refluxed for another 30 min and cooled to room temperature. Water was added to the reaction mixture and it was extracted with EtOAc. The combined EtOAc extracts were washed with water and dried over Na$_2$SO$_4$. Solvent was removed under reduced pressure and the residue purified by column chromatography (silica gel; CH$_2$Cl$_2$/EtOAc, 50:1) gave compound 75 (166 mg, 98%) as a colorless oil. It is a mixture of the two olefin isomers in the ratio >10:1.

The Main isomer has: $^1$H NMR δ 0.78 (s, 3H), 1.55 (dd, 3H, J=2.4, 6.6 Hz), 1.93 (m, 2H), 2.17 (m, 1H), 2.38 (m, 1H), 3.37 (s, 3H), 3.82 (m, 1H), 4.66 (m, 2H), 5.21 (m, 1H); $^{13}$C NMR δ 11.4, 12.3, 20.3, 23.2, 23.3, 24.6, 26.1, 26.3, 28.6, 32.2, 32.6, 32.9, 33.4, 33.6, 34.9, 36.0, 39.8, 44.4, 48.3, 54.5, 55.1, 57.0, 71.6, 94.5, 116.8, 140.0; IR $v_{max}$ 2927, 1445, 1044 cm$^{-1}$.

(3α,5α,20S)-1-[3-Methoxymethoxy-13,24-cyclo-18,21-dinorcholan-20-yl]ethanone (77) and (3α,5α,20R)-1-[3-Methoxymethoxy-13,24-cyclo-18,21-dinorcholan-20-yl]ethanone (78)

BH$_3$ (1.0 M in THF, 1.28 mL, 1.28 mmol) was added to compound 75 (165 mg, 0.43 mmol) in anhydrous THF (15 mL) under N$_2$ at 0° C. The resultant solution was stirred at room temperature for 3.5 h and cooled to 0° C. Water (0.1 mL) was added to quench the reaction followed by aqueous NaOH (3 N, 2.6 mL) and 30% H$_2$O$_2$ (2.6 mL). The reaction mixture was stirred at ambient temperature overnight and extracted with EtOAc. The combined EtOAc extracts were washed with brine until neutral pH and then dried over Na$_2$SO$_4$. After solvent removal under reduced pressure, the residue 76 (a mixture of four diastereomers) was used without further purification or characterization.

Jones reagent was added dropwise to a solution of compound 76 in acetone (15 mL) at 0° C. until an orange color persisted. The resultant mixture was stirred at 0-5° C. for 10 min. 2-propanol was added to consume excess oxidant and the acetone was removed under reduced pressure. The residue obtained was dissolved in EtOAc (30 mL), washed with water to neutral pH, and dried over Na$_2$SO$_4$. The solvent was removed and the residue was purified by column chromatography (silica gel; hexanes/EtOAc, 10:1) to give a mixture of compound 77 and 78 (152 mg, 88%) in the ratio of 3:2. The compounds were further separated by column chromatography (silica gel; hexanes/EtOAc, 30:1).

Compound 77 was obtained as white solid: mp. 106-107° C.; $^1$H NMR δ 0.75 (s, 3H), 2.16 (s, 3H), 2.42 (bs, 1H), 3.36 (s, 3H), 3.82 (m,1H), 4.65 (m, 2H); $^{13}$C NMR δ 11.3, 18.1, 20.1, 21.6, 22.6, 23.8, 26.2, 27.7, 28.1, 28.5, 32.0, 32.8, 33.6, 33.9, 34.6, 35.9, 39.7, 41.6, 46.0, 49.6, 54.3, 55.1, 57.4, 71.6, 94.5, 211.6; IR $v_{max}$ 3400, 2928, 1708, 1041 cm$^{-1}$.

Compound 78 was obtained as white solid: mp. 103-105° C; $^1$H NMR δ 0.78 (s, 3H), 2.06 (m, 1H), 2.10 (s, 3H), 2.61 (m, 1H), 3.37 (s, 3H), 3.83 (m, 1H), 4.66 (m, 2H); $^{13}$C NMR δ 11.4, 20.2, 20.5, 21.6, 21.9, 22.4, 23.7, 26.3, 27.9, 28.5, 32.0, 32.9, 33.3, 33.6, 34.7, 36.0, 39.8, 42.6, 47.5, 49.4, 54.6, 55.1, 56.7, 71.6, 94.5, 211.8; IR $v_{max}$ 3392, 2923, 1707, 1041 cm$^{-1}$.

(3α,5α,20S)-1-[3-Hydroxy-13,24-cyclo-18,21-dinorcholan-20-yl]ethanone (79)

The mixture of compound 77 (32 mg, 80 μmol), LiBF$_4$ (64 mg, 0.68 mmol), H$_2$O (0.1 mL) and MeCN (3 mL) was refluxed for 3 h and cooled to room temperature. EtOAc (30 mL) was added and the solution was washed with water and brine and dried over Na$_2$SO$_4$. The solvent was removed and the residue was purified by column chromatography (silica gel; hexanes/EtOAc, 7:1) to give compound 79 (27 mg, 95%).

Compound 79 was obtained as white crystals: mp. 187-189° C. (acetone-hexanes); $^1$H NMR δ 0.75 (s, 3H), 2.16 (s, 3H), 2.42 (m, 1H), 4.03 (m, 1H); $^{13}$C NMR δ 11.1, 18.1, 20.1, 21.6, 22.6, 23.8, 27.7, 28.1, 28.5, 29.0, 32.0, 32.1, 33.9, 34.6, 35.8, 36.1, 39.1, 41.6, 46.0, 49.6, 54.3, 57.4, 66.5, 211.7; IR ν$_{max}$ 3401, 2928, 1705 cm$^{-1}$.

(3α,5α,20R)-1-[3-Hydroxy-13,24-cyclo-18,21-dinorcholan-20-yl]ethanone (80)

Using the same procedure described for the preparation of compound 79 from compound 77, compound 80 (29 mg, 93%) was prepared from compound 78 (35 mg, 87 μmol).

Compound 80 was obtained as white crystals: mp. 228-229° C. (EtOAc-hexanes); $^1$H NMR δ 0.78 (s, 3H), 1.83 (m, 1H), 2.05 (m, 1H), 2.10 (s, 3H), 2.62 (m, 1H), 4.04 (m, 1H); $^{13}$C NMR δ 11.2, 20.2, 20.5, 21.6, 21.9, 22.4, 23.7, 27.9, 28.5, 29.0, 32.1, 32.2, 33.3, 34.7, 35.9, 36.2, 39.2, 42.6, 47.5, 49.4, 54.6, 56.7, 66.5, 211.8; IR ν$_{max}$ 3401, 2927, 1699 cm$^{-1}$.

(3α,5α)-1-[3-Methoxymethoxy-13,24-cyclo-18,21-dinorchol-20(22)-en-20-yl]ethanone (82)

The mixture of compounds 77 and 78 (100 mg, 0.25 mmol) and NBS (73 mg, 0.41 mmol) in CCl$_4$ (15 mL) was refluxed under N$_2$ while being irradiated with a 300 W tungsten lamp for 20 min and then cooled to room temperature. The solvent was partially removed and the residue was purified by column chromatography (silica gel; hexanes/EtOAc, 20:1) to give compound 81 (80 mg, 67%) as a mixture of two diastereomers in the ratio of 1:1.

The mixture of compound 81 (80 mg, 0.17 mmol), Li$_2$CO$_3$ (160 mg, 2.16 mmol), and LiBr (80 mg, 0.93 mmol) in DMF (3 mL) was heated at 130° C. under N$_2$ for 2 h and cooled to room temperature. EtOAc (30 mL) was added and the mixture was washed with water, 3% HCl and water and dried over Na$_2$SO$_4$. The solvent was removed and the residue purified by column chromatography (silica gel; hexanes/EtOAc, 20:1) gave compound 82 (42 mg, 63%).

Compound 82 was obtained as white crystals: mp. 157-159° C. (hexanes); $^1$H NMR δ 0.80 (s, 3H), 2.27 (s, 3H), 3.37 (s, 3H), 3.83 (m, 1H), 4.66 (m, 2H), 6.78 (t, 1H, J=3.6 Hz); $^{13}$C NMR δ 11.5, 18.8, 20.0, 23.2, 24.6, 25.5, 26.3, 28.6, 30.5, 32.1, 32.8, 32.9, 33.6, 35.0, 36.0, 39.8, 41.0, 44.4, 54.5, 55.2, 55.5, 71.6, 94.5, 138.7, 143.7, 199.4; IR ν$_{max}$ 2928, 1667, 1435, 1042 cm$^{-1}$.

(3α,5α)-1-[3-Hydroxy-13,24-cyclo-18,21-dinorchol-20(22)-en-20-yl]ethanone (83)

Using the same procedure described for the preparation of compound 67 from compound 65, compound 83 (16 mg, 95%) was prepared from compound 82 (19 mg, 48 ∇mol).

Compound 83 was obtained as white solid: mp. 198-200° C. (ether-hexanes); $^1$H NMR δ 0.79 (s, 3H), 2.27 (s, 3H), 4.04 (m, 1H), 6.78 (t, 1H, J=3.9 Hz); $^{13}$C NMR δ 11.2, 18.8, 20.0, 23.2, 24.6, 25.5, 28.5, 29.0, 30.5, 32.1, 32.2, 32.8, 35.0, 35.9, 36.2, 39.2, 41.0, 44.4, 54.5, 55.5, 66.5, 138.7, 143.7, 199.4; IR ν$_{max}$ 3315, 2924, 1667, 1252 cm$^{-1}$.

(3β,5α)-3-Acetyloxy-21-diazopregnan-20-one (85)

Oxalyl chloride (0.12 mL, 1.38 mmol) was added to compound 84 (100 mg, 0.28 mmol) in benzene at 0° C. under N$_2$ and stirred at room temperature for 4 h. Removal of solvent under reduced pressure gave the acid chloride as a solid. It was used without further purification.

The acid chloride in ether (10 mL) was added to diazomethane (0.2 M in ether, 6 mL) dropwise at 0° C. and stirred at ambient temperature overnight. The solvent was removed under reduced pressure in a hood and the yellow residue obtained was purified by column chromatography (silica gel; hexanes/EtOAc, 10:1) to give compound 85 (84 mg, 79%).

Compound 85 was obtained as a yellow solid: mp. 135-136° C. (133-137° C. in Pettit noted below); $^1$H NMR δ 0.66 (s, 3H), 0.82 (s, 3H), 2.02 (s, 3H), 4.68 (m, 1H), 5.18 (s, 1H); $^{13}$C NMR δ 12.1, 13.3, 21.0, 21.4, 22.8, 24.4, 27.3, 28.4, 31.9, 33.9, 35.4 (2×C), 36.7, 38.6, 44.6, 44.8, 54.1, 54.7, 56.3, 61.4, 73.5, 170.6, 195.1; IR ν$_{max}$ 2937, 2099, 1731, 1637, 1367, 1246 cm$^{-1}$. (See also, Pettit, G. R., et al., *Steroids and Related Natural Products. LIV. Bufadienolides. 7. Synthesis of 3β-Acetoxy-5α-14α-bufa-20,22-dienolide*, J. Org. Chem. 1970, 35, 1398-1404).

(3β,5α)-3-Acetyloxy-18,21-cyclopregnan-20-one (86)

Compound 85 (600 mg, 1.55 mmol) in CH$_2$Cl$_2$ (10 mL) was added to Rh$_2$(OCOCF$_3$)$_4$ in CH$_2$Cl$_2$ (50 mL) and stirred at room temperature for 10 min. Most solvent was removed under reduced pressure and the residue purified by column chromatography (silica gel; hexanes/EtOAc, 10:1) gave compound 86 (300 mg, 54%).

Compound 86 was obtained as white crystals: mp. 146-148° C.; $^1$H NMR δ 0.82 (s, 3H), 2.02 (s, 3H), 4.69 (m, 1H); $^{13}$C NMR δ 12.2, 21.4, 21.6, 24.2, 26.2, 27.4, 27.7, 28.3, 32.1, 33.9, 34.3, 35.5, 35.7, 36.8, 37.0, 44.5, 51.9, 53.5, 55.5, 58.5, 73.5, 170.7, 222.6; IR ν$_{max}$ 2933, 1733, 1244, 1027 cm$^{-1}$.

(3β,5α)-3-Hydroxy-18,21-cyclopregnan-20-one (87)

Compound 86 (300 mg, 0.84 mmol) was dissolved in MeOH (20 mL) and 20% aqueous NaOH (1.0 mL) was added. The solution was refluxed for 20 min and cooled to room temperature. MeOH was removed under reduced pressure and EtOAc (50 mL) was added. The organic layer was washed with water and dried over Na$_2$SO$_4$. Solvent removal under reduced pressure gave a residue that was purified by column chromatography (silica gel; hexanes/EtOAc, 5:1) to give compound 87 (250 mg, 94%).

Compound 87 was obtained as white crystals: mp. 182-184° C.; $^1$H NMR δ 0.80 (s, 3H), 3.59 (m, 1H); $^{13}$C NMR δ 12.2, 21.6, 24.1, 26.2, 27.6, 28.4, 31.3, 32.2, 34.3, 35.5, 35.6, 36.9, 36.9, 38.0, 44.7, 51.8, 53.5, 55.5, 58.4, 71.0, 222.6; IR ν$_{max}$ 3413, 2923, 1721, 1447, 1042 cm$^{-1}$.

(3α,5α)-3-Benzoyloxy-18,21-cyclopregnan-20-one (88)

DEAD (40% solution in toluene) was added dropwise to the mixture of compound 87 (250 mg, 0.79 mmol), Ph$_3$P (250 mg, 0.95 mmol) and PhCO$_2$H (116 mg, 0.95 mmol) in THF (20 mL) until the yellow color persisted. The yellowish solution was stirred at room temperature for 2 h and most of THF was removed under reduced pressure. The residue obtained was purified by column chromatography (silica gel; hexanes/EtOAc, 10:1) to give compound 88 (290 mg, 87%).

Compound 88 was obtained as white solid: mp. 201-204° C.; $^1$H NMR δ 0.85 (s, 3H), 5.29 (m, 1H), 7.46 (t, 2H, J=7.2 Hz), 7.57 (t, 1H, J=7.2 Hz), 8.07 (d, 2H, J=7.2 Hz); $^{13}$C NMR δ 11.4, 21.2, 24.2, 26.2, 26.2, 27.7, 28.1, 32.1, 32.9, 33.2, 34.3, 35.7, 35.9, 37.0, 40.3, 51.9, 53.6, 55.6, 58.5, 70.5, 128.3 (2×C), 129.5 (2×C), 131.1, 132.7, 165.8, 222.5; IR $\nu_{max}$ 2930, 1735, 1714, 1450, 1272, 1113, 714 cm$^{-1}$.

(3α,5α)-3-Hydroxy-18,21-cyclopregnan-20-one (89)

Compound 88 (290 mg, 0.69 mmol) was dissolved in EtOH (20 mL) and 20% aqueous NaOH (0.8 mL) was added. The solution was refluxed for 20 min and cooled to room temperature. EtOH was removed under reduced pressure and EtOAc (50 mL) was added. The organic layer was washed with water and dried over Na$_2$SO$_4$. Solvent removal under reduced pressure gave a residue that was purified by column chromatography (silica gel; hexanes/EtOAc, 5:1) to give compound 89 (210 mg, 96%).

Compound 89 was obtained as white crystals: mp. 176-178.5° C. (EtOAc-hexanes); $^1$H NMR δ 0.78 (s, 3H), 4.05 (m, 1H); $^{13}$C NMR δ 11.2, 21.2, 24.2, 26.2, 27.7, 28.3, 28.9, 32.2 (2×C), 34.4, 35.7, 35.8, 36.1, 37.0, 39.0, 51.9, 53.6, 55.7, 58.5, 66.4, 222.7; IR $\nu_{max}$ 3307, 2923, 1736, 1448 cm$^{-1}$.

(3α,5α)-3-Hydroxy-18,21-cyclopregn-18(21)-en-20-one (94) and (3α,5α)-21-bromo-3-hydroxy-18,21-cyclopregn-18(21)-en-20-one (95)

The mixture of compound 88 (168 mg, 0.40 mmol) and pyridinium tribromide (180 mg, 0.56 mmol) in THF (20 mL) was stirred at room temperature for 1.5 h. The solvent was removed under reduced pressure and EtOAc (20 mL) was added. The EtOAc solution was washed with water, 5% Na$_2$S$_2$O$_3$ and water and dried over Na$_2$SO$_4$. Solvent removal under reduced pressure gave a residue that was passed through a short column (silica gel; hexanes/EtOAc, 5:1) to give a mixture of 21-bromo-20-one (90) and 21,21-dibromo-20-one (91). The mixture of compounds was used without further separation.

The mixture of compounds 90 and 91 (160 mg, 0.32 mmol), Li$_2$CO$_3$ (300 mg), LiBr (150 mg) in DMF (5 mL) was stirred at 130° C. for 6 h and cooled to room temperature. EtOAc (50 mL) was added and the organic layer was washed with water, 5% HCl and water and dried over Na$_2$SO$_4$. After the solvent was removed under reduced pressure, the residue was separated by column chromatography (silica gel; hexanes/EtOAc, 12:1) to give partially purified compound 92 (34 mg, 25%) and compound 93 (55 mg, 41%).

Using the same procedure described for the preparation of compound 89 from compound 88, compound 94 (22 mg, 86%) was prepared from compound 92 (34 mg, 81 μmol) and compound 95 (32 mg, 77%) was prepared from compound 93 (55 mg, 131 μmol).

Compound 94 was obtained as white crystals: mp. 139-141° C. (EtOAc-hexanes); $^1$H NMR δ 0.86 (s, 3H), 2.31 (d, 1H, J=11.1 Hz), 4.07 (m, 1H), 6.19 (d, 1H, J=6.0 Hz), 7.73 (d, 1H, J=6.0 Hz); $^{13}$C NMR δ 11.2, 21.9, 26.0, 28.3, 28.8, 29.0, 32.1, 32.3, 35.7, 35.8, 36.0, 36.3, 39.0, 54.0, 54.2, 54.6, 57.4, 66.3, 134.7, 167.3, 212.4; IR $\nu_{max}$ 3412, 2926, 1709, 1448 cm$^{-1}$.

Compound 95 was obtained as white crystals: mp. 220-222.5° C. (EtOAc-hexanes); $^1$H NMR δ 0.87 (s, 3H), 2.49 (d, 1H, J=11.4 Hz), 4.08 (m, 1H), 7.81 (s, 1H); $^{13}$C NMR δ 11.3, 21.9, 26.0, 28.2, 29.0 (2×C), 32.1, 32.2, 35.7, 35.7, 35.8, 36.3, 38.9, 53.2, 54.1 (2×C), 57.0, 66.3, 125.6, 164.7, 203.7; IR $\nu_{max}$ 3538, 2919, 1717, 1446 cm$^{-1}$. MS (ESI) m/z 415 (M$^+$+Na$^+$), 417 (M$^+$+2+Na$^+$).

(3α,5α,20E)-3-Hydroxy-18,21-cyclopregnan-20-ylideneacetonitrile (96) and (3α,5α,20Z)-3-Hydroxy-18,21-cyclopregnan-20-ylideneacetonitrile (97)

Using the same procedure described for the preparation of compound 63 and 64 from compound 2a, compound 96 (39 mg, 48%) and 97 (32 mg, 40%) was prepared from compound 89 (75 mg, 0.24 mmol). Compounds 96 and 97 were separated by column chromatography (silica gel; CH$_2$Cl$_2$/EtOAc, 30:1).

Compound 96 was obtained as white crystals: mp. 201-202.5° C. (acetone-hexanes); $^1$H NMR δ 0.76 (s, 3H), 2.05 (m, 1H), 2.46 (m, 1H), 2.67 (m, 2H), 4.05 (m, 1H), 5.12 (s, 1H); $^{13}$C NMR δ 11.2, 21.5, 26.1, 27.3, 28.3, 29.0, 31.8, 31.9, 32.2 (2×C), 34.7, 35.8, 36.1, 37.0, 39.0, 53.6, 55.2, 55.3, 56.4, 66.4, 89.9, 117.5, 178.7; IR $\nu_{max}$ 3306, 2927, 2214, 1634, 1448 cm$^{-1}$.

Compound 97 was obtained as white crystals: mp. 226-228° C. (acetone-hexanes); $^1$H NMR δ 0.75 (s, 3H), 2.28 (m, 1H), 2.53 (m, 2H), 2.77 (m, 1H), 4.04 (m, 1H), 5.09 (d, 1H, J=1.8 Hz); $^{13}$C NMR δ 11.2, 21.5, 26.0, 27.5, 28.3, 28.9, 30.9, 32.2 (2×C), 32.8, 34.6, 35.8, 36.1, 37.0, 39.0, 53.6, 54.9, 55.2, 55.3, 66.4, 89.7, 117.7, 179.0; IR $\nu_{max}$ 3401, 2922, 2215, 1446 cm$^{-1}$.

Physical Properties and Spectroscopic Data for Evaluated Compounds in the 5β-Series (3α,5β)-3-Hydroxy-13,24-cyclo-18,21-dinorcholan-20-one (2b)

Compound 2b was obtained as white crystals: mp 220-222° C. (EtOAc-hexanes); $^1$H NMR δ 0.93 (s, 3H, 19-CH$_3$), 2.50 (m, 1H, CHCO), 3.63 (m, 1H, CHOH); $^{13}$C NMR δ 20.3, 22.1 (2×C), 23.3, 25.1, 26.7, 27.0, 27.1, 30.5, 33.7, 34.6, 35.4, 35.5, 36.3, 37.3, 40.2, 42.0, 49.6, 56.7, 61.5, 71.6, 215.5 (CO); IR $\nu_{max}$ 3449, 2921, 1698, 1460, 1037 cm$^{-1}$. Anal. (C$_{22}$H$_{34}$O$_2$) C, H.

(3α,5β)-3-Hydroxy-13,24-cyclo-18,21-dinorcholan-22-one (3b)

Compound 3b was obtained as white crystals: mp 175-177° C. (EtOAc-hexanes); $^1$H NMR δ 0.93 (s, 3H, 19-CH$_3$), 2.38 (m, 1H, CH$_2$CO), 2.54 (dd, J=6.0 Hz, J=14.4 Hz,1H, CH$_2$CO), 3.65 (m, 1H, CHOH); $^{13}$C NMR δ 20.4, 23.3 (2×C), 23.6, 26.4, 27.0, 27.7, 30.4, 32.8, 34.6, 35.4, 35.9, 36.3, 36.9, 40.6, 41.2, 41.5, 42.0, 49.0, 55.5, 71.6, 213.4 (CO); IR $\nu_{max}$ 3418, 2936, 1714, 1447 cm$^{-1}$. Anal. (C$_{22}$H$_{34}$O$_2$) C, H.

(3α,5β)-3-Hydroxy-13,24-cyclo-18,21-dinorcholan-23-one (4b)

Compound 4b was obtained as white crystals: mp 197-198° C. (Ether-hexanes); 1H NMR δ 0.91 (s, 3H, 19-CH$_3$), 2.50 (m, 1H, CH$_2$CO), 3.64 (m, 1H, CHOH); $^{13}$C NMR δ 19.8, 23.4, 24.4, 24.9, 25.2, 26.4, 26.9, 30.5, 34.4, 34.7, 35.2, 35.3, 36.3, 36.5, 40.5 (2×C), 42.0, 44.7, 48.9, 56.3, 71.7, 213.7 (CO); IR $\nu_{max}$ 3398, 2927, 1709, 1448, 1039 cm$^{-1}$. Anal. (C$_{22}$H$_{34}$O$_2$) C, H.

(3α,5β)-3-Hydroxy-13,24-cyclo-18,21-dinorcholan-24-one (5b)

Compound 5b was obtained as white crystals: mp 177-178° C. (Et$_2$O-hexanes); $^1$H NMR δ 0.89 (s, 3H, 19-CH$_3$), 3.64 (m, 1H, CHOH); $^{13}$C NMR δ 21.7, 23.6, 23.9 (2×C), 24.0, 25.5, 27.0, 27.1, 30.5, 34.7, 35.3, 35.4, 35.6, 36.5, 40.2, 41.1, 42.2, 49.8, 56.4, 58.5, 71.8, 216.6 (CO); IR ν$_{max}$ 3334, 2937, 1701, 1450, 1037 cm$^{-1}$. Anal. (C$_{22}$H$_{34}$O$_2$).

(3α,5β)-3-(Acetyloxy)-20-hydroxypregnane-20-carbonitrile (7b)

Compound 7b was prepared using a reported method (See, Slomp, G., Jr. 3,20-Dioxo-Δ$^4$-steriod 20-cyanohydrins. U.S. Pat. No. 2,655,517, 1953. Chem. Abstr. 48:60638) and was obtained as a white solid: mp 168-178° C.; $^1$H NMR δ 0.95 (s, 3H, 19-CH$_3$), 0.99 (s, 3H, 18-CH$_3$), 1.63 (s, 3H, 21-CH$_3$), 2.03 (s, 3H, CH$_3$C(O)O), 4.73 (m, 1H, CHOAc); $^{13}$C NMR δ 13.0, 20.5, 21.4, 23.3, 24.1, 25.1, 26.2, 26.6, 26.9, 30.7, 32.2, 34.6, 35.0, 35.2, 40.3, 40.4, 41.8, 43.6, 55.9, 59.2, 71.7, 74.3, 121.9 (CN), 170.6 (C(O)O).

(3α,5β)-3-(Acetyloxy)-20-oxo-pregnane-18-carbonitrile (8b)

Compound 8b was obtained as a colorless oil: $^1$H NMR δ 0.94 (s, 3H, 19-CH$_3$), 2.04 (s, 3H, CH$_3$C(O)O), 2.29 (s, 3H, CH$_3$CO), 2.72 (t, J=9.3 Hz, 1H, CHCOCH$_3$), 4.73 (m, 1H, CHOAc); $^{13}$C NMR δ 16.3, 20.6, 21.3, 23.1, 23.2, 23.9, 26.0, 26.5, 26.6, 32.1, 32.4, 34.4, 34.8, 35.8, 36.1, 40.1, 41.4, 46.1, 56.3, 62.0, 73.8, 118.0 (CN), 170.4 (C(O)O), 208.6 (CO).

(3α,5β)-3-(Acetyloxy)-20,20-[1,2-ethanediylbis(oxy)]pregnane-18-carbonitrile (9b)

Compound 9b was obtained as white crystals: mp 138-140° C.; $^1$H NMR δ 0.94 (s, 3H, 19-CH$_3$), 1.29 (s, 3H, 21-CH$_3$), 2.03 (s, 3H, CH$_3$C(O)O), 2.24 (d, J=16.8 Hz, 1H, CH$_2$CN), 2.51 (d, J=16.8 Hz, 1H, CH$_2$CN), 4.04 (m, 4H, OCH$_2$CH$_2$O), 4.72 (m, 1H, CHOAc); $^{13}$C NMR δ 16.7, 20.5, 21.4, 23.2, 23.2, 23.3, 23.5, 25.9, 26.6, 26.8, 32.2, 34.5, 34.9, 35.5, 36.8, 40.3, 41.6, 43.8, 56.1, 56.5, 63.1, 63.8, 74.1, 110.8 (20-C), 119.8 (CN). 170.5 (C(O)O).

(3α, 5β)-3-Hydroxy-13,24-cyclo-18,21-dinorchol-22-en-20-one (11b)

Compound 11b was obtained as white crystals: mp 253-254° C. (EtOAc); $^1$H NMR δ 0.93 (s, 3H, 19-CH$_3$), 3.63 (m, 1H, CHOH), 5.96 (dd, J=3.0 Hz, J=9.9 Hz, 1H, =CHCO), 6.83 (m, 1H, =CHCH$_2$); $^{13}$C NMR δ 20.3, 23.3, 25.8, 26.3, 26.5, 26.9, 27.3, 30.5, 34.1, 34.6, 35.3, 35.6, 36.3, 40.1, 42.0, 47.6, 56.2, 57.8, 71.6, 127.4 (=CHCO), 148.3 (=CHCH$_2$), 202.2 (CO); IR ν$_{max}$ 3430, 2921, 1663, 1038 cm$^{-1}$. Anal. (C$_{22}$H$_{32}$O$_2$) C, H.

(3α,5β)-13,24-Cyclo-18,21-dinorchol-20(22)-en-3-ol (13b)

Compound 13b was obtained as white crystals: mp 168-169° C. (hexanes); $^1$H NMR δ 0.94 (s, 3H, 19-CH$_3$), 3.63 (m, 1H, CHOH), 5.54 (m, 1H, CH=), 5.76 (m, 1H, CH=); $^{13}$C NMR δ 20.0, 20.2, 21.6, 23.4, 24.8, 26.7, 27.2, 30.6, 30.6, 33.4, 34.7, 35.1, 35.5, 36.5, 40.8, 41.0, 42.2, 46.6, 56.1, 71.8, 124.4 (CH=), 130.8 (CH=).

(3α,5β)-3-Methoxymethoxy-13,24-cyclo-18,21-dinorchol-20(22)-ene (14b)

Compound 14b was obtained as a colorless oil: $^1$H NMR δ 0.93 (s, 3H, 19-CH$_3$), 3.37 (s, 3H, OCH$_3$), 3.53 (m, 1H, CHOCH$_2$O), 4.69 (s, 2H, OCH$_2$O), 5.54 (m, 1H, CH=), 5.75 (m, 1H, CH=); $^{13}$C NMR δ 19.7, 20.1, 21.6, 23.4, 24.7, 26.7, 27.2, 27.7, 30.6, 33.3, 33.6, 34.8, 35.0, 35.4, 40.7, 40.9, 42.2, 46.6, 55.1, 56.1, 76.8, 94.5 (OCH$_2$O), 124.4 (CH=), 130.7 (CH=).

(3α,5β)-3-Hydroxy-13,24-cyclo-18,21-dinorchol-20(22)-en-23-one (22c)

Compound 22c was obtained as white crystals: mp 209-211° C. (EtOAc-hexanes); $^1$H NMR δ 0.92 (s, 3H, 19-CH$_3$), 2.35 (d, J=15.9 Hz, 1H, CCH$_2$CO), 3.64 (m, 1H, CHOH), 5.90 (d, J=9.6 Hz, 1H, =CHCO), 6.96 (m, 1H, =CHCH); $^{13}$C NMR δ 19.7, 23.3, 26.3, 26.4, 26.9, 29.4, 30.4, 34.4, 34.6, 35.1, 35.3, 36.3, 37.9, 40.4, 42.0, 47.3, 47.4, 56.0, 71.6, 127.1 (=CHCO), 152.0 (=CHCH), 200.2 (CO); IR ν$_{max}$ 3446, 2932, 1677, 1451, 1042 cm$^{-1}$. Anal. (C$_{22}$H$_{32}$O$_2$) C, H.

(3α,5β)-13,24-Cyclo-18,21-dinorchola-20(22),23-diene-3,20-diol, 3,20-diacetate (23b)

Compound 23b was obtained as white crystals: mp 138-139° C.; $^1$H NMR δ 0.96 (s, 3H, 19-CH$_3$), 2.03 (s, 3H, CHOC(O)CH$_3$), 2.15 (s, 3H, =CHOC(O)CH$_3$), 4.74 (m, 1H, CHOAc), 5.56 (d, J=5.7 Hz, 1H, CH=COAc), 5.62 (d, J=9.9 Hz, 1H, CH=CHCH=), 5.84 (dd, J=5.7 Hz, J=9.9 Hz, 1H, CH=CHCH=); $^{13}$C NMR δ 20.1, 21.2, 21.4, 23.3, 26.6, 26.7, 27.0, 29.7, 32.2, 32.4, 34.7, 35.1, 36.3, 37.6, 40.5, 41.8, 47.9, 48.4, 56.1, 74.2, 107.8 (CH=COAc), 122.4 (=CHCH=COAc), 127.5 (CCH=CH), 154.5 (=COAc), 169.0 (CHOC(O)CH$_3$), 170.5 (=COC(O)CH$_3$).

(3α,5β,20R)-13,24-Cyclo-18,21-dinorchol-23-en-3,20-diol, 3-acetate (25a)

Compound 25a was obtained as a colorless oil: $^1$H NMR δ 0.96 (s, 3H, 19-CH$_3$), 2.04 (s, 3H, CH$_3$C(O)O), 4.11 (m, 1H, CHOH), 4.74 (m, 1H, CHOAc), 5.54 (m, 1H, CH$_2$CH=), 5.63 (d, J=10.2 Hz, 1H, CCH=); $^{13}$C NMR δ 20.6, 20.8, 21.4, 23.3, 25.9, 26.6, 26.7, 26.9, 30.7, 32.3, 34.8, 35.1, 35.7, 38.7, 40.8, 41.9, 48.0, 51.1, 55.1, 66.9, 74.3, 124.8 (CH=), 129.5 (CH=), 170.6 (C(O)O).

(3α,5β,20S)-13,24-Cyclo-18,21-dinorchol-23-en-3,20-diol, 3-acetate (25b)

Compound 25b was obtained as a colorless oil: $^1$H NMR δ 0.97 (s, 3H, 19-CH$_3$), 2.04 (s, 3H, CH$_3$C(O)O), 4.07 (m, 1H, CHOH), 4.74 (m, 1H, CHOAc), 5.65 (m, 1H, CH$_2$CH=), 5.84 (d, J=10.8 Hz, 1H, CCH=); $^{13}$C NMR δ 20.8, 21.4, 23.3, 25.9, 26.1, 26.6, 26.7, 27.0, 30.0, 32.3, 34.7, 35.0, 35.3, 39.9, 40.5, 41.8, 42.9, 50.1, 55.7, 68.4, 74.3, 124.1 (CH=), 129.6 (CH=), 170.6 (C(O)O).

(3α,5β)-3-(Acetyloxy)-13,24-cyclo-18,21-dinorchol-23-ene (28b)

Compound 28b was obtained as a colorless oil: $^1$H NMR δ 0.96 (s, 3H, 19-CH$_3$), 2.03 (s, 3H, CH$_3$C(O)O), 4.73 (m, 1H, CHOAc), 5.66 (bs, 2H, CH=CH); $^{13}$C NMR δ 20.5, 20.8, 21.2, 21.4, 23.3, 24.6, 26.2, 26.6, 26.7, 27.0, 32.2, 34.7, 35.1, 35.4, 38.6, 40.8, 41.9, 43.4, 43.8, 55.1, 74.3, 128.0 (CH=), 129.5 (CH=), 170.5 (C(O)O).

(3α,5β)-3-(Acetyloxy)-13,24-cyclo-18,21-dinorchol-23-en-22-one (29b)

Compound 29b was obtained as a white solid (contaminated with 10% unidentified impurity): $^1$H NMR δ 1.00 (s, 3H, 19-CH$_3$), 2.04 (s, 3H, CH$_3$C(O)O), 2.41 (dm, J=17.1 Hz, 1H, CH$_2$CO), 2.64 (dd, J=4.2 Hz, J=17.1 Hz, 1H, CH$_2$CO), 4.75 (m, 1H, CHOAc), 6.00 (d, J=10.5 Hz, 1H, =CHCO), 6.94 (dd, J=2.1 Hz, J=10.5 Hz, 1H, =CHC); $^{13}$C NMR δ 20.8, 21.4, 23.3, 26.4, 26.6, 26.7, 26.8, 27.6, 32.2, 34.7, 35.1, 35.7, 36.6, 38.2, 40.6, 41.8, 44.0, 45.6, 56.8, 74.1, 130.1 (=CHCO), 152.1 (=CHC), 170.5 (C(O)O), 199.7 (CO).

(3α,5β)-3-Hydroxy-13,24-cyclo-18,21-dinorchol-23-en-22-one (30b)

Compound 30b was obtained as white crystals: mp 196.5-199° C.; $^1$H NMR δ 0.99 (s, 3H, 19-CH$_3$), 2.41 (dm, J=17.1 Hz, 1H, CH$_2$CO), 2.64 (dd, J=4.2 Hz, J=17.1 Hz, 1H, CH$_2$CO), 3.67 (m, 1H, CHOH), 6.00 (d, J=10.5 Hz, 1H, =CHCO), 6.95 (dd, J=2.1 Hz, J=10.5 Hz, 1H, =CHC); $^{13}$C NMR δ 20.8, 23.3, 26.5, 26.8, 27.0, 27.7, 30.5, 34.7, 35.4, 35.7, 36.4, 36.6, 38.2, 40.7, 42.0, 44.0, 45.6, 56.9, 71.6, 130.1 (=CHCO), 152.3 (=CHC), 199.8 (CO); IR ν$_{max}$ 3412, 2933, 1677, 1038 cm$^{-1}$. Anal. (C$_{22}$H$_{32}$O$_2$).

(3α,5β,23R,24S)-23,24-Epoxy-13,24-cyclo-18,21-dinorcholan-3-ol, acetate (31b)

Compound 31b was obtained as a white solid: mp 125-129° C.; $^1$H NMR δ 0.95 (s, 3H, 19-CH$_3$), 2.03 (s, 3H, CH$_3$C(O)O), 2.94 (d, J=3.9 Hz, 1H, epoxy 24-H), 3.16 (m, 1H, epoxy 23-H), 4.74 (m, 1H, CHOAc); $^{13}$C NMR δ 18.2, 19.3, 21.2, 21.4, 23.3, 24.6, 26.2, 26.6, 26.7, 26.9, 32.2, 34.7, 34.9 (2×C), 35.0, 40.7, 40.8, 41.4, 41.8, 54.2, 54.5, 55.8, 74.3, 170.5 (C(O)O).

(3α,5β,23S,24S)-23-Bromo-13,24-cyclo-18,21-dinorcholan-3,24-diol, 3-acetate (32b)

Compound 32b was obtained as a white solid: mp 134-136.5° C.; $^1$H NMR δ 0.91 (s, 3H, 19-CH$_3$), 2.03 (s, 3H, CH$_3$C(O)O), 3.64 (dd, J=1.8 Hz, J=10.5 Hz, 1H, CHOH), 4.32 (m, 1H, CHBr), 4.73 (m, 1H, CHOAc); $^{13}$C NMR δ 21.4, 22.6, 23.3, 23.4, 24.9, 24.9, 26.7, 26.9, 27.0, 31.9, 32.3, 33.1, 34.9, 35.2, 35.7, 40.7, 42.1, 47.8, 48.3, 58.3, 63.6, 74.4, 74.5, 170.6 (C(O)O).

(3α,5β,23S)-3-(Acetyloxy)-23-bromo-13,24-cyclo-18,21-dinorcholan-24-one (33b)

Compound 33b was obtained as a white solid: mp 222-225° C.; $^1$H NMR δ 0.91 (s, 3H, 19-CH$_3$), 2.03 (s, 3H, CH$_3$C(O)O), 4.72 (m, 1H, CHOAc), 4.90 (dd, J=6.3 Hz, J=13.2 Hz, 1H, CHBr); $^{13}$C NMR δ 21.4, 21.8, 23.6, 23.7, 25.2, 25.6, 26.7, 26.8, 26.9, 32.3, 34.7, 35.1, 35.4, 35.6, 36.3, 41.1, 41.9, 49.5, 56.2, 57.1, 59.9, 74.3, 170.5 (C(O)O), 204.9 (CO).

(3α,5β)-3-(Acetyloxy)-13,24-cyclo-18,21-dinorchol-22-en-24-one (34b)

Compound 34b was obtained as white crystals: mp 146-148° C.; $^1$H NMR δ 1.01 (s, 3H, 19-CH$_3$), 2.03 (s, 3H, CH$_3$C(O)O), 4.74 (m, 1H, CHOAc), 5.80 (dd, J=2.7 Hz, J=10.2 Hz, 1H, =CHCO), 6.63 (m, 1H, =CHCH$_2$); $^{13}$C NMR δ 20.3, 21.4, 23.6, 24.4, 26.7 (2×C), 26.9, 27.0, 27.8, 32.4, 32.8, 34.8, 35.2, 35.7, 40.5, 42.1, 45.2, 53.5, 57.2, 74.5, 129.4 (=CHCO), 144.5 (=CHCH$_2$), 170.5 (C(O)O), 203.8 (CO).

(3α,5β)-3-Hydroxy-13,24-cyclo-18,21-dinorchol-22-en-24-one (35b)

Compound 35b was obtained as white crystals mp 222-223° C. (EtOAc-hexanes); $^1$H NMR δ 1.00 (s, 3H, 19-CH$_3$), 3.65 (m, 1H, CHOH), 5.80 (dd, 1H, J=3.0 Hz, J=10.2 Hz, =CHCO), 6.62 (m, 1H, =CHCH$_2$); $^{13}$C NMR δ 20.3, 23.6, 24.4, 26.7, 27.1 (2×C), 27.8, 30.6, 32.9, 34.8, 35.5, 35.7, 36.5, 40.5, 42.2, 45.2, 53.5, 57.2, 71.8, 129.4 (=CHCO), 144.5 (=CHCH$_2$), 204.0 (CO); IR ν$_{max}$ 3418, 2861, 1661, 1038 cm$^{-1}$. Anal. (C$_{22}$H$_{32}$O$_2$).

EXAMPLE 26

[$^{35}$S]-TBPS Binding Methods

Rat brain cortical membranes were prepared with minor modifications of the method previously reported. (Hawkinson, J. E., et al., *Correlation of Neuroactive Steroid Modulation of [$^{35}$S]t-Butylbicyclophosophorothionate and [$^3$H] Flunitrazepam Binding and γ-Aminobutyric Acid$_A$ Receptor Function, Mol. Pharmacol.*, 1994, 46, 977-985). Briefly, frozen rat cerebral cortices (Pel-freez, Rogers, Ak.) were thawed and homogenized in 10 volumes of ice-cold 0.32 M sucrose using a glass/Teflon pestle. The homogenate was centrifuged at 1500×g for 10 min at 4° C. The resultant supernatant was centrifuged at 10,000×g for 30 min at 4° C. The pellet (P2) from this centrifugation was resuspended in 200 mM NaCl, 50 mM potassium phosphate buffer, pH 7.4, and centrifuged at 10,000×g for 20 min at 4° C. This washing procedure was done a total of three times, and then pellets were resuspended in buffer (~4 mL/brain) using a glass/Teflon pestle. The membrane suspension was aliquoted, frozen in liquid nitrogen, and stored at –80° C. prior to use.

[$^{35}$S]-TBPS Binding assays were done according to the procedure described previously (Hawkinson, J. E., et al., *Correlation of Neuroactive Steroid Modulation of [$^{35}$S]t-Butylbicyclophosophorothionate and [$^3$H]Flunitrazepam Binding and γ-Aminobutyric Acid$_A$ Receptor Function, Mol. Pharmacol.*, 1994, 46, 977-985) with modifications. Briefly, aliquots of membrane solution (0.5 mg/mL final protein concentration in assay) were incubated with 5 μM GABA, 2 nM [$^{35}$S]-TBPS (45-120 Ci/mmol), and 5 μL aliquots of steroid in DMSO solution (final assay concentrations ranged from 1 nM to 10 μM), and brought to a final volume of 1 mL with 200 mM NaCl, 50 mM potassium phosphate buffer, pH 7.4. Control binding was defined as binding observed in the presence of 0.5% DMSO and the absence of steroid. Nonspecific binding was defined as binding observed in the presence of 200 μM picrotoxinin and ranged from 6.1 to 14.3% of total binding. Assay tubes were incubated for 2 hr at room temperature. A Brandel (Gaithersburg, Md.) cell harvester was used for filtration of the assay tubes through Whatman/GF/C glass filter paper. Filter paper was rinsed with 4 mL of ice-cold buffer three times. Radioactivity bound to the filters was read by liquid scintillation counter and data was fit using Sigma Plot version 3.0 to the Hill equation i. $f = R_{max} / \{1 + ([conc]/IC_{50})^n\}$ Where $R_{max}$ is the maximal effect, [conc] is steroid concentration, $IC_{50}$ is the half-maximal inhibitor concentration and n is the Hill coefficient. Each data point was determined in triplicate and 2-3 full concentration-response curves were generated for each steroid.

TABLE 1

Displacement of [$^{35}$S]-TBPS binding by Cyclosteroids.

| Compound | IC$_{50}$ (nM)[a] | nHill |
|---|---|---|
| 5α-Steroids | | |
| 1a; 20-oxo | 74 ± 7 | 0.89 ± 0.06 |
| 5a; 24-oxo | 301 ± 20 | 1.01 ± 0.06 |
| 4a; 23-oxo | 334 ± 17 | 1.14 ± 0.05 |
| 2a; 20-oxo | 514 ± 64 | 0.84 ± 0.08 |
| 3a; 22-oxo | 1,440 ± 100 | 0.95 ± 0.06 |
| 35a; Δ$^{22}$-24-one | 197 ± 23 | 1.03 ± 0.10 |
| 21c; Δ$^{20(22)}$-23-one | 243 ± 11 | 0.89 ± 0.03 |
| 11a; Δ$^{22}$-20-one | 373 ± 20 | 1.17 ± 0.06 |
| 30a; Δ$^{23}$-22-one | 1260 ± 100 | 1.00 ± 0.07 |
| 19a; (22S,23S)-epoxy-20-one | 370 ± 42 | 0.97 ± 0.09 |
| 19b; (22R,23R)-epoxy-20-one | 313 ± 18 | 1.10 ± 0.06 |
| 39; 20-CN (eq) | 1670 ± 138 | 1.16 ± 0.10 |
| 40; 20-CN (ax) | 173 ± 12 | 0.97 ± 0.06 |
| 44; 22-CN (eq) | 585 ± 30 | 0.86 ± 0.03 |
| 45; 22-CN (ax) | 44300 ± 21300 | 0.42 ± 0.11 |
| 49; 23-CN (ax) | 574 ± 26 | 1.20 ± 0.06 |
| 50; 23-CN (eq) | 482 ± 20 | 1.09 ± 0.04 |
| 13a; Δ$^{20(22)}$-ene | 569 ± 28 | 1.15 ± 0.05 |
| 51; 20-[exo-CH$_2$] | 181 ± 9 | 0.96 ± 0.04 |
| 53; 22-[exo-CH$_2$] | 107000 ± 29600 | 0.47 ± 0.06 |
| 57; Δ$^{20(22)}$-20-CN | 433 ± 30 | 1.05 ± 0.06 |
| 60; Δ$^{20(22),23}$-diene | 467 ± 26 | 1.04 ± 0.05 |
| 61; Δ$^{23}$-ene* | 2000 ± 190 | 0.94 ± 0.08 |
| 63; exo-[CHCN] | 11 ± 1.8 | 0.90 ± 0.08 |
| 64; exo-[CHCN] | 1,080 ± 136 | 1.10 ± 0.14 |
| 67; 20-OH (ax) | 613 ± 92 | 0.83 ± 0.09 |
| 68; 20-OH (eq) | 1,540 ± 320 | 0.68 ± 0.09 |
| 69; 20-OMe (ax) | 353 ± 38 | 1.07 ± 0.10 |
| 70; 20-OMe (eq) | 868 ± 78 | 1.15 ± 0.10 |
| 71; (20R,22S)-epoxide | 596 ± 71 | 1.06 ± 0.11 |
| 72; (20S,22R)-epoxide | 323 ± 25 | 0.92 ± 0.05 |
| 73; exo-(20S)-epoxide | 1,290 ± 83 | 1.66 ± 0.16 |
| 74; exo-(20R)-epoxide | 64 ± 9 | 0.99 ± 0.11 |
| 79; 20-(acetyl) (ax) | 93 ± 9 | 1.07 ± 0.09 |
| 80; 20-(acetyl) (eq) | 2,060 ± 340 | 0.91 ± 0.13 |
| 83; Δ$^{20(22)}$-20-(acetyl) | 3,190 ± 398 | 1.64 ± 0.31 |
| 89; 20-one | 204 ± 36 | 0.82 ± 0.10 |
| 94; Δ$^{18(21)}$-20-one | 745 ± 75 | 0.86 ± 0.07 |
| 95; Δ$^{18(21)}$-20-one, 21-Br | 94 ± 17 | 1.05 ± 0.16 |
| 96; exo-[CHCN] | 168 ± 32 | 0.90 ± 0.13 |
| 97; exo-[CHCN] | 17,200 ± 6,190 | 0.44 ± 0.10 |
| 5β-Steroids | | |
| 1b; 20-oxo | 71 ± 18 | 0.57 ± 0.06 |
| 5b; 24-oxo | 329 ± 35 | 0.95 ± 0.08 |
| 4b; 23-oxo | 899 ± 150 | 0.89 ± 0.11 |
| 2b; 20-oxo | 1,780 ± 180 | 1.36 ± 0.16 |
| 3b; 22-oxo | 3,230 ± 640 | 0.73 ± 0.11 |
| 35b; Δ$^{22}$-24-one | 105 ± 12 | 0.90 ± 0.07 |

TABLE 1-continued

Displacement of [$^{35}$S]-TBPS binding by Cyclosteroids.

| Compound | IC$_{50}$ (nM)[a] | nHill |
|---|---|---|
| 22c; Δ$^{20(22)}$-23-one | 268 ± 43 | 0.64 ± 0.05 |
| 11b; Δ$^{22}$-20-one | 1,570 ± 140 | 1.15 ± 0.10 |
| 30b; Δ$^{23}$-22-one | 4750 ± 970 | 0.95 ± 0.18 |
| 13b; Δ$^{20(22)}$-ene | 484 ± 103 | 0.81 ± 0.11 |
| 52; 20-[exo-CH$_2$] | 213 ± 21 | 0.92 ± 0.07 |

[a]Results presented are from duplicate experiments performed in triplicate. Error limits are calculated as standard error of the means.

EXAMPLE 27

*Xenopus Oocyte* Electrophysiological Methods

Stage V-VI oocytes were harvested from sexually mature female *Xenopus laevis* (*Xenopus* One, Northland, Mich.) under 0.1% tricaine (3-aminobenzoic acid ethyl ester) anesthesia. Oocytes were defolliculated by shaking for 20 min at 37° C. in collagenase (2 mg/ml) dissolved in calcium-free solution containing (in mM): 96 NaCl, 2 KCl, 1 MgCl$_2$, and 5 HEPES at pH 7.4. Capped mRNA, encoding rat GABA$_A$ receptor α1, β2 and γ2L subunits was transcribed in vitro using the mMESSAGE mMachine Kit (Ambion, Austin, Tex.) from linearized pBluescript vectors containing receptor coding regions. Subunit transcripts were injected in equal parts (20-40 ng total RNA) 8-24 hours following defolliculation. Oocytes were incubated up to 5 days at 18° C. in ND96 medium containing (in mM): 96 NaCl, 1 KCl, 1 MgCl$_2$, 2 CaCl$_2$ and 5 HEPES at pH 7.4, supplemented with pyruvate (5 mM), penicillin (100 U/ml), streptomycin (100 μg/ml) and gentamycin (50 μg/ml). The cDNAs for the rat GABA$_A$-receptor subunits were originally provided by A. Tobin, University of California, Los Angels (α1), P. Malherbe, Hoffman-La Roche, Switzerland (β2), C. Fraser, National Institute on Alcohol Abuse and Alcoholism (γ2L).

Two-electrode voltage-clamp experiments were performed with a Warner OC725 amplifier 2-5 days following RNA injection. The extracellular recording solution was ND96 medium with no supplements. Intracellular recording pipettes were filled with 3 M KCl and had open tip resistances of ~1 MΩ. Drugs were applied from a common tip via a gravity-driven multibarrel drug-delivery system. Steroids were simultaneously co-applied with GABA. Cells were clamped at −70 mV for all experiments, and peak current during 20 s drug applications was measured. Data acquisition and analysis were performed with pCLAMP software (Axon Instruments, California). Statistical differences were determined using a two-tailed Student's t-test.

TABLE 2

Modulation of rat α1β2γ2 GABA$_A$ Receptor Function by Cyclosteroids.

| | Oocyte Electrophysiology[a] | | | |
|---|---|---|---|---|
| Compound | 0.1 μM | 1 μM | 10 μM | Gating (10 μM) |
| 5α-Steroids | | | | |
| 1a; 20-oxo[b] | 1.26 ± 0.14 | 3.89 ± 1.34 | 9.65 ± 3.87 | 0.37 ± 0.07 |
| 5a; 24-oxo | 1.22 ± 0.23 | 3.05 ± 0.79 | 10.73 ± 1.87 | 0.39 ± 0.69 |
| 4a; 23-oxo | 1.39 ± 0.38 | 1.64 ± 0.15 | 6.49 ± 0.59 | 0.32 ± 0.01 |
| 2a; 20-oxo | 1.01 ± 0.03 | 1.44 ± 0.03 | 2.28 0.05 | 0 ± 0.1 |
| 3a; 22-oxo | 1.30 ± 0.15 | 1.61 ± 0.22 | 2.93 ± 0.68 | 0.06 ± 0.06 |
| 35a; Δ$^{22}$-24-one | 1.98 ± 0.25 | 8.33 ± 0.75 | 9.45 ± 4.19 | 0.07 ± 0.10 |

TABLE 2-continued

Modulation of rat α1β2γ2 GABA$_A$ Receptor Function by Cyclosteroids.

| Compound | Oocyte Electrophysiology[a] | | | |
|---|---|---|---|---|
| | 0.1 µM | 1 µM | 10 µM | Gating (10 µM) |
| 21c; Δ$^{20(22)}$-23-one | 1.59 ± 0.14 | 5.53 ± 0.66 | 16.58 ± 2.45 | 0.35 ± 0.12 |
| 11a; Δ$^{22}$-20-one | 1.49 ± 0.20 | 5.87 ± 1.52 | 9.07 ± 1.86 | 0.72 ± 0.03 |
| 30a; Δ$^{23}$-22-one | 1.12 ± 0.08 | 1.54 ± 0.30 | 5.07 ± 0.98 | −0.04 ± 0.05 |
| 19a; (22S,23S)-epoxy-20-one | 1.47 ± 0.17 | 1.92 ± 0.23 | 8.90 ± 2.10 | 0.23 ± 0.24 |
| 19b; (22R,23R)-epoxy-20-one | 1.13 ± 0.02 | 2.11 ± 0.26 | 5.47 ± 0.62 | 0.21 ± 0.02 |
| 39; 20-N (eq) | 1.04 ± 0.03 | 1.12 ± 0.08 | 1.70 ± 0.10 | 0.04 ± 0.04 |
| 40; 20-CN (ax) | 1.06 ± 0.03 | 1.23 ± 0.02 | 1.27 ± 0.02 | −0.01 ± 0.01 |
| 44; 22-CN (eq) | 1.19 ± 0.02 | 1.14 ± 0.13 | 4.01 ± 0.42 | 0.03 ± 0.01 |
| 45; 22-CN (ax) | 0.90 ± 0.02 | 0.82 ± 0.02 | 0.87 ± 0.01 | −0.01 ± 0 |
| 49; 23-CN (ax) | — | — | 1.3 ± 0.1 | — |
| 50; 23-CN (eq) | — | — | 2.1 ± 0.2 | — |
| 13a; Δ$^{20(22)}$-ene | 1.53 ± 0.45 | 2.12 ± 0.40 | 2.68 ± 0.42 | −0.32 ± 0.15 |
| 51; 20-[exo-CH$_2$] | 0.90 ± 0.15 | 0.93 ± 0.08 | 0.95 ± 0.05 | −0.06 ± 0.06 |
| 53; 22-[exo-CH$_2$] | — | — | 1.05 ± 0.04 | — |
| 57; Δ$^{20(22)}$-20-CN | 0.91 ± 0.03 | 0.96 ± 0.04 | 3.18 ± 0.24 | 0.01 ± 0.02 |
| 60; Δ$^{20(22),23}$-diene | — | — | 1.1 ± 0.1 | — |
| 61; Δ$^{23}$-ene* | 1.28 ± 0.08 | 1.47 ± 0.10 | 1.72 ± 0.26 | 0.19 ± 0.10 |
| 63; exo-[CHCN] | 6.29 ± 1.71 | 12.34 ± 3.28 | 17.82 ± 3.75 | 0.01 ± 0.02 |
| 64; exo-[CHCN] | 1.19 ± 0.04 | 1.27 ± 0.03 | 1.74 ± 0.11 | 0.03 ± 0.04 |
| 67; 20-OH (ax) | 0.89 ± 0.03 | 0.94 ± 0.08 | 1.37 ± 0.15 | −0.01 ± 0.00 |
| 68; 20-OH (eq) | 0.74 ± 0.05 | 0.74 ± 0.05 | 0.79 ± 0.04 | 0.01 ± 0.02 |
| 69; 20-OMe (ax) | 0.90 ± 0.04 | 1.26 ± 0.09 | 1.72 ± 0.28 | 0.00 ± 0.00 |
| 70; 20-OMe (eq) | 0.74 ± 0.01 | 0.87 ± 0.02 | 1.02 ± 0.03 | 0.00 ± 0.00 |
| 71; (20R,22S)-epoxide | 0.90 ± 0.05 | 1.05 ± 0.09 | 1.94 ± 0.23 | 0.00 ± 0.00 |
| 72; (20S,22R)-epoxide | 0.90 ± 0.15 | 2.20 ± 0.25 | 6.39 ± 1.33 | −0.01 ± 0.04 |
| 73; exo-(20S)-epoxide | 0.88 ± 0.05 | 2.54 ± 0.40 | 4.84 ± 1.05 | −0.02 ± 0.04 |
| 74; exo-(20R)-epoxide | 1.61 ± 0.18 | 5.46 ± 1.21 | 4.53 ± 0.75 | −0.01 ± 0.01 |
| 79; 20-(acetyl) (ax) | 1.00 ± 0.08 | 1.13 ± 0.15 | 1.70 ± 0.12 | −0.06 ± 0.04 |
| 80; 20-(acetyl) (eq) | 0.85 ± 0.02 | 0.77 ± 0.03 | 0.93 ± 0.07 | 0.01 ± 0.01 |
| 83; Δ$^{20(22)}$-20(acetyl) | 0.89 ± 0.02 | 0.86 ± 0.04 | 1.15 ± 0.04 | 0.00 ± 0.00 |
| 89; 20-one | 0.81 ± 0.02 | 1.02 ± 0.07 | 4.54 ± 0.64 | 0.01 ± 0.00 |
| 94; Δ$^{18(21)}$-20-one | 0.96 ± 0.02 | 1.41 ± 0.09 | 2.78 ± 0.13 | −0.04 ± 0.02 |
| 95; Δ$^{18(21)}$-20-one, 21-Br | 1.25 ± 0.08 | 1.99 ± 0.20 | 8.75 ± 1.92 | 0.02 ± 0.02 |
| 96; exo-[CHCN] | 1.40 ± 0.21 | 2.33 ± 0.30 | 2.90 ± 0.29 | 0.03 ± 0.03 |
| 97; exo-[CHCN] | 0.88 ± 0.07 | 0.87 ± 0.15 | 1.10 ± 0.08 | −0.02 ± 0.06 |
| 5β-Steroids | | | | |
| 1b; 20-oxo | 1.20 ± 0.10 | 2.82 ± 0.51 | 9.77 ± 2.15 | 0.61 ± 0.03 |
| 5b; 24-oxo | 1.26 ± 0.05 | 3.45 ± 0.29 | 10.42 ± 1.65 | 0.04 ± 0.02 |
| 4b; 23-oxo | 0.97 ± 0.03 | 1.03 ± 0.08 | 3.17 ± 0.42 | 0.01 ± 0.01 |
| 2b; 20-oxo | 0.93 ± 0.06 | 1.12 ± 0.14 | 1.51 ± 0.13 | −0.25 ± 0.21 |
| 3b; 22-oxo | 0.97 ± 0.01 | 1.11 ± 0.14 | 2.65 ± 0.33 | −0.10 ± 0.06 |
| 35b; Δ22-24-one | 1.36 ± 0.60 | 3.15 ± 1.19 | 21.38 ± 11.08 | 0.20 ± 0.19 |
| 22c; Δ20(22)-23-one | 1.07 ± 0.10 | 1.83 ± 0.25 | 4.50 ± 0.46 | −0.02 ± 0.01 |
| 11b; Δ22-20-one | 1.07 ± 0.17 | 1.17 ± 0.11 | 2.34 ± 0.37 | 0.11 ± 0.04 |
| 30b; Δ23-22-one | 1.87 ± 0.24 | 1.80 ± 0.25 | 4.44 ± 0.87 | 0.26 ± 0.31 |
| 1b; 20-oxo | 1.20 ± 0.10 | 2.82 ± 0.51 | 9.77 ± 2.15 | 0.06 ± 0.03 |
| 13b; Δ$^{20(22)}$-ene | 1.44 ± 0.17 | 2.09 ± 0.35 | 3.48 ± 1.01 | −0.05 ± 0.09 |
| 52; 20-[exo-CH$_2$] | 1.57 ± 0.16 | 3.47 ± 0.50 | 6.22 ± 0.92 | −0.02 ± 0.02 |

The GABA concentration used for the control response was 2 µM. Each compound was evaluated on at least four different oocytes at the concentrations indicated, and the results reported are the ratio of the currents measured in the presence/absence of added compound. (G) represents direct current gated by 10 µM compound in the absence of GABA, and this current is reported as the ratio of compound only current/2 µM GABA current. Error limits are calculated as standard error of the means.

Values reported are from Convey, D., et al., *Neurosteroid Analogues. 8. Structure-Activity Studies of N-Acylated 17a-Aza-D-homosteroid Analogues of the Anesthetic Steroids* (3α,5α)-*and* (3α,5β)-3-*Hydroxypregnan*-20-*one*, J. Med. Chem., 2000, 43, 3201-3204.

Generally, FIG. 1 depicts the potentiation of electrophysiological responses to GABA by cyclosteroids using two current traces (chloride currents) (FIGS. 1A and 1B) and two tables (FIGS. 1C and 1D). In particular, FIG. 1A is a current trace (chloride current) depicting GABA currents potentiated by 5α-reduced cyclosteroids. The current trace depcits a two-electrode voltage-clamp recording (−70 mV) from an oocyte showing the response to 2 µM GABA alone and in the presence of 500 nM test compound 35a and in the presence of reference compound 1a. At this concentration, effects of the steroids were readily reversible as shown by the GABA recovery panel. FIG. 1B depicts an analogous experiment in another oocyte showing effects of 5,β-reduced compounds, 35b and 1b. FIG. 1C depicts a table of chloride current versus specific compounds, which summarizes the effects of certain cyclosteroids tested at 500 nM against the response to 2 μM GABA alone (dotted line denotes the normalized response to GABA alone). FIG. 1D depicts a similar summary table for the 5β-reduced series.

EXAMPLE 28

Tadpole Behavioral Methods

Tadpole LRR was measured as described previously. (See, Wittmer, L. L., et al., *Enantioselectivity of steroid-induced γ-aminobutyric acidA receptor modulation and anesthesia*, Mol. Phar., 1996, 50:1581-1586). Briefly, groups of 10 early prelimb-bud stage *Xenopus laevis* tadpoles (Nasco, Fort Atkinson, Wis.) were placed in 100 mL of oxygenated Ringer's stock solution containing various concentrations of compound. Compounds were added from a 10 mM DMSO stock (final concentration of DMSO in test solutions ≦0.1%). After equilibrating at room temperature for 3 h, tadpoles were evaluated using the LRR and LSR behavioral endpoints. LRR was defined as failure of the tadpole to right itself within 5 sec after being flipped by a smooth glass rod. LSR was defined as failure of the tadpole to swim when touched by a smooth glass rod. In general, the tadpoles regained their righting and swimming reflexes when placed in fresh oxygenated Ringer's solution. Control beakers containing up to 0.6% DMSO produced no LRR or LSR in tadpoles.

Tadpole LRR and LSR concentration-response curves were fit using Sigma Plot version 3.0 to the Hill equation $$f = R_{max}/\{1 + ([conc]/EC_{50})^n\}$$

where $R_{max}$ is the maximum effect, [conc] is the steroid concentration, $EC_{50}$ is the half-maximal effective concentration, and n is the Hill coefficient.

TABLE 3

Cyclosteroid effects on tadpole righting and swimming reflexes.

| Compounds | LRRa ED$_{50}$ (μM) | LRR NHill | LSR[b] EC$_{50}$ (μM) | LSR nHill |
|---|---|---|---|---|
| | 5α-Steriods | | | |
| 1a; 20-one | 0.42 ± 0.04 | −1.83 ± 0.32 | 5.50 ± 0.48 | −7.5 ± 1.1 |
| 5a; 24-one | 0.32 ± 0.02 | −1.75 ± 0.17 | 1.73 ± 0.03 | −36.5 ± 0.07 |
| 4a; 23-one | 1.12 ± 0.36 | −1.75 ± 0.83 | 3.58 ± 1.08 | −16.7 ± 28.3 |
| 2a; 20-one | 1.36 ± 0.20 | −2.51 ± 0.76 | 5.45 ± 0.07 | −33.5 ± 0.1 |
| 3a; 22-one | 2.37 ± 0.47 | −2.02 ± 0.64 | None @ 10 | — |
| 35a; $\Delta^{23}$-24-one | 1.02 ± 0.0 | −17.1 ± 0.91 | 2.66 ± 0.0 | −24.2 ± 0.0 |
| 21c; $\Delta^{20(22)}$-23-one | 1.28 ± 0.38 | −1.16 ± 0.26 | 10.0 ± 0.0 | −17.0 ± 0.0 |
| 11a; $\Delta^{22}$-20-one | 3.38 ± 0.67 | −2.79 ± 1.89 | None @ 10 | — |
| 30a; $\Delta^{23}$-22-one | 0.73 ± 0.16 | −1.57 ± 0.43 | 5.48 ± 0.09 | −33.5 ± 0.1 |
| 19a; (22S,23S)-epoxy-20-one | 1.75 ± 0.46 | −1.60 ± 0.49 | 10.0 ± 0.0 | −17.0 ± 0.04 |
| 19b; (22R,23R)-epoxy-20-one | 0.96 ± 0.29 | −1.14 ± 0.27 | 10.0 ± 0.0 | −17.0 |
| 31a; (23R,24R)-epoxide** | — | — | — | — |
| 39; 20-CN (eq) | 0.49 ± 0.09 | −1.21 ± 0.22 | None @ 10 | — |
| 40; 20-CN (ax) | >10 | — | None @ 10 | — |
| 44; 22-CN (eq) | 0.30 ± 0.03 | −1.81 ± 0.31 | 6.28 ± 1.08 | −2.98 ± 0.47 |
| 45; 22-CN (ax) | >10 | — | None @ 10 | — |
| 49; 23-CN (ax) | 0.35 ± 0.09 | −1.49 ± 0.49 | >10 | — |
| 50; 23-CN (eq) | 0.35 ± 0.07 | −2.11 ± 0.84 | 0.95 ± 0.01 | −15.7 ± 0.43 |
| 13a; $\Delta^{20(22)}$-ene | >10 | — | None @ 10 | — |
| 51; 20-[exo-CH$_2$] | >10 | — | None @ 10 | — |
| 53; 22-[exo-CH$_2$] | — | — | — | — |
| 57; $\Delta^{20(22)}$-20-CN | 0.42 | ±0.10 | None @ 10 | — |
| 60; $\Delta^{20(22),23}$-diene | 2.70 ± 0.72 | −1.63 ± 0.49 | >10 | — |
| 61; $\Delta^{23}$-ene* | None @ 10 | — | None @ 10 | — |
| 63; exo-[CHCN] | 0.04 ± 0.00 | −3.5 ± 0.54 | 0.08 ± 0.02 | −2.33 ± 1.12 |
| 64; exo-[CHCN] | 0.68 ± 0.15 | −1.68 ± 0.48 | 10.2 ± 0.00 | −11.4 ± 0.02 |
| 67; 20-OH (ax) | None @ 10 | — | None @ 10 | — |
| 68; 20-OH (eq) | >10 | — | None @ 10 | — |
| 69; 20-OMe (ax) | None @ 10 | — | None @ 10 | — |
| 70; 20-OMe (eq) | >10 | — | None @ 10 | — |
| 71; (20R,22S)-epoxide | None @ 10 | — | None @ 10 | — |
| 72; (20S,22R)-epoxide | 19.3 ± 30.8 | −1.01 ± 0.52 | None @ 10 | — |
| 73; exo-(20S)-epoxide | 4.00 ± 1.08 | −1.44 ± 0.28 | None @ 10 | — |
| 74; exo-(20R)-epoxide | >10 | — | None @ 10 | — |
| 79; 20-(acetyl) (ax) | None @ 10 | — | None @ 10 | — |
| 80; 20-(acetyl) (eq) | None @ 10 | — | None @ 10 | — |
| 83; $\Delta^{20(22)}$-20-(acetyl) | 7.20 ± 6.62 | −1.21 ± 0.41 | None @ 10 | — |
| 89; 20-one | 2.63 ± 0.07 | −3.16 ± 0.35 | 5.48 ± 0.15 | −33.4 ± 0.13 |
| 94; $\Delta^{18(21)}$-20-one | 3.37 ± 0.16 | −14.8 ± 6.18 | 9.52 ± 0.00 | −18.8 ± 0.00 |
| 95; $\Delta^{18(21)}$-20-one, 21-Br | 0.29 ± 0.04 | −1.89 ± 0.51 | 0.55 ± 0.09 | −33.5 ± 0.06 |
| 96; exo-[CHCN] | 2.77 ± 1.16 | −0.98 ± 0.19 | None @ 10 | — |
| 97; exo-[CHCN] | >10 | — | None @ 10 | — |

TABLE 3-continued

Cyclosteroid effects on tadpole righting and swimming reflexes.

| Compounds | LRRa ED$_{50}$ (μM) | LRR NHill | LSR[b] EC$_{50}$ (μM) | LSR nHill |
|---|---|---|---|---|
| 5β-Steriods | | | | |
| 1b; 20-one | 0.063 ± 0.003 | −1.54 ± 0.12 | 0.30 ± 0.0 | −6.93 ± 0.47 |
| 5b; 24-one | 0.40 ± 0.12 | −4.97 ± 5.29 | 0.89 ± 0.0 | −18.2 ± 0.4 |
| 4b; 23-one | 1.44 ± 0.02 | −3.02 ± 0.09 | 3.55 ± 1.15 | −17.5 ± 33.6 |
| 2b; 20-one | 0.94 ± 0.55 | −1.23 ± 0.64 | 5.48 ± 0.08 | −33.5 ± 0.1 |
| 3b; 22-one | 2.47 ± 0.53 | −1.86 ± 0.57 | 9.43 ± 0.06 | −18.7 ± 0.6 |
| 35b; $\Delta^{23}$-24-one | 0.40 ± 0.13 | −4.97 ± 5.75 | 1.00 ± 0.0 | −18.6 ± 0.1 |
| 22c; $\Delta^{20(22)}$-23-one | 1.05 ± 0.00 | −16.6 ± 0.9 | 2.72 ± 0.01 | −22.1 ± 0.7 |
| 11b; $\Delta^{22}$-20-one | 2.56 ± 1.39 | −1.59 ± 0.95 | 8.95 ± 0.01 | −19.8 ± 0.01 |
| 30b; $\Delta^{23}$-22-one | 0.56 ± 0.9 | −1.50 ± 0.27 | 5.48 | −33.5 ± 0.1 |
| 13b; $\Delta^{20(22)}$-ene | 1.28 ± 1.80 | −0.64 ± 0.36 | >10 | — |
| 52; 20-[exo-CH$_2$] | 4.88 ± 1.12 | −1.80 ± 0.55 | >10 | — |

[a]LRR = Loss of righting response. Error limits are calculated as standard error of the means.
[b]LSR = Loss of swimming response. Error limits are calculated as standard error of the means.

EXAMPLE 29

Elemental Analysis

| | | | | | |
|---|---|---|---|---|---|
| 2a | Anal. For C$_{22}$H$_{34}$O$_2$ | Calcd. | C, 79.95 | H, 10.37 | |
| | | Found | C, 79.79 | H, 10.50 | |
| 3a | Anal. For C$_{22}$H$_{34}$O$_2$ | Calcd. | C, 79.95 | H, 10.37 | |
| | | Found | C, 80.00 | H, 10.32 | |
| 4a | Anal. For C$_{22}$H$_{34}$O$_2$ | Calcd. | C, 79.95 | H, 10.37 | |
| | | Found | C, 80.13 | H, 10.16 | |
| 5a | Anal. For C$_{22}$H$_{34}$O$_2$ | Calcd. | C, 79.95 | H, 10.37 | |
| | | Found | C, 79.85 | H, 10.21 | |
| 7a | Anal. For C$_{24}$H$_{37}$NO$_3$ | Calcd. | C, 74.38 | H, 9.62 | N, 3.61 |
| | | Found | C, 74.50 | H, 9.50 | N, 3.50 |
| 8a | Anal. For C$_{24}$H$_{35}$NO$_3$ | Calcd. | C, 74.77 | H, 9.15 | N, 3.63 |
| | | Found | C, 74.67 | H, 9.37 | N, 3.44 |
| 9a | Anal. For C$_{26}$H$_{39}$NO$_4$ | Calcd. | C, 72.69 | H, 9.15 | N, 3.26 |
| | | Found | C, 72.47 | H, 8.97 | N, 3.13 |
| 11a | Anal. For C$_{22}$H$_{32}$O$_2$ | Calcd. | C, 80.44 | H, 9.82 | |
| | | Found | C, 80.21 | H, 9.89 | |
| 13a | Anal. For C$_{22}$H$_{34}$O | Calcd. | C, 84.02 | H, 10.90 | |
| | | Found | C, 84.19 | H, 10.92 | |
| 14a | Anal. For C$_{24}$H$_{38}$O$_2$ | Calcd. | C, 80.39 | H, 10.68 | |
| | | Found | C, 80.17 | H, 10.59 | |
| 19a | Anal. For C$_{22}$H$_{32}$O$_3$ | Calcd. | C, 76.70 | H, 9.36 | |
| | | Found | C, 76.57 | H, 9.50 | |
| 19b | Anal. For C$_{22}$H$_{32}$O$_3$ | Calcd. | C, 76.70 | H, 9.36 | |
| | | Found | C, 76.86 | H, 9.24 | |
| 21a | Anal. For C$_{22}$H$_{34}$O$_2$ | Calcd. | C, 79.95 | H, 10.37 | |
| | | Found | C, 80.05 | H, 10.27 | |
| 21c | Anal. For C$_{22}$H$_{32}$O$_2$ | Calcd. | C, 80.44 | H, 9.82 | |
| | | Found | C, 80.19 | H, 9.63 | |
| 23a | Anal. For C$_{26}$H$_{36}$O$_4$ | Calcd. | C, 75.69 | H, 8.80 | |
| | | Found | C, 75.42 | H, 8.69 | |
| 24a | Anal. For C$_{24}$H$_{36}$O$_3$ | Calcd. | C, 77.38 | H, 9.74 | |
| | | Found | C, 77.41 | H, 9.83 | |
| 24b | Anal. For C$_{24}$H$_{36}$O$_3$ | Calcd. | C, 77.38 | H, 9.74 | |
| | | Found | C, 77.18 | H, 9.57 | |
| 28a | Anal. For C$_{24}$H$_{36}$O$_2$ | Calcd. | C, 80.85 | H, 10.18 | |
| | | Found | C, 80.77 | H, 10.12 | |
| 30a | Anal. For C$_{22}$H$_{32}$O$_2$ | Calcd. | C, 80.44 | H, 9.82 | |
| | | Found | C, 80.32 | H, 9.83 | |
| 32a | Anal. For C$_{24}$H$_{37}$BrO$_3$ | Calcd. | C, 63.57 | H, 8.22 | |
| | | Found | C, 63.58 | H, 8.36 | |
| 33a | Anal. For C$_{24}$H$_{35}$BrO$_3$ | Calcd. | C, 63.85 | H, 7.81 | |
| | | Found | C, 63.66 | H, 8.00 | |
| 34a | Anal. For C$_{24}$H$_{34}$O$_3$ | Calcd. | C, 77.80 | H, 9.25 | |
| | | Found | C, 78.00 | H, 9.12 | |
| 35a | Anal. For C$_{22}$H$_{32}$O$_2$ | Calcd. | C, 80.44 | H, 9.82 | |
| | | Found | C, 80.63 | H, 9.70 | |
| 2b | Anal. For C$_{22}$H$_{34}$O$_2$ | Calcd. | C, 79.95 | H, 10.37 | |
| | | Found | C, 80.19 | H, 10.15 | |
| 3b | Anal. For C$_{22}$H$_{34}$O$_2$ | Calcd. | C, 79.95 | H, 10.37 | |
| | | Found | C, 79.90 | H, 10.23 | |
| 4b | Anal. For C$_{22}$H$_{34}$O$_2$ | Calcd. | C, 79.95 | H, 10.37 | |
| | | Found | C, 80.10 | H, 10.15 | |
| 5b | Anal. For C$_{22}$H$_{34}$O$_2$ | Calcd. | C, 79.95 | H, 10.37 | |
| | | Found | C, 80.10 | H, 10.43 | |
| 11b | Anal. For C$_{22}$H$_{32}$O$_2$ | Calcd. | C, 80.44 | H, 9.82 | |
| | | Found | C, 80.55 | H, 9.77 | |
| 22c | Anal. For C$_{22}$H$_{32}$O$_2$ | Calcd. | C, 80.44 | H, 9.82 | |
| | | Found | C, 80.58 | H, 9.87 | |
| 30b | Anal. For C$_{22}$H$_{32}$O$_2$ | Calcd. | C, 80.44 | H, 9.82 | |
| | | Found | C, 80.60 | H, 9.85 | |
| 35b | Anal. For C$_{22}$H$_{32}$O$_2$ | Calcd. | C, 80.44 | H, 9.82 | |
| | | Found | C, 80.56 | H, 9.94 | |
| 39 | Anal. For C$_{23}$H$_{35}$NO$_3$ | Calcd. | C, 80.88 | H, 10.33 | N, 4.10 |
| | | Found | C, 81.03 | H, 10.26 | N, 4.15 |
| 40 | Anal. For C$_{23}$H$_{35}$NO$_3$ | Calcd. | C, 80.88 | H, 10.33 | N, 4.10 |
| | | Found | C, 80.94 | H, 10.14 | N, 4.14 |
| 41 | Anal. For C$_{24}$H$_{36}$O$_3$ | Calcd. | C, 77.38 | H, 9.74 | |
| | | Found | C, 77.16 | H, 9.59 | |
| 44 | Anal. For C$_{23}$H$_{35}$NO | Calcd. | C, 80.88 | H, 10.33 | N, 4.10 |
| | | Found | C, 80.67 | H, 10.16 | N, 4.07 |
| 46 | Anal. For C$_{24}$H$_{36}$O$_3$ | Calcd. | C, 77.38 | H, 9.74 | |
| | | Found | C, 77.44 | H, 9.52 | |
| 49 | Anal. For C$_{23}$H$_{35}$NO | Calcd. | C, 80.88 | H, 10.33 | N, 4.10 |
| | | Found | C, 80.65 | H, 10.33 | N, 4.07 |
| 50 | Anal. For C$_{23}$H$_{35}$NO | Calcd. | C, 80.88 | H, 10.33 | N, 4.10 |
| | | Found | C, 80.60 | H, 10.33 | N, 3.80 |
| 51 | Anal. For C$_{23}$H$_{36}$O | Calcd. | C, 84.09 | H, 11.04 | |
| | | Found | C, 84.19 | H, 11.00 | |
| 61 | Anal. For C$_{22}$H$_{34}$O | Calcd. | C, 84.02 | H, 10.90 | |
| | | Found | C, 84.20 | H, 10.84 | |
| 63 | Anal. For C$_{24}$H$_{35}$NO | Calcd. | C, 81.53 | H, 9.98 | N, 3.96 |
| | | Found | C, 81.70 | H, 9.91 | N, 3.95 |
| 64 | Anal. For C$_{24}$H$_{35}$NO | Calcd. | C, 81.53 | H, 9.98 | N, 3.96 |
| | | Found | C, 81.48 | H, 10.10 | N, 3.95 |
| 65 | Anal. For C$_{24}$H$_{40}$O$_3$ | Calcd. | C, 76.55 | H, 10.71 | |
| | | Found | C, 76.58 | H, 10.83 | |
| 66 | Anal. For C$_{24}$H$_{40}$O$_3$ | Calcd. | C, 76.55 | H, 10.71 | |
| | | Found | C, 76.38 | H, 10.67 | |
| 67 | Anal. For C$_{22}$H$_{36}$O$_2$ | Calcd. | C, 79.46 | H, 10.91 | |
| | | Found | C, 79.62 | H, 11.00 | |
| 68 | Anal. For C$_{22}$H$_{36}$O$_2$ | Calcd. | C, 79.46 | H, 10.91 | |
| | | Found | C, 79.60 | H, 10.96 | |
| 69 | Anal. For C$_{23}$H$_{38}$O$_2$ | Calcd. | C, 79.71 | H, 11.05 | |
| | | Found | C, 80.04 | H, 11.20 | |
| 70 | Anal. For C$_{23}$H$_{38}$O$_2$ | Calcd. | C, 79.71 | H, 11.05 | |
| | | Found | C, 79.80 | H, 10.89 | |

-continued

| | | | | | |
|---|---|---|---|---|---|
| 71 | Anal. For $C_{22}H_{34}O_2$ | Calcd. | C, 79.95 | H, 10.37 | |
| | | Found | C, 79.88 | H, 10.15 | |
| 72 | Anal. For $C_{22}H_{34}O_2$ | Calcd. | C, 79.95 | H, 10.37 | |
| | | Found | C, 80.16 | H, 10.18 | |
| 73 | Anal. For $C_{23}H_{36}O_2$ | Calcd. | C, 80.18 | H, 10.53 | |
| | | Found | C, 80.38 | H, 10.63 | |
| 74 | Anal. For $C_{23}H_{36}O_2$ | Calcd. | C, 80.18 | H, 10.53 | |
| | | Found | C, 79.96 | H, 10.67 | |
| 77 | Anal. For $C_{26}H_{42}O_3$ | Calcd. | C, 77.56 | H, 10.51 | |
| | | Found | C, 77.70 | H, 10.62 | |
| 78 | Anal. For $C_{26}H_{42}O_3$ | Calcd. | C, 77.56 | H, 10.51 | |
| | | Found | C, 77.76 | H, 10.70 | |
| 79 | Anal. For $C_{24}H_{38}O_2$ | Calcd. | C, 80.39 | H, 10.68 | |
| | | Found | C, 80.50 | H, 10.88 | |
| 80 | Anal. For $C_{24}H_{38}O_2$ | Calcd. | C, 80.39 | H, 10.68 | |
| | | Found | C, 80.25 | H, 10.47 | |
| 82 | Anal. For $C_{26}H_{40}O_3$ | Calcd. | C, 77.95 | H, 10.06 | |
| | | Found | C, 77.84 | H, 10.19 | |
| 83 | Anal. For $C_{24}H_{36}O_2$ | Calcd. | C, 80.85 | H, 10.18 | |
| | | Found | C, 81.02 | H, 10.37 | |
| 86 | Anal. For $C_{23}H_{34}O_3$ | Calcd. | C, 77.05 | H, 9.56 | |
| | | Found | C, 77.06 | H, 9.67 | |
| 88 | Anal. For $C_{28}H_{36}O_3$ | Calcd. | C, 79.96 | H, 8.63 | |
| | | Found | C, 79.98 | H, 8.80 | |
| 89 | Anal. For $C_{21}H_{32}O_2$ | Calcd. | C, 79.70 | H, 10.19 | |
| | | Found | C, 79.69 | H, 9.94 | |
| 94 | Anal. For $C_{21}H_{30}O_2$ | Calcd. | C, 80.21 | H, 9.62 | |
| | | Found | C, 80.16 | H, 9.66 | |
| 95 | Anal. For $C_{21}H_{29}BrO_2$ | Calcd. | C, 64.12 | H, 7.43 | |
| | | Found | C, 64.25 | H, 7.40 | |
| 96 | Anal. For $C_{23}H_{33}NO$ | Calcd. | C, 81.37 | H, 9.80 | N, 4.13 |
| | | Found | C, 81.16 | H, 9.67 | N, 3.95 |
| 97 | Anal. For $C_{23}H_{33}NO$ | Calcd. | C, 81.37 | H, 9.80 | N, 4.13 |
| | | Found | C, 81.51 | H, 10.00 | N, 4.16 |

What is claimed is:

1. A steroid or D-homosteroid of Formula (A)

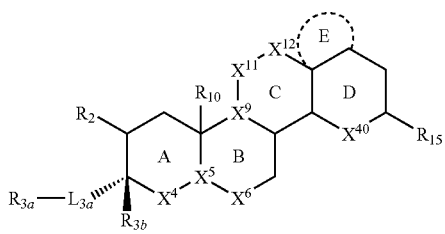

(A)

wherein $R_2$ is selected from the group consisting of hydrogen, alkoxy, and substituted or unsubstituted morpholine $R_{3a}$ is hydroxyl or carboxyl;

$R_{3b}$ is hydrogen, alkyl, alkenyl, or alkynyl optionally substituted with halo, hydroxyl, or substituted or unsubstituted aryl;

$R_5$ is α- or β-hydrogen;

$R_{10}$ is hydrogen or $C_{1-4}$ alkyl;

$R_{15}$ is hydrogen or oxo;

$R_6$, $R_{11}$ and $R_{12}$ are independently hydrogen or oxo;

$L_{3a}$ is selected from the group consisting of a bond, $C_{1-3}$ alkyl, heterosubstituted $C_{1-3}$ alkyl, or alkoxy;

$X_4$-$X_5$-$X_6$ is selected from the group consisting of

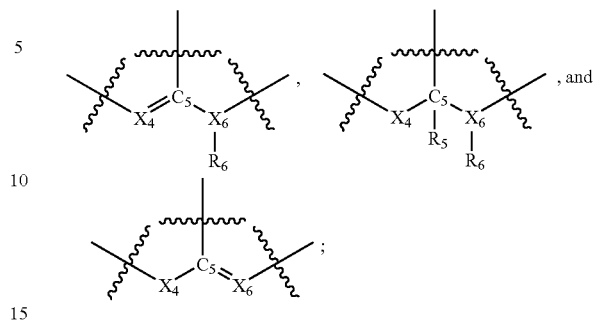

$X_9$-$X_{11}$-$X_{12}$ is selected from the group consisting of

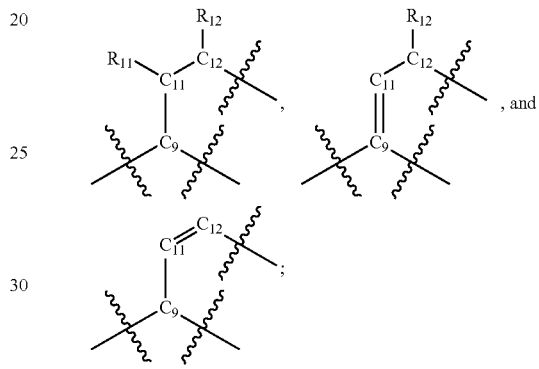

$X_{40}$ is a bond or a carbon atom; and

E is a 5- or 6-membered carbocyclic ring in the β-configuration in relation to the C and D rings, comprising a hydrogen bond acceptor and (i) the carbons at C(13) and C(17) when $X_{40}$ is a bond, or (ii) the carbons at C(13) and C(17a) when $X_{40}$ is carbon.

2. The steroid or D-homosteroid of claim 1 wherein the hydrogen bond acceptor is selected from the group consisting of keto, cyano, acyl, =$CHX_1$, —$OX_2$, —$C(O)X_2$, epoxide, an E ring alkene bond, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl.

3. The steroid or D-homosteroid of claim 2 wherein the E ring hydrogen bond acceptor is selected from the group consisting of keto, cyano, methylene, methoxy, acetyl, =CHCN, =$CHC(O)CH_3$, epoxide, an E ring alkene bond, and combinations thereof.

4. The steroid or D-homosteroid of claim 2 wherein $R_2$ is hydrogen or substituted or unsubstituted morpholine.

5. The steroid or D-homosteroid of claim 1 wherein the C(3) substituent is a carboxyl in the α-configuration or a sulfate.

6. The steroid or D-homosteroid of claim 2 wherein $L_{3a}$ is selected from the group consisting of a bond, methylene, ethylene, methoxy, and ethoxy and $R_{3a}$ is hydroxyl.

7. The steroid or D-homosteroid of claim 6 wherein $L_{3a}$ is a bond.

8. The steroid or D-homosteroid of claim 2 wherein $X_4$-$X_5$-$X_6$ is

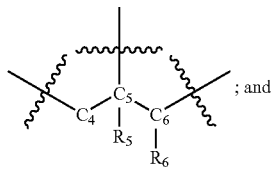 ; and $X_9$-$X_{11}$-$X_{12}$ is

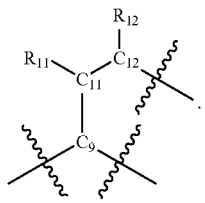.

9. The steroid or D-homosteroid of claim 2 wherein $X_{40}$ is a bond.

10. The steroid or D-homosteroid of claim 2 wherein $R_{3b}$ is ethynyl substituted with alkyl or optionally substituted aryl.

11. The steroid or D-homosteroid of claim 2 wherein $R_{3b}$ is ethynyl substituted with phenyl substituted with amino, dimethylamino, hydroxyl, carboxyl, or alkoxy.

12. The steroid or D-homosteroid of claim 2 wherein $R_{10}$ is hydrogen or β-methyl.

13. The steroid or D-homosteroid of claim 1 wherein $R_2$ is hydrogen;

$R_{3b}$ is hydrogen;

$R_{10}$ is hydrogen or β-methyl;

$R_{15}$ is hydrogen;

$R_6$, $R_{11}$ and $R_{12}$ are independently hydrogen or oxo;

$L_{3a}$ is a bond; and $X_{40}$ is a bond.

14. The steroid or D-homosteroid of claim 13 wherein the hydrogen bond acceptor is selected from the group consisting of keto, cyano, methylene, methoxy, acetyl, =CHCN, =CHC(O)CH$_3$, epoxide, an E ring alkene bond, and combinations thereof.

15. A steroid or D-homosteroid of Formula (A)

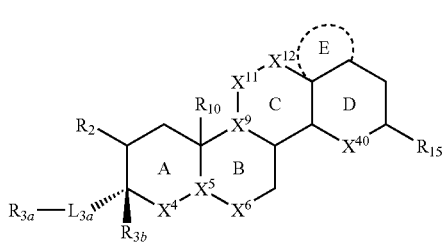

(A)

wherein $R_2$ is selected from the group consisting of hydrogen, alkoxy, and substituted or unsubstituted morpholine;

$R_{3a}$ is hydroxyl or carboxyl;

$R_{3b}$ is hydrogen, alkyl, alkenyl, or alkynyl optionally substituted with halo, hydroxyl, or substituted or unsubstituted aryl;

$R_5$ is α- or β-hydrogen;

$R_{10}$ is hydrogen or $C_{1-4}$ alkyl;

$R_{15}$ is hydrogen or oxo;

$R_6$ $R_{11}$ and $R_{12}$ are independently hydrogen or oxo;

$L_{3a}$ is selected from the group consisting of a bond, $C_{1-3}$ alkyl, heterosubstituted $C_{1-3}$ alkyl, or alkoxy;

$X_4$-$X_5$-$X_6$ is selected from the group consisting of

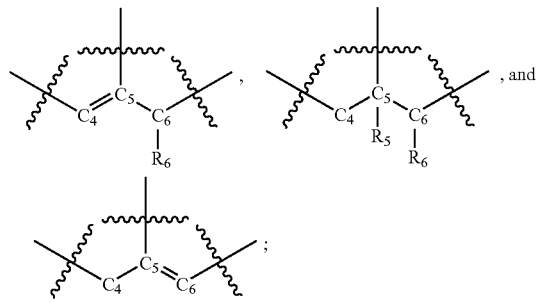

$X_9$-$X_{11}$-$X_{12}$ is selected from the group consisting of

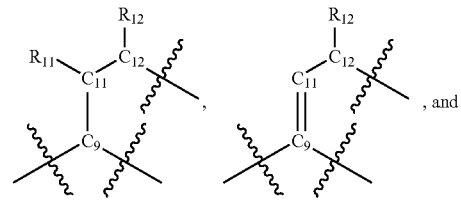

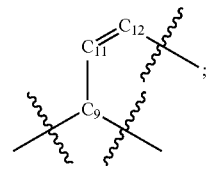;

$X_{40}$ is a bond or a carbon atom; and

E is a 5- or 6-membered carbocyclic ring in the β-configuration in relation to the C and D rings, comprising a hydrogen bond acceptor selected from the group consisting of keto, cyano, acyl, =CHX$_1$, —OX$_2$, —C(O)X$_2$, epoxide, an E ring alkene bond, and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl and (i) the carbons at C(13) and C(17) when X$_{40}$ is a bond, or (ii) the carbons at C(13) and C(17a) when X$_{40}$ is carbon.

16. The steroid or D-homosteroid of claim 1 having Formula (B)

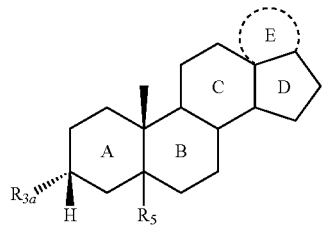

(B)

wherein $R_{3a}$ is hydroxyl or carboxyl; and $R_5$ is α- or β-hydrogen.

17. The steroid or D-homosteroid of claim 16 wherein the E ring comprises a hydrogen bond acceptor selected from the group consisting of keto, cyano, acyl, =CHX$_1$, —OX$_2$, —C(O)X$_2$, epoxide, an E ring alkene bond, and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl.

18. The steroid or D-homosteroid of claim 17 wherein the hydrogen bond acceptor is selected from the group consisting of keto, cyano, methylene, methoxy, acetyl, =CHCN, =CHC(O)CH$_3$, epoxide, and combinations thereof.

19. The steroid or D-homosteroid of claim 17 wherein the hydrogen bond acceptor comprises an E ring alkene bond.

20. The steroid or D-homosteroid of claim 16 having Formula (C)

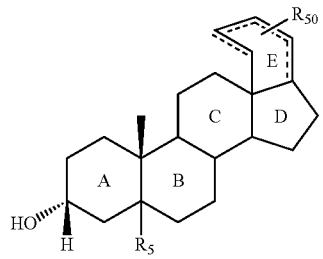

(C)

wherein $R_5$ is α- or β-hydrogen;

$R_{50}$ is selected from the group consisting of hydrogen, keto, cyano, acyl, =CHX$_1$, —OX$_2$, —C(O)X$_2$, epoxide, an E ring alkene bond, and combinations thereof; X$_1$ is selected from the group consisting of hydrogen, cyano, hydrocarbyl, substituted hydrocarbyl and acyl; and X$_2$ is selected from the group consisting of hydrogen, hydrocarbyl, substituted hydrocarbyl, and acyl, provided that when $R_{50}$ is hydrogen at least one pair of E ring atoms share a double bond; and E is a 6-membered carbocyclic ring wherein the dashed lines represent optional double bonds provided E comprises no more than 2 double bonds and provided each carbon ring atom of E is sp$^2$ or sp$^3$ hybridized.

21. The steroid or D-homosteroid of claim 20 wherein $R_{50}$ is selected from the group consisting of hydrogen, keto, cyano, methylene, methoxy, acetyl, =CHCN, =CHC(O)CH$_3$, epoxide, and combinations thereof, provided that when $R_{50}$ is hydrogen at least one pair of E ring atoms share a double bond.

22. A steroid or D-homosteroid selected from the group consisting of

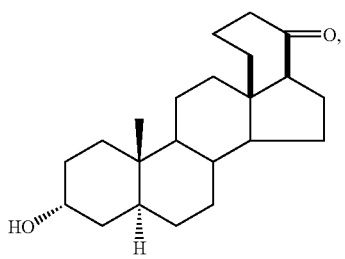

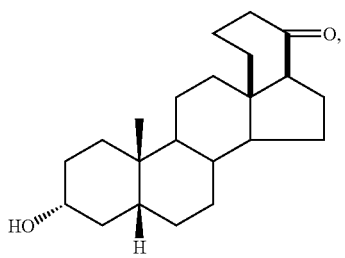

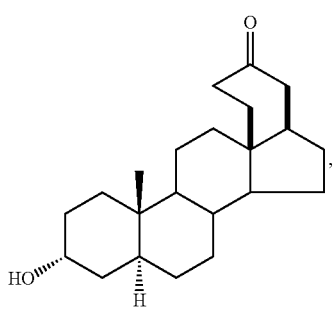

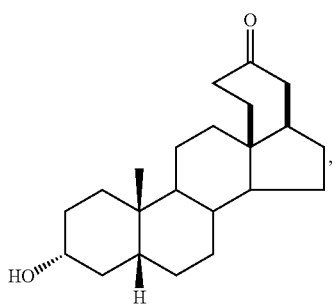

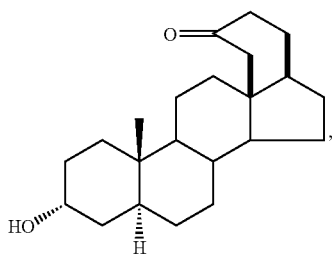

-continued
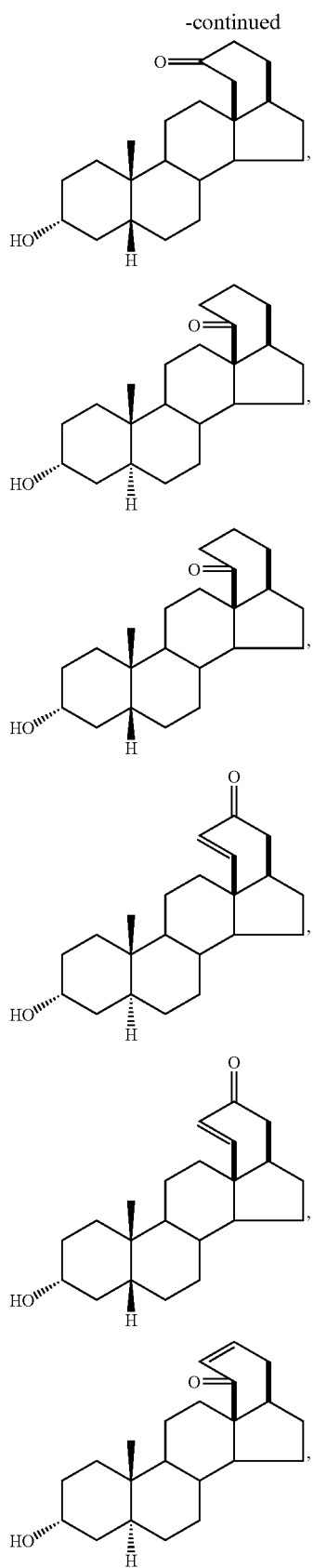
-continued
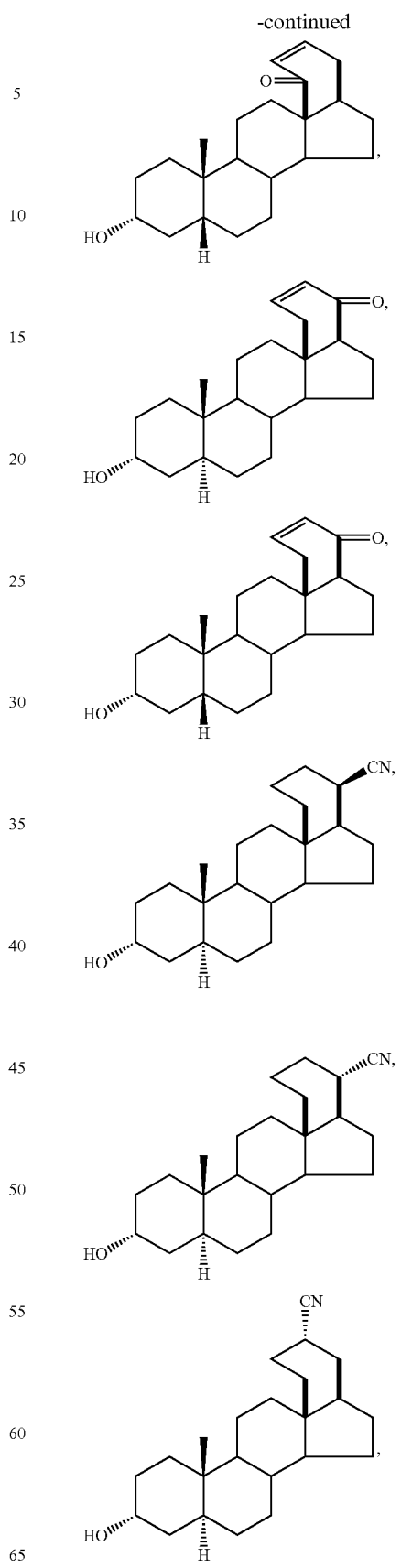

-continued
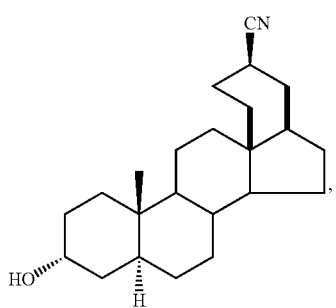
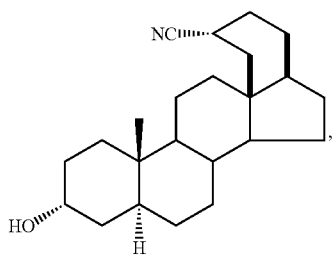
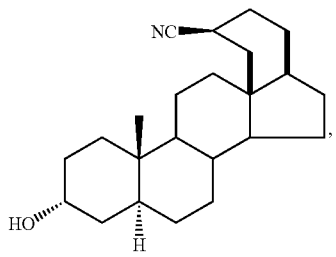
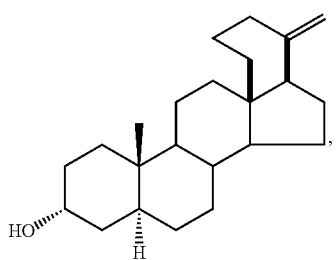
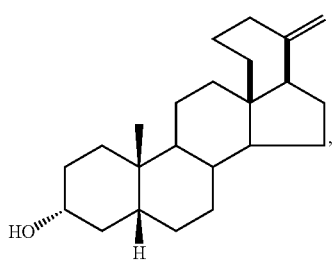
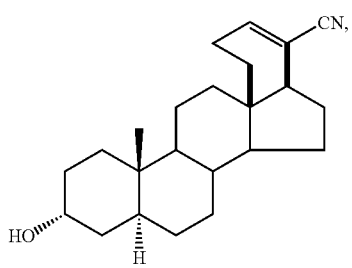
-continued
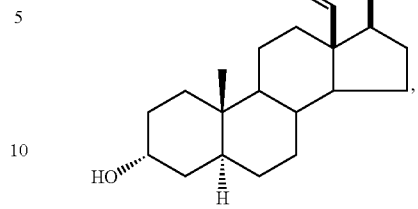
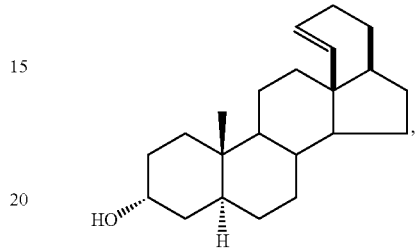
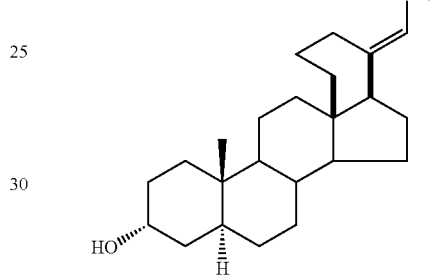
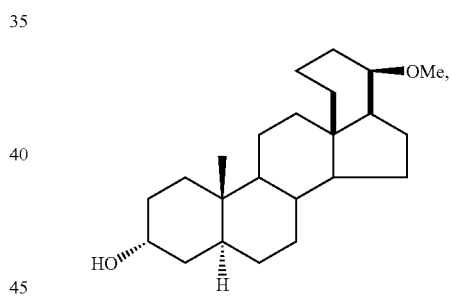
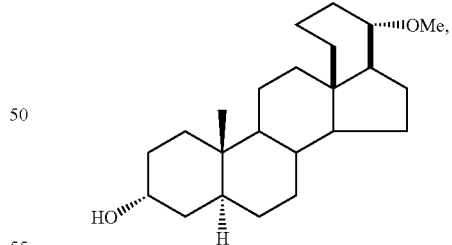
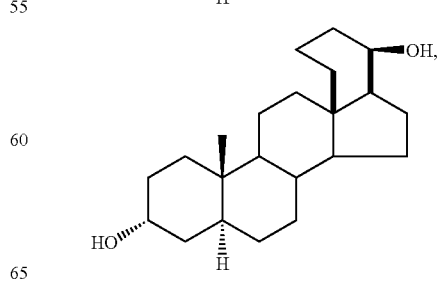

-continued
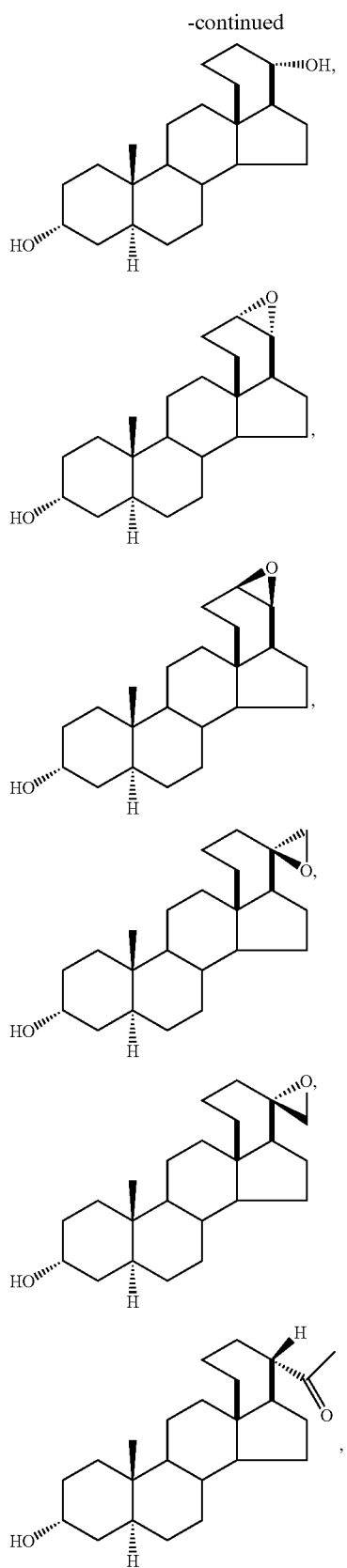
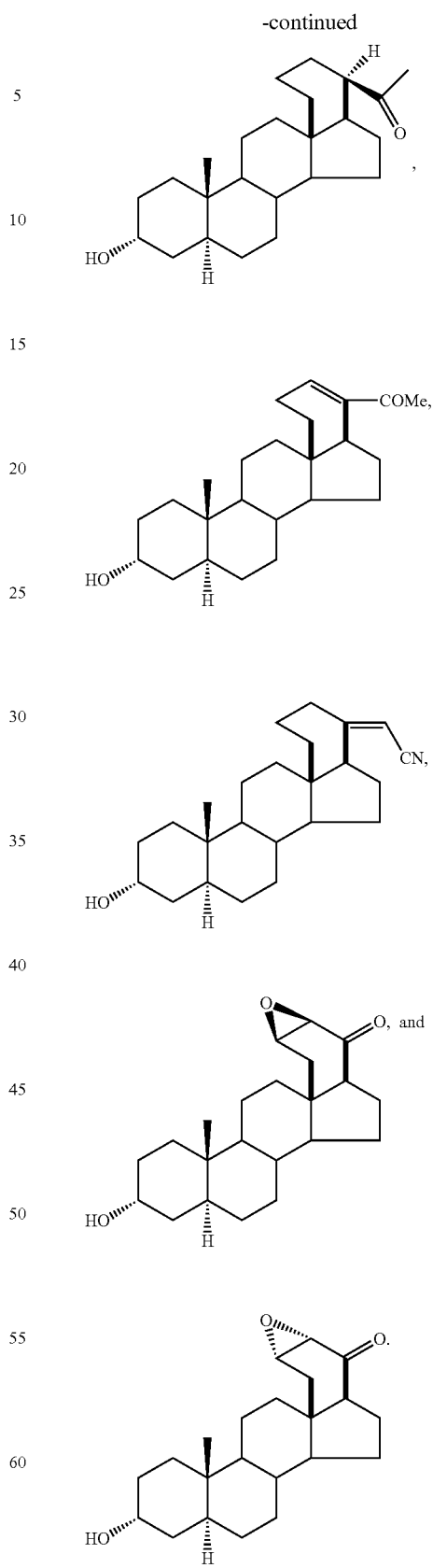

23. The steroid or D-homosteroid of claim 16 having Formula (D)

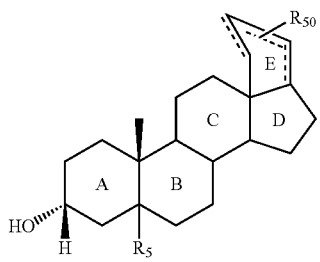

(D)

wherein

R₅ is α- or β-hydrogen;

R₅₀ is selected from the group consisting of hydrogen, keto, cyano, acyl, =CHX₁, —OX₂, —C(O)X₂, epoxide, an E ring alkene bond, and combinations thereof; X₁ is selected from the group consisting of hydrogen, cyano, hydrocarbyl, substituted hydrocarbyl and acyl; and X₂ is selected from the group consisting of hydrogen, hydrocarbyl, substituted hydrocarbyl, and acyl, provided that when R₅₀ is hydrogen at least one pair of E ring atoms share a double bond; and E is a 5-membered carbocyclic ring wherein the dashed lines represent optional double bonds provided E comprises no more than 2 double bonds and provided each carbon ring atom of E is sp² or sp³ hybridized.

24. The steroid or D-homosteroid of claim 23 wherein R₅₀ is selected from the group consisting of hydrogen, keto, cyano, methylene, methoxy, acetyl, =CHCN, =CHC(O)CH₃, epoxide, and combinations thereof, provided that when R₅₀ is hydrogen at least one pair of E ring atoms share a double bond.

25. The steroid or D-homosteroid of claim 23 wherein the steroid or D-homosteroid is selected from the group consisting of

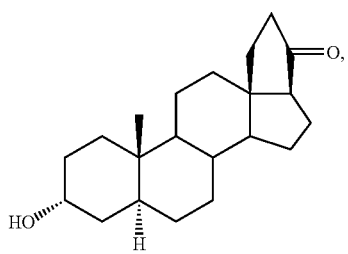

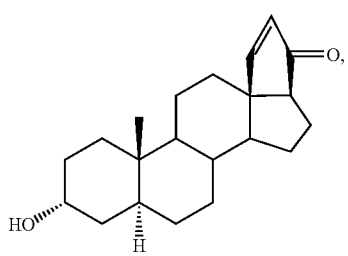

-continued

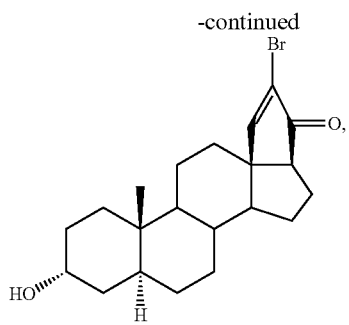

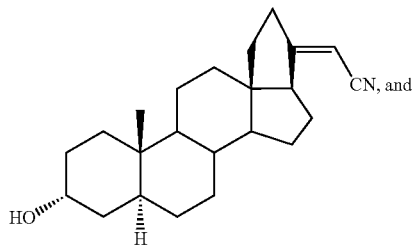

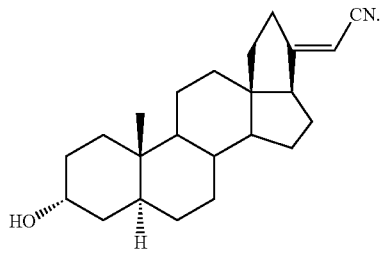

26. The steroid or D-homosteroid of claim 1 wherein the E ring is substituted by halo, alkyl, or combinations thereof.

27. A steroid or D-homosteroid of Formula (A)

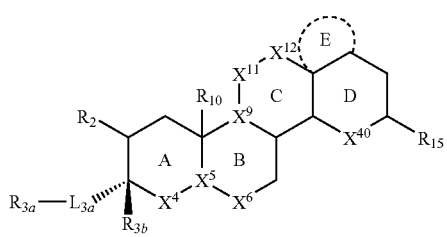

(A)

wherein

R₂ is selected from the group consisting of hydrogen, alkoxy, and substituted or unsubstituted morpholine R₃ₐ is selected from the group consisting of sulfate, phosphate, and phosphonate;

R₃ᵦ is hydrogen, alkyl, alkenyl, or alkynyl optionally substituted with halo, hydroxyl, or substituted or unsubstituted aryl;

R₅ is α- or β-hydrogen;

R₁₀ is hydrogen or C₁₋₄ alkyl;

R₁₅ is hydrogen or oxo;

R₆, R₁₁ and R₁₂ are independently hydrogen or oxo;

L₃ₐ is selected from the group consisting of a bond, C₁₋₃ alkyl, heterosubstituted C₁₋₃ alkyl, or alkoxy;

$X_4$-$X_5$-$X_6$ is selected from the group consisting of

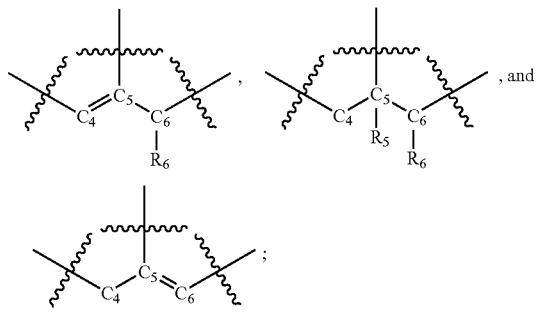

$X_9$-$X_{11}$-$X_{12}$ is selected from the group consisting of

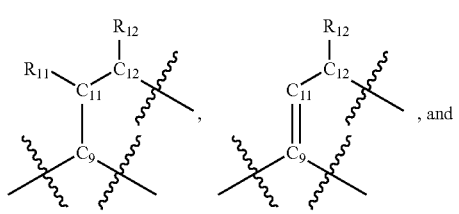

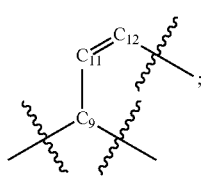

$X_{40}$ is a bond or a carbon atom; and

E is a 5- or 6-membered carbocyclic ring in the β-configuration in relation to the C and D rings, comprising a hydrogen bond acceptor and (i) the carbons at C(13) and C(17) when $X_{40}$ is a bond, or (ii) the carbons at C(13) and C(17a) when $X_{40}$ is carbon.

28. The steroid or D-homosteroid of claim 27 wherein $L_{3a}$ is a bond and $R_{3a}$ is in the β-configuration.

29. The steroid or D-homosteroid of claim 27 wherein the hydrogen bond acceptor is selected from the group consisting of keto, cyano, acyl, =CHX$_1$, —OX$_2$, —C(O)X$_2$, epoxide, an E ring alkene bond, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl.

30. A pharmaceutical composition comprising the steroid or D-homosteroid of claim 1 and at least one pharmaceutically acceptable carrier.

31. A pharmaceutical composition comprising a steroid or D-homosteroid and at least one pharmaceutically acceptable carrier wherein the steroid or D-homosteroid is selected from the group consisting of

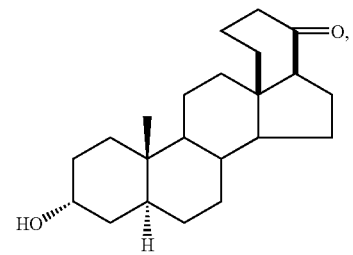

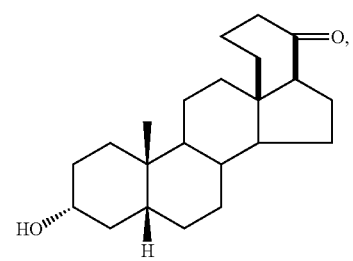

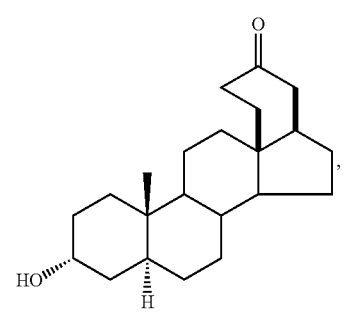

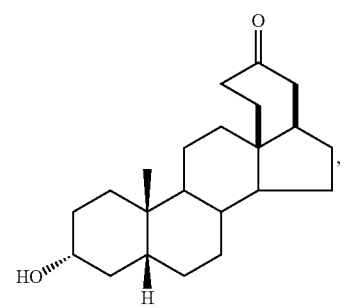

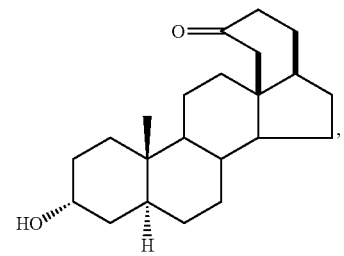

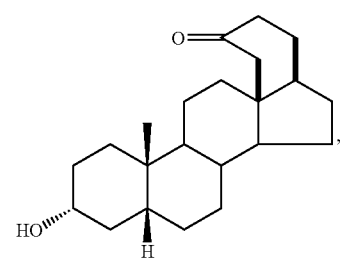

105
-continued
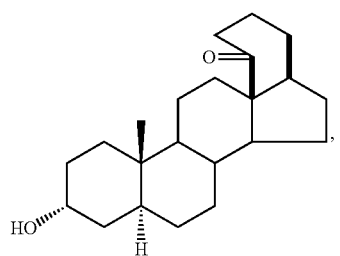
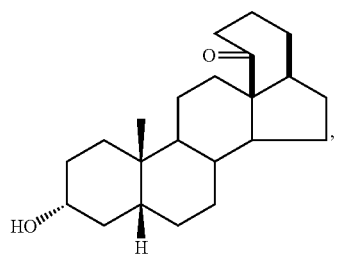
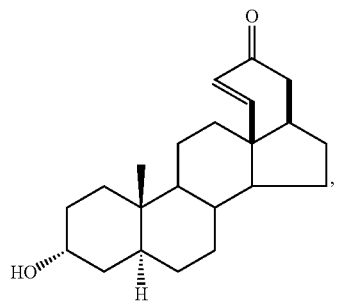
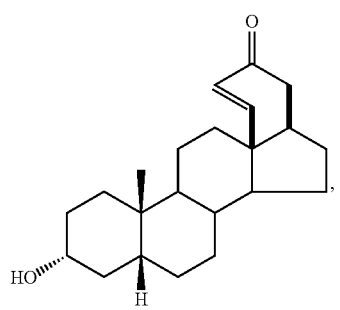
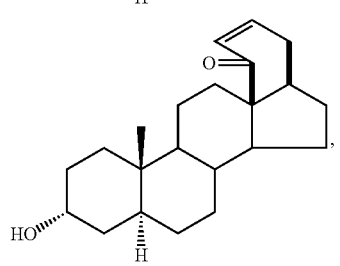
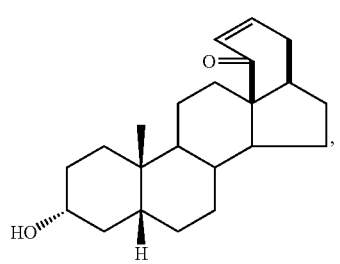
106
-continued
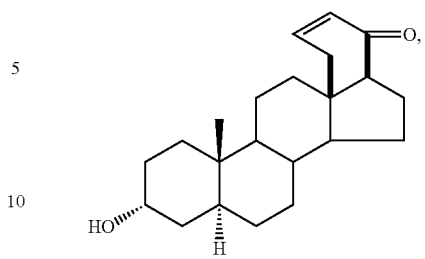
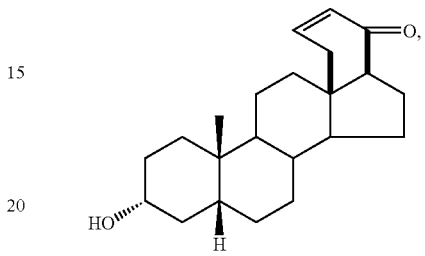
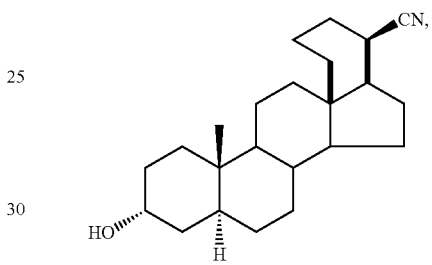
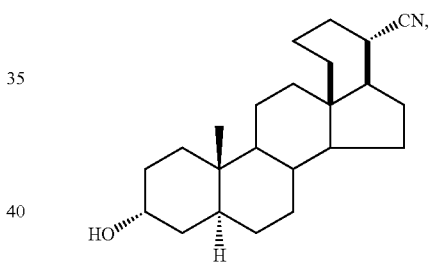
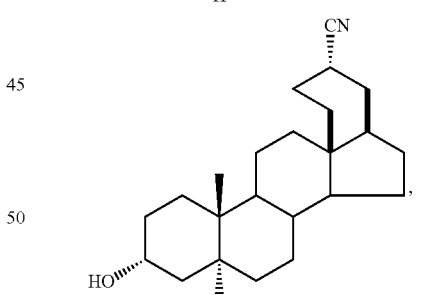
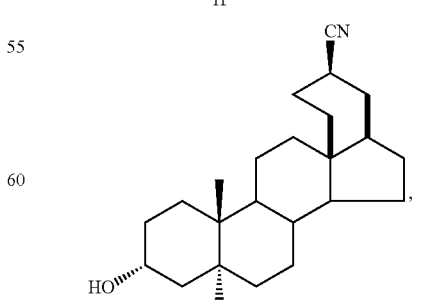

-continued
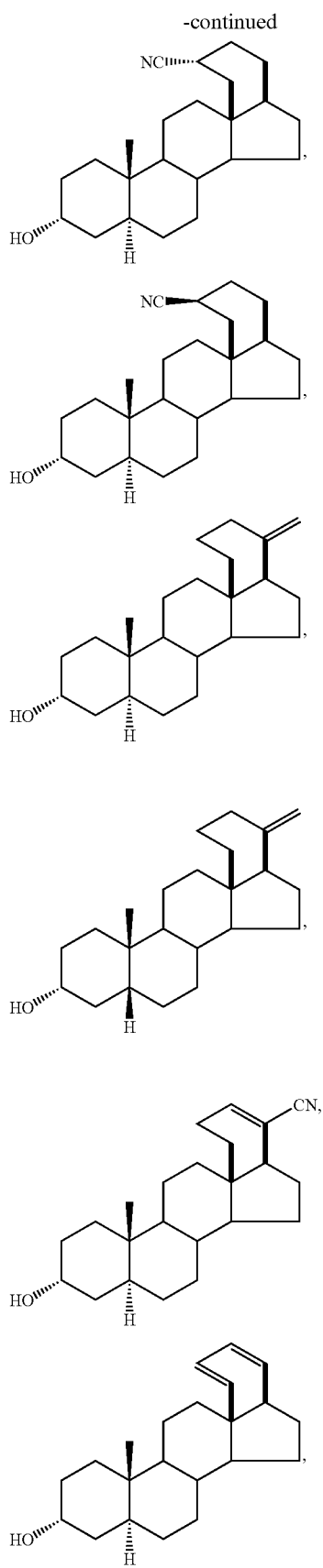
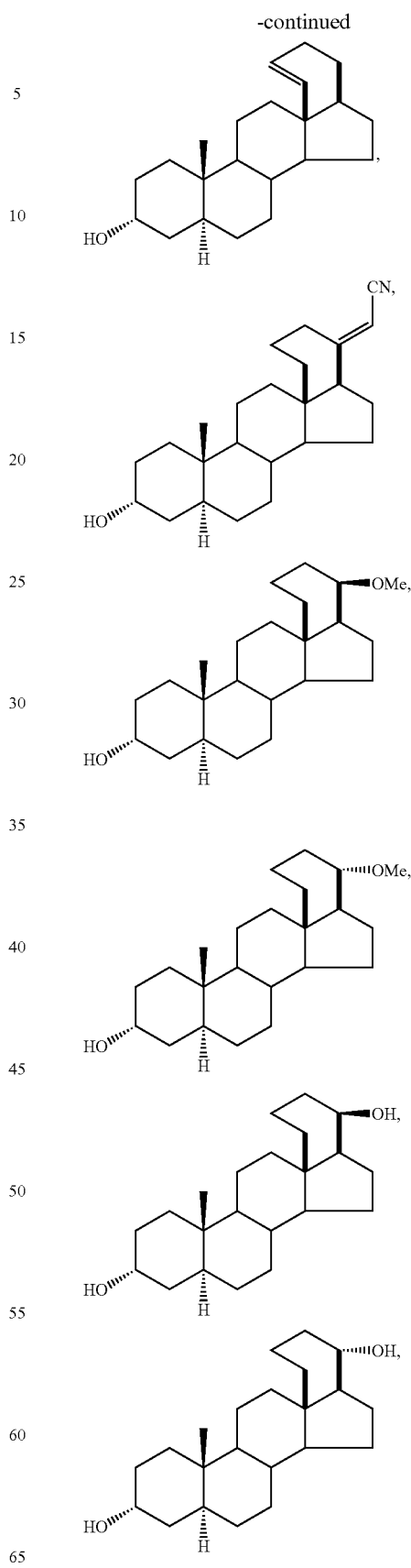

-continued
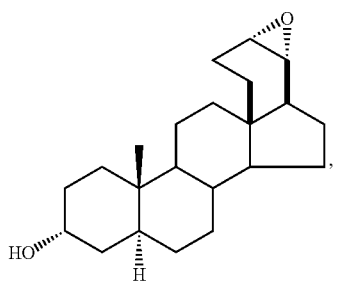
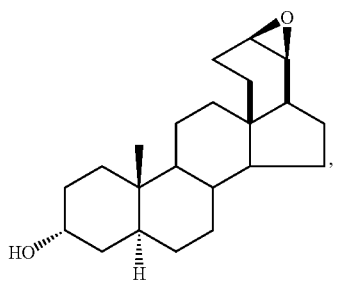
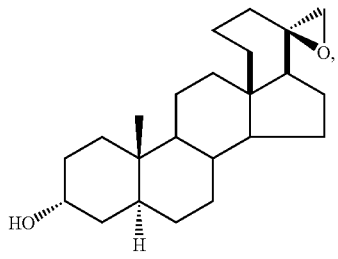
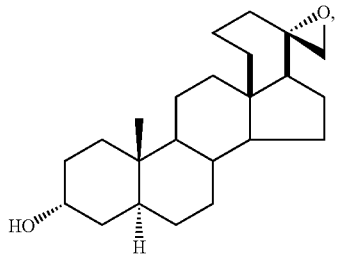
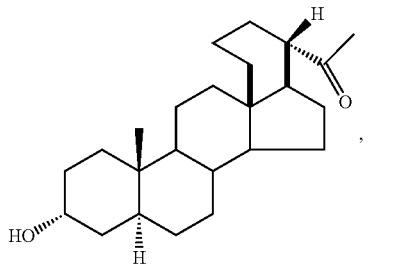
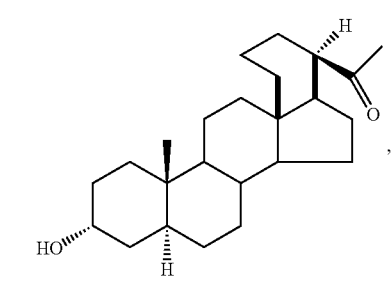
-continued
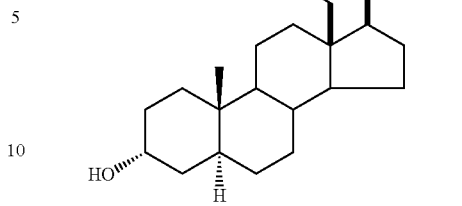
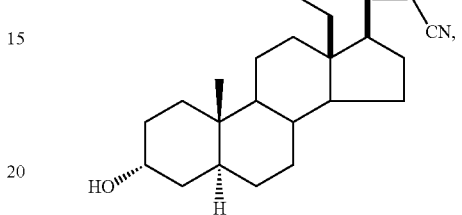
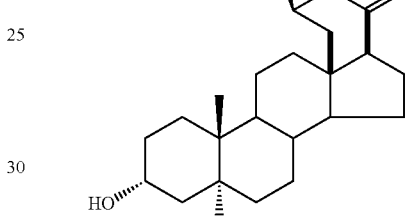
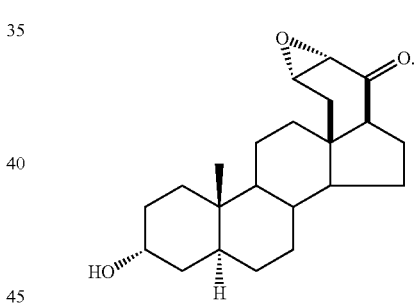
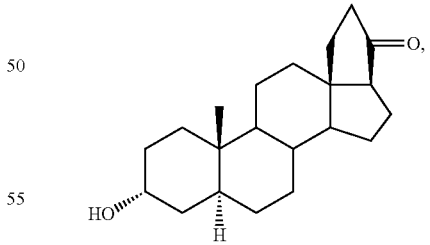
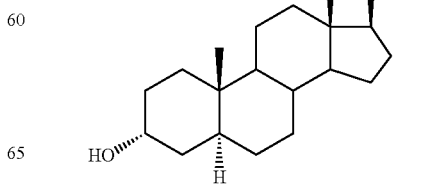

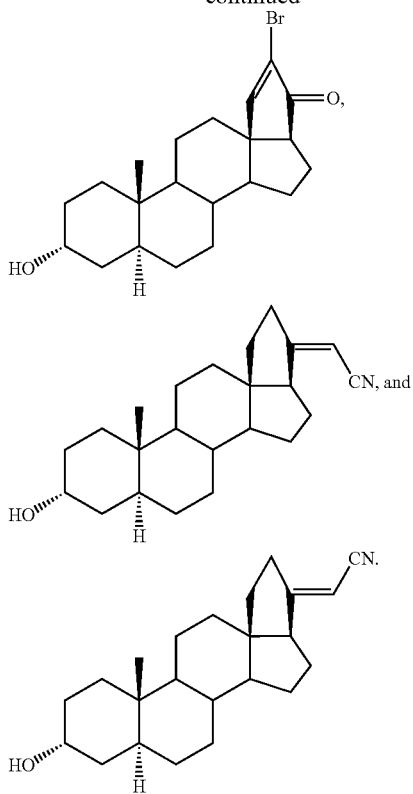

32. A method of inducing anesthesia in a mammal, said method comprising administering a therapeutically effective amount of a pharmaceutical composition containing the steroid or D-homosteroid of claim 1 and at least one pharmaceutically acceptable carrier.

33. A method of inducing anesthesia in a mammal, said method comprising administering a therapeutically effective amount of a pharmaceutical composition containing the steroid or D-homosteroid of claim 15 and at least one pharmaceutically acceptable carrier.

34. A method of inducing anesthesia in a mammal, said method comprising administering a therapeutically effective amount of a pharmaceutical composition containing the steroid or D-homosteroid of claim 27 and at least one pharmaceutically acceptable carrier.

35. The method of claim 32 wherein the steroid or D-homosteroid is Formula (B)

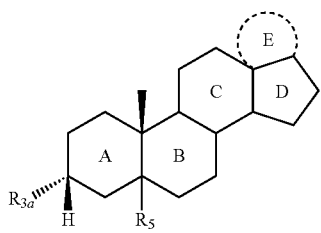

wherein $R_{3a}$ is hydroxyl or carboxyl; and
$R_5$ is α or β-hydrogen.

36. The method of claim 35 wherein the steroid or D-homosteroid is Formula (C)

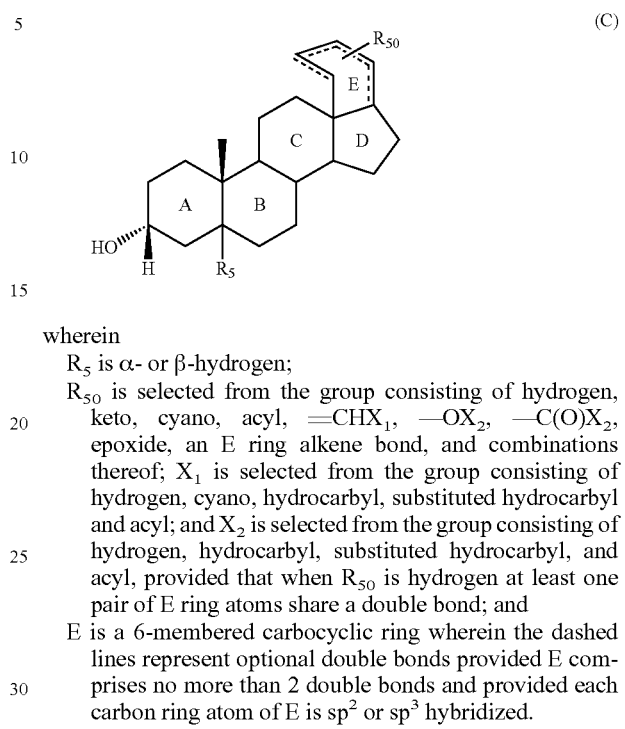

wherein $R_5$ is α- or β-hydrogen;
$R_{50}$ is selected from the group consisting of hydrogen, keto, cyano, acyl, =CHX$_1$, —OX$_2$, —C(O)X$_2$, epoxide, an E ring alkene bond, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl, provided that when $R_{50}$ is hydrogen at least one pair of E ring atoms share a double bond; and
E is a 6-membered carbocyclic ring wherein the dashed lines represent optional double bonds provided E comprises no more than 2 double bonds and provided each carbon ring atom of E is sp$^2$ or sp$^3$ hybridized.

37. The method of claim 35 wherein the steroid or D-homosteroid is Formula (D)

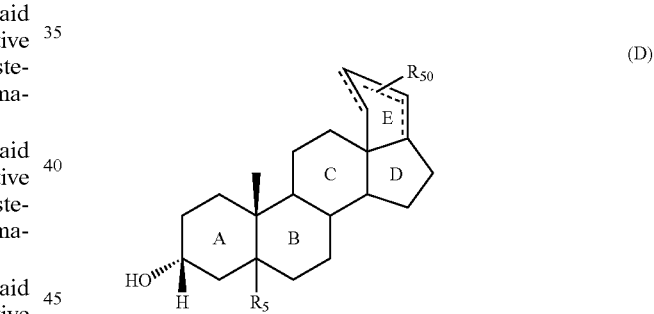

wherein $R_5$ is α- or β-hydrogen;
$R_{50}$ is selected from the group consisting of hydrogen, keto, cyano, acyl, =CHX$_1$, —OX$_2$, —C(O)X$_2$, epoxide, an E ring alkene bond, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl, provided that when $R_{50}$ is hydrogen at least one pair of E ring atoms share a double bond; and
E is a 5-membered carbocyclic ring wherein the dashed lines represent optional double bonds provided E comprises no more than 2 double bonds and provided each carbon ring atom of E is sp$^2$ or sp$^3$ hybridized.

38. The method of claim 32 wherein the hydrogen bond acceptor is selected from the group consisting of keto, cyano, acyl, =CHX$_1$, —OX$_2$, —C(O)X$_2$, epoxide, an E ring alkene bond, and combinations thereof; $X_1$ is selected from the group consisting of hydrogen, cyano, hydrocarbyl, substituted hydrocarbyl and acyl; and $X_2$ is selected from the group consisting of hydrogen, hydrocarbyl, substituted hydrocarbyl, and acyl.

39. A method of inducing anesthesia in a mammal, said method comprising administering a therapeutically effective amount of a pharmaceutical composition containing the steroid or D-homosteroid of claim 22 and at least one pharmaceutically acceptable carrier.

\* \* \* \* \*